US011692037B2

(12) United States Patent
Fujimoto et al.

(10) Patent No.: US 11,692,037 B2
(45) Date of Patent: Jul. 4, 2023

(54) ANTI-IL-6 RECEPTOR ANTIBODY-CONTAINING MEDICINAL COMPOSITION FOR PREVENTING POST-SURGICAL ADHESION

(71) Applicants: Hyogo College of Medicine, Hyogo (JP); Chugai Seiyaku Kabushiki Kaisha, Tokyo (JP)

(72) Inventors: Jiro Fujimoto, Hyogo (JP); Tomohiro Yoshimoto, Hyogo (JP); Naoki Uyama, Hyogo (JP)

(73) Assignees: Hyogo College of Medicine, Hyogo (JP); Chugai Seiyaku Kabushiki Kaisha, Tokyo (JP)

( * ) Notice: Subject to any disclaimer, the term of this patent is extended or adjusted under 35 U.S.C. 154(b) by 172 days.

(21) Appl. No.: 16/756,404

(22) PCT Filed: Oct. 19, 2018

(86) PCT No.: PCT/JP2018/038955
§ 371 (c)(1),
(2) Date: Apr. 15, 2020

(87) PCT Pub. No.: WO2019/078344
PCT Pub. Date: Apr. 25, 2019

(65) Prior Publication Data
US 2020/0299391 A1    Sep. 24, 2020

(30) Foreign Application Priority Data

Oct. 20, 2017  (JP) .............................. JP2017-203271

(51) Int. Cl.
*C07K 16/28*    (2006.01)
*A61K 39/00*    (2006.01)
*A61P 1/00*    (2006.01)
(52) U.S. Cl.
CPC ............ *C07K 16/2866* (2013.01); *A61P 1/00* (2018.01); *A61K 2039/505* (2013.01); *C07K 2317/76* (2013.01)
(58) Field of Classification Search
CPC ...................... A61K 2039/505; C07K 16/2866
See application file for complete search history.

(56) References Cited

U.S. PATENT DOCUMENTS

| | | | |
|---|---|---|---|
| 5,126,250 A | 6/1992 | McDonough et al. |
| 5,216,128 A | 6/1993 | Novick et al. |
| 5,530,101 A | 6/1996 | Queen et al. |
| 5,621,077 A | 4/1997 | Novick et al. |
| 5,639,455 A | 6/1997 | Shimamura et al. |
| 5,670,373 A | 9/1997 | Kishimoto |
| 5,795,965 A | 8/1998 | Tsuchiya et al. |
| 5,817,790 A | 10/1998 | Tsuchiya et al. |
| 5,856,135 A | 1/1999 | Tsuchiya et al. |
| 5,888,510 A | 3/1999 | Kishimoto et al. |
| 6,074,643 A | 6/2000 | Barbera-Guillem |
| 6,121,423 A | 9/2000 | Tsuchiya et al. |
| 6,261,560 B1 | 7/2001 | Tsujinaka et al. |
| 6,309,636 B1 | 10/2001 | Do Couto et al. |
| 6,552,083 B1 | 4/2003 | Isobe et al. |
| 6,723,319 B1 | 4/2004 | Ito et al. |
| 7,291,721 B2 | 11/2007 | Giles-Komar et al. |
| 7,320,792 B2 | 1/2008 | Ito et al. |
| 7,414,024 B2 | 8/2008 | Blay et al. |
| 7,438,907 B2 | 10/2008 | Schuurman et al. |
| 7,479,543 B2 | 1/2009 | Tsuchiya et al. |
| 7,521,052 B2 | 4/2009 | Okuda et al. |
| 7,582,298 B2 | 9/2009 | Stevens et al. |
| 7,759,472 B2 | 7/2010 | Shima et al. |
| 7,781,617 B2 | 8/2010 | Kudou et al. |
| 7,824,674 B2 | 11/2010 | Ito et al. |
| 7,825,109 B2 | 11/2010 | Nakade et al. |
| 7,884,196 B2 | 2/2011 | Lawless |
| 7,935,340 B2 | 5/2011 | Garcia-Martinez et al. |
| 7,955,590 B2 | 6/2011 | Gillies et al. |
| 8,017,121 B2 | 9/2011 | Kishimoto et al. |
| 8,226,611 B2 | 7/2012 | Chen et al. |
| 8,323,649 B2 | 12/2012 | Garcia-Martinez et al. |
| 8,398,980 B2 | 3/2013 | Kano et al. |
| 8,470,316 B2 | 6/2013 | Yasunami |
| 8,562,991 B2 | 10/2013 | Igawa et al. |
| 8,580,264 B2 | 11/2013 | Zhang et al. |
| 8,623,355 B2 | 1/2014 | Okada et al. |
| 8,771,686 B2 | 7/2014 | Ishida |
| 8,945,558 B2 | 2/2015 | Kobara |
| 9,017,677 B2 | 4/2015 | Mihara |
| 9,096,651 B2 | 8/2015 | Igawa et al. |

(Continued)

FOREIGN PATENT DOCUMENTS

AR    068564 A1    11/2009
CA    1332367 C    10/1994

(Continued)

OTHER PUBLICATIONS

Dirk Schmidt-Arras et al., Journal of Hepatology vol. 64 j 1403-1415 (Year: 2016).*
Abdalla, A. M. E., et al., "Current Challenges of Cancer Antiangiogenic Therapy and the Promise of Nanotherapeutics," Theranostics 8(2):533-549 (2018).
Abiatari, I., et al., "Consensus Transcriptome Signature of Perineural Invasion in Pancreatic Carcinoma," Molecular Cancer Therapeutics 8:1494-1504 (2009).
Airoldi, I., et al., "IL-12 can Target Human Lung Adenocarcinoma Cells and Normal Bronchial Epithelial Cells Surrounding Tumor Lesions," PloS One 4(7):e6119 (2006).

(Continued)

*Primary Examiner* — Prema M Mertz
(74) *Attorney, Agent, or Firm* — Nixon & Vanderhye P.C.

(57) ABSTRACT

Postoperative adhesion formation at an invasion site and migration of neutrophils to the site of surgical invasion are suppressed by administering an anti-IL-6 receptor antibody and/or a neutrophil-neutralizing antibody.

11 Claims, 14 Drawing Sheets

Specification includes a Sequence Listing.

(56) References Cited

U.S. PATENT DOCUMENTS

| | | |
|---|---|---|
| 9,260,516 B2 | 2/2016 | Nishimoto et al. |
| 9,539,322 B2 | 1/2017 | Nishimura |
| 9,688,762 B2 | 6/2017 | Igawa et al. |
| 9,725,514 B2 | 8/2017 | Takahashi et al. |
| 10,662,245 B2 | 5/2020 | Igawa et al. |
| 10,697,883 B2 | 6/2020 | Yamamura et al. |
| 10,717,781 B2 | 7/2020 | Mitsunaga et al. |
| 10,774,148 B2 | 9/2020 | Kakehi et al. |
| 10,782,290 B2 | 9/2020 | Yamamura et al. |
| 2001/0001663 A1 | 5/2001 | Kishimoto et al. |
| 2002/0119150 A1 | 8/2002 | Kirk et al. |
| 2002/0187150 A1 | 12/2002 | Mihara et al. |
| 2004/0018540 A1 | 1/2004 | Yamamura et al. |
| 2004/0028681 A1 | 2/2004 | Ito et al. |
| 2004/0071706 A1 | 4/2004 | Ito et al. |
| 2004/0170626 A1 | 9/2004 | Schuurman et al. |
| 2005/0096257 A1 | 5/2005 | Shima et al. |
| 2005/0142635 A1 | 6/2005 | Tsuchiya et al. |
| 2005/0158317 A1 | 7/2005 | Blay et al. |
| 2005/0182007 A1 | 8/2005 | McSwiggen et al. |
| 2005/0261229 A1 | 11/2005 | Gillies et al. |
| 2005/0272634 A1 | 12/2005 | Bahlmann et al. |
| 2006/0039902 A1 | 2/2006 | Young et al. |
| 2006/0111316 A1 | 5/2006 | Lawless |
| 2006/0134113 A1 | 6/2006 | Mihara |
| 2006/0165696 A1 | 7/2006 | Okano et al. |
| 2006/0188502 A1 | 8/2006 | Giles-Komar et al. |
| 2006/0193772 A1 | 8/2006 | Ochiai et al. |
| 2006/0251653 A1 | 11/2006 | Okuda et al. |
| 2006/0292147 A1 | 12/2006 | Yoshizaki et al. |
| 2007/0036785 A1 | 2/2007 | Kishimoto et al. |
| 2007/0134242 A1 | 6/2007 | Nishimoto et al. |
| 2007/0167425 A1 | 7/2007 | Nakade et al. |
| 2007/0280945 A1 | 12/2007 | Stevens et al. |
| 2008/0032923 A1 | 2/2008 | Kudou et al. |
| 2008/0081041 A1 | 4/2008 | Nemeth |
| 2009/0022719 A1 | 1/2009 | Mihara et al. |
| 2009/0022726 A1 | 1/2009 | Zaki et al. |
| 2009/0028784 A1 | 1/2009 | Garcia-Martinez et al. |
| 2009/0220499 A1 | 9/2009 | Yasunami |
| 2009/0220500 A1 | 9/2009 | Kobara |
| 2009/0263384 A1 | 10/2009 | Okada et al. |
| 2009/0269335 A1 | 10/2009 | Nakashima et al. |
| 2009/0291076 A1 | 11/2009 | Morichika et al. |
| 2010/0008907 A1 | 1/2010 | Nishimoto et al. |
| 2010/0034811 A1 | 2/2010 | Ishida |
| 2010/0061986 A1 | 3/2010 | Takahashi et al. |
| 2010/0129357 A1 | 5/2010 | Garcia-Martinez et al. |
| 2010/0247523 A1 | 9/2010 | Kano et al. |
| 2010/0298542 A1 | 11/2010 | Igawa et al. |
| 2010/0316636 A1 | 12/2010 | Radin et al. |
| 2011/0076275 A1 | 3/2011 | Igawa et al. |
| 2011/0098450 A1 | 4/2011 | Igawa et al. |
| 2011/0111406 A1 | 5/2011 | Igawa et al. |
| 2011/0150869 A1 | 6/2011 | Mitsunaga et al. |
| 2011/0245473 A1 | 10/2011 | Igawa et al. |
| 2012/0045453 A1 | 2/2012 | Chen et al. |
| 2012/0183539 A1 | 7/2012 | Maeda |
| 2012/0253016 A1 | 10/2012 | Igawa et al. |
| 2012/0301460 A1 | 11/2012 | Bao et al. |
| 2013/0202588 A1 | 8/2013 | Nishimura |
| 2013/0317203 A1 | 11/2013 | Igawa et al. |
| 2016/0022812 A1 | 1/2016 | Mitsunaga et al. |
| 2016/0139117 A1 | 5/2016 | Yamamura et al. |
| 2017/0121412 A1 | 5/2017 | Igawa et al. |
| 2017/0362304 A1 | 12/2017 | Fukuda et al. |
| 2018/0148509 A1 | 5/2018 | Kakehi et al. |
| 2018/0149573 A1 | 5/2018 | Yamamura et al. |
| 2019/0085085 A1 | 3/2019 | Igawa et al. |
| 2020/0148760 A1 | 5/2020 | Matsuoka et al. |
| 2020/0231688 A1 | 7/2020 | Igawa et al. |
| 2021/0017286 A1 | 1/2021 | Kakehi et al. |
| 2021/0206862 A1 | 7/2021 | Igawa et al. |
| 2021/0363238 A1 | 11/2021 | Kato |
| 2022/0041741 A1 | 2/2022 | Igawa et al. |
| 2022/0204608 A1 | 6/2022 | Honda et al. |
| 2022/0220210 A1 | 7/2022 | Takeshita et al. |

FOREIGN PATENT DOCUMENTS

| | | |
|---|---|---|
| CA | 2203182 A1 | 5/1996 |
| CA | 2443294 A1 | 10/2002 |
| CA | 2523577 A1 | 11/2004 |
| CA | 2549467 A1 | 7/2005 |
| CA | 2560953 A1 | 9/2005 |
| CA | 2625773 A1 | 4/2007 |
| CA | 2626688 A1 | 4/2007 |
| CA | 2648644 A1 | 10/2007 |
| CA | 2700394 A1 | 4/2009 |
| CA | 2700498 A1 | 4/2009 |
| CA | 2203182 C | 11/2009 |
| CA | 2549467 C | 12/2012 |
| CA | 2443294 C | 9/2013 |
| CA | 2700498 C | 1/2016 |
| CA | 2700394 C | 10/2017 |
| CN | 1164194 A | 11/1997 |
| CN | 1297357 A | 5/2001 |
| CN | 1694894 A | 11/2005 |
| CN | 1849135 A | 10/2006 |
| CN | 100374159 C | 3/2008 |
| CN | 100374457 C | 3/2008 |
| CN | 101849006 A | 9/2010 |
| CN | 103476793 A | 12/2013 |
| EP | 0361902 A2 | 4/1990 |
| EP | 0721783 A1 | 7/1996 |
| EP | 0783893 A1 | 7/1997 |
| EP | 0791359 A1 | 8/1997 |
| EP | 0811384 A1 | 12/1997 |
| EP | 0628639 B1 | 6/1999 |
| EP | 0931544 A2 | 7/1999 |
| EP | 0983767 A1 | 3/2000 |
| EP | 1004315 A1 | 5/2000 |
| EP | 1074268 A1 | 2/2001 |
| EP | 1108435 A1 | 6/2001 |
| EP | 1197210 A1 | 4/2002 |
| EP | 1334731 A1 | 8/2003 |
| EP | 1374900 A1 | 1/2004 |
| EP | 1562968 A1 | 8/2005 |
| EP | 1690550 A1 | 8/2006 |
| EP | 1707215 A1 | 10/2006 |
| EP | 1728801 A1 | 12/2006 |
| EP | 1733740 A1 | 12/2006 |
| EP | 1074268 B1 | 1/2008 |
| EP | 1334731 B1 | 2/2008 |
| EP | 1004315 B1 | 5/2008 |
| EP | 1941907 A1 | 7/2008 |
| EP | 1941908 A1 | 7/2008 |
| EP | 0983767 B1 | 9/2008 |
| EP | 1967207 A1 | 9/2008 |
| EP | 1967209 A1 | 9/2008 |
| EP | 1990060 A1 | 11/2008 |
| EP | 2025346 A1 | 2/2009 |
| EP | 2123302 A1 | 11/2009 |
| EP | 2174667 A1 | 4/2010 |
| EP | 2194066 A1 | 6/2010 |
| EP | 2196220 A1 | 6/2010 |
| EP | 2202245 A1 | 6/2010 |
| EP | 2206775 A1 | 7/2010 |
| EP | 2275443 A1 | 1/2011 |
| EP | 2305306 A1 | 4/2011 |
| EP | 2330193 A1 | 6/2011 |
| EP | 1707215 B1 | 3/2012 |
| EP | 1967209 B1 | 6/2012 |
| EP | 1690550 B1 | 8/2012 |
| EP | 2578233 A1 | 4/2013 |
| EP | 2639305 A1 | 9/2013 |
| EP | 2196220 B1 | 12/2014 |
| EP | 1941908 B1 | 8/2015 |
| EP | 2123302 B1 | 12/2015 |
| EP | 2305306 B1 | 2/2016 |
| EP | 1941907 B1 | 3/2016 |
| EP | 3009518 A1 | 4/2016 |
| EP | 1967207 B1 | 6/2016 |

(56) References Cited

FOREIGN PATENT DOCUMENTS

| | | |
|---|---|---|
| EP | 2174667 B1 | 1/2017 |
| EP | 2578233 B1 | 4/2017 |
| EP | 3483283 A1 | 5/2019 |
| EP | 3009518 B1 | 8/2020 |
| ES | 2276525 T3 | 6/2007 |
| FR | 2694767 A1 | 2/1994 |
| JP | H02163096 A | 6/1990 |
| JP | H06505253 A | 6/1994 |
| JP | H06237772 A | 8/1994 |
| JP | H0746998 A | 2/1995 |
| JP | H07505609 A | 6/1995 |
| JP | H08208514 A | 8/1996 |
| JP | H1189582 A | 4/1999 |
| JP | 2925181 B2 | 7/1999 |
| JP | H11180873 A | 7/1999 |
| JP | 3067987 B2 | 7/2000 |
| JP | 2002527354 A | 8/2002 |
| JP | 3345419 B2 | 11/2002 |
| JP | 2003525243 A | 8/2003 |
| JP | 2004028926 A | 1/2004 |
| JP | 3525221 B2 | 5/2004 |
| JP | 3614183 B2 | 1/2005 |
| JP | 2005524606 A | 8/2005 |
| JP | 2005281235 A | 10/2005 |
| JP | 2006503001 A | 1/2006 |
| JP | 2006512325 A | 4/2006 |
| JP | 2006524685 A | 11/2006 |
| JP | 3856734 B2 | 12/2006 |
| JP | 2007528691 A | 10/2007 |
| JP | 2008037875 A | 2/2008 |
| JP | 2008037876 A | 2/2008 |
| JP | 2008538931 A | 11/2008 |
| JP | 2008297315 A | 12/2008 |
| JP | 4468578 B2 | 5/2010 |
| JP | 2010527615 A | 8/2010 |
| JP | 4609877 B2 | 1/2011 |
| JP | 4698652 B2 | 6/2011 |
| JP | 4763043 B2 | 8/2011 |
| JP | 4799516 B2 | 10/2011 |
| JP | 2012500020 A | 1/2012 |
| JP | 4869063 B2 | 2/2012 |
| JP | 2013541594 A | 11/2013 |
| JP | 5530635 B2 | 6/2014 |
| JP | 5685535 B2 | 3/2015 |
| JP | 5833823 B2 | 12/2015 |
| KR | 20060010765 A | 2/2006 |
| KR | 20070035482 A | 3/2007 |
| RU | 2127117 C1 | 3/1999 |
| RU | 2147442 C1 | 4/2000 |
| RU | 2195960 C2 | 1/2003 |
| RU | 2430111 C1 | 9/2011 |
| TW | 200803895 A | 1/2008 |
| TW | 201021829 A | 6/2010 |
| TW | 201302219 A1 | 1/2013 |
| TW | I440469 B | 6/2014 |
| WO | WO 9212729 A1 | 8/1992 |
| WO | WO-9219759 A1 | 11/1992 |
| WO | WO-9308817 A1 | 5/1993 |
| WO | WO-9420488 A1 | 9/1994 |
| WO | WO-9428159 A1 | 12/1994 |
| WO | WO-9509873 A1 | 4/1995 |
| WO | WO-9611020 A1 | 4/1996 |
| WO | WO 9612503 A1 | 5/1996 |
| WO | WO-9625174 A1 | 8/1996 |
| WO | WO-9836061 A2 | 8/1998 |
| WO | WO 9842377 A1 | 10/1998 |
| WO | WO 9908707 A1 | 2/1999 |
| WO | WO 9947170 A1 | 9/1999 |
| WO | WO-9958572 A1 | 11/1999 |
| WO | WO-9960013 A2 | 11/1999 |
| WO | WO-0010607 A1 | 3/2000 |
| WO | WO-0105394 A1 | 1/2001 |
| WO | WO-0145678 A2 | 6/2001 |
| WO | WO 0164214 A2 | 9/2001 |
| WO | WO-0203492 A1 | 1/2002 |
| WO | WO 0234292 A1 | 5/2002 |
| WO | WO 02080969 A1 | 10/2002 |
| WO | WO-03048205 A2 | 6/2003 |
| WO | WO-03105861 A1 | 12/2003 |
| WO | WO-2004007701 A1 | 1/2004 |
| WO | WO-2004039826 A1 | 5/2004 |
| WO | WO-2004045507 A2 | 6/2004 |
| WO | WO-2004045512 A2 | 6/2004 |
| WO | WO 2004045520 A2 | 6/2004 |
| WO | WO-2004071404 A2 | 8/2004 |
| WO | WO-2004073741 A1 | 9/2004 |
| WO | WO 2004096273 A1 | 11/2004 |
| WO | WO-2005028514 A1 | 3/2005 |
| WO | WO 2005037315 A1 | 4/2005 |
| WO | WO-2005044848 A1 | 5/2005 |
| WO | WO 2005061000 A1 | 7/2005 |
| WO | WO-2005080429 A2 | 9/2005 |
| WO | WO-2005090405 A1 | 9/2005 |
| WO | WO-2005107800 A1 | 11/2005 |
| WO | WO-2006009092 A1 | 1/2006 |
| WO | WO-2006023144 A2 | 3/2006 |
| WO | WO-2006070286 A2 | 7/2006 |
| WO | WO-2006072954 A2 | 7/2006 |
| WO | WO-2006119115 A2 | 11/2006 |
| WO | WO 2007043641 A1 | 4/2007 |
| WO | WO 2007046489 A1 | 4/2007 |
| WO | WO 2007058194 A1 | 5/2007 |
| WO | WO 2007061029 A1 | 5/2007 |
| WO | WO-2007067976 A2 | 6/2007 |
| WO | WO-2007074880 A1 | 7/2007 |
| WO | WO-2007076927 A1 | 7/2007 |
| WO | WO 2007086490 A1 | 8/2007 |
| WO | WO-2007114319 A1 | 10/2007 |
| WO | WO-2007116962 A1 | 10/2007 |
| WO | WO-2007137984 A2 | 12/2007 |
| WO | WO-2007143168 A2 | 12/2007 |
| WO | WO-2008020079 A1 | 2/2008 |
| WO | WO 2008090901 A1 | 7/2008 |
| WO | WO-2008144763 A2 | 11/2008 |
| WO | WO-2009010539 A2 | 1/2009 |
| WO | WO 2009014263 A1 | 1/2009 |
| WO | WO-2009041613 A1 | 4/2009 |
| WO | WO-2009041621 A1 | 4/2009 |
| WO | WO-2009041643 A1 | 4/2009 |
| WO | WO 2009044774 A1 | 4/2009 |
| WO | WO-2009125825 A1 | 10/2009 |
| WO | WO 2009148148 A1 | 12/2009 |
| WO | WO-2010021697 A2 | 2/2010 |
| WO | WO-2010035769 A1 | 4/2010 |
| WO | WO 2010065078 A1 | 6/2010 |
| WO | WO-2010107108 A1 | 9/2010 |
| WO | WO-2011013786 A1 | 2/2011 |
| WO | WO 2011149046 A1 | 12/2011 |
| WO | WO-2011149051 A1 | 12/2011 |
| WO | WO-2011154139 A2 | 12/2011 |
| WO | WO-2012063875 A1 | 5/2012 |
| WO | WO 2012064627 A2 | 5/2012 |
| WO | WO-2012118750 A2 | 9/2012 |
| WO | WO-2014200018 A1 | 12/2014 |
| WO | WO-2016027859 A1 | 2/2016 |
| WO | WO-2016104777 A1 | 6/2016 |
| WO | WO-2016136933 A1 | 9/2016 |
| WO | WO-2016186154 A1 | 11/2016 |
| WO | WO-2018008750 A1 | 1/2018 |
| WO | WO-2018203545 A1 | 11/2018 |
| WO | WO-2019151418 A1 | 8/2019 |
| WO | WO-2020202839 A1 | 10/2020 |
| WO | WO-2020213665 A1 | 10/2020 |

OTHER PUBLICATIONS

Akira, S. and Kishimoto T., "The Evidence for Interleukin-6 as an Autocrine Growth Factor in Malignancy," Seminars in Cancer Biology 3(1):17-26 (1992).

Akira, S., et al., "Interleukin-6 in Biology and Medicine," Advances in immunology 54:1-78 (1993).

Almand, B., et al., "Clinical Significance of Defective Dendritic Cell Differentiation in Cancer," Clinical Cancer Research 6:1755-1766 (2000).

(56) References Cited

OTHER PUBLICATIONS

Almand, B., et al., "Increased Production of Immature Myeloid Cells in Cancer Patients: A Mechanism of Immunosuppression in Cancer," Journal of Immunology 166:678-689 (2001).
Alvarez, B., et al.,"Tumor Necrosis Factor-a Exerts Interleukin-6-Dependent and -Independent Effects on Cultured Skeletal Muscle Cells," Biochimica et Biophysica Acta (BBA) 1542(1-3): 66-72 (2002).
Ando, K., et al., "Tocilizumab, a Proposed Therapy for the Cachexia of Interleukin6-Expressing Lung Cancer," PLOS One, 9(7):e102436 (2014).
Annual Report 2012, "Integrated Edition Including CSR Report," Chugai Pharmaceutical Co., Ltd., 154 (2013).
Ano, S., et al., "Transcription Factors GATA-3 and RORγt are Important for Determining the Phenotype of Allergic Airway Inflammation in a Murine Model of Asthma," Journal of Immunology 190(3):1056-1065 (2013).
Anzctr, Registered Trial, Trial Review, "A Clinical Trial of Tocilizumab in Participants with Asthma," accessed at https://www.anzctr.org.au/Trial/Registration/TrialReview.aspx?id=365668, Registered on Feb. 3, 2014, Reg. No. ACTRN12614000123640.
Araki, et al., "Emerging Disease-modifying Therapies for Neuromyelitis Optica Spectrum Disorder," The Medical Frontline 71:1159-1167 (2016).
Araki, M., et al., "Clinical Improvement in a Patient With Neuromyelitis Optica Following Therapy With the Anti-il-6 Receptor Monoclonal Antibody Tocilizumab," Modern Rheumatology 23(4):827-831 (2013).
Araki, M., et al., "Efficacy of the Anti-il-6 Receptor Antibody Tocilizumab in Neuromyelitis Optica," Neurology 82(15): 1302-1306 (2014).
Aricha, R., et al.."Blocking of Il-6 Suppresses Experimental Autoimmune Myasthenia Gravis," Journal of Autoimmunity 36(2): 135-141 (2011).
Arima, Y., et al., "Regional Neural Activation Defines a Gateway for Autoreactive T Cells to Cross the Blood-Brain Barrier," Cell 148(3):447-457 (2012).
Armour, K.L., et al., "Recombinant Human IgG Molecules Lacking Fcgamma Receptor I Binding and Monocyte Triggering Activities," European Journal of Immunology 29(8):2613-2624 (1999).
Armstrong, C.A., et al., "Melanoma-derived Interleukin 6 Inhibits in Vivo Melanoma Growth," The Journal of Investigative Dermatology 102(3):278-284 (1994).
Ashizawa, T., et al., "Clinical Significance of Interleukin-6 (IL-6) in the Spread of Gastric Cancer: Role of IL-6 as a Prognostic Factor", Gastric Cancer 8:124-131 (2005).
Audenet, F., et al., "The Evolution of Bladder Cancer Genomics: What Have We Learned and How Can We Use It?," Urologic Oncology 36(7):313-320 (2018).
Barkhof, F., et al., "Comparison of MRI Criteria at First Presentation to Predict Conversion to Clinically Definite Multiple Sclerosis", Brain 120:2059-2069 (1997).
Bartelds, G.M., et al., "Clinical Response to Adalimumab: Relationship to Anti-Adalimumab Antibodies and Serum Adalimumab Concentrations in Rheumatoid Arthritis," Annals of the Rheumatic Diseases 66(7):921-926 (2007).
Barton-Davis, E.R., et al., "Viral Mediated Expression of Insulin-Like Growth Factor I Blocks the Aging-related Loss of Skeletal Muscle Function," PNAS 95(26):15603-15607 (1998).
Beck, J., et al., "Brief Report: Alleviation of Systemic Manifestations of Castleman's Disease by Monoclonal Anti-interleukin-6 Antibody," The New England Journal of Medicine 330(9):602-605 (1994).
Becker, Y., "Molecular Immunological Approaches to Biotherapy of Human Cancers—A Review, Hypothesis and Implications", Anticancer Research 29:1113-1134 (2006).
Bellomo, R.,"The Cytokine Network in the Critically Ill," Anaesthesia and Intensive Care 20(3): 288-302 (1992).
Benda, B. and Korsgren, O., "Interleukin-6 in Islet Xenograft Rejection," Transplant international 14(2):63-71 (2001).

Bender, N.K., et al., "Immunogenicity, Efficacy and Adverse Events of Adalimumab in RA Patients," Rheumatology International 27(3):269-274 (2007).
Berger, T., et al., "Disruption of the Lcn2 Gene in Mice Suppresses Primary Mammary Tumor Formation but Does Not Decrease Lung Metastasis", PNAS 107:2995-3000 (2010).
Bertagnolli, M.M., et al., "IL-4-Supported Induction of Cytolytic T Lymphocytes Requires IL-2 and IL-6," Cellular Immunology 133(2):327-341 (1991).
Besada, E.,"Potential Patient Benefit of a Subcutaneous Formulation of Tocilizumab for the Treatment of Rheumatoid Arthritis: a Critical Review," Patient Preference and Adherence 8: 1051-1059 (2014).
Besse, B., et al., "Phase 2 Study of Frontline Bortezomib in Patients With Advanced Non-small Cell Lung Cancer," Lung Cancer 76(1):78-83 (2012).
Biswas, P.S., et al., "Involvement of IL-6 in the Paracrine Production of VEGF in Ocular HSV-1 Infection," Experimental Eye Research 82(1):46-54 (2006).
Bogdanovich, S., et al.."Functional Improvement of Dystrophic Muscle by Myostatin Blockade," Nature 420: 418-421 (2002).
Bonapace, L., et al., "Cessation of CCL2 Inhibition Accelerates Breast Cancer Metastasis by Promoting Angiogenesis," Nature 515(7525):130-133 (2014).
Bond, M., et al., "Synergistic Upregulation of Metalloproteinase-9 by Growth Factors and Inflammatory Cytokines: an Absolute Requirement for Transcription Factor Nf-kappa B," FEBS Letters 435(1):29-34 (1998).
Borg, A.J., et al., "15-Deoxyspergualin Inhibits Interleukin 6 Production in in Vitro Stimulated Human Lymphocytes", Transplant Immunology 4:133-143 (1996).
Bork, P. and Bairoch, A., "Go Hunting in Sequence Databases But Watch Out for the Traps," Trends in Genetics 12(10):425-427 (1996).
Bork, P.,"Powers and Pitfalls in Sequence Analysis: the 70% Hurdle," Genome Research 10(4): 398-400 (2000).
Borsellino, N., et al., "Blocking Signaling Through the Gp130 Receptor Chain by Interleukin-6 and Oncostatin M Inhibits Pc-3 Cell Growth and Sensitizes the Tumor Cells to Etoposide and Cisplatin-mediated Cytotoxicity," Cancer 85(1):134-144 (1999).
Brenner, S.E., "Errors in Genome Annotation," Trends in Genetics 15(4):132-133 (1999).
Bromberg, "The IL-6/Jak/Stat3 Pathway: Targeting Metastatic Breast Cancer Research Update," www.mountainsofhopefoundation.org, 4 pages (2009).
Brown, M., et al., "Tolerance of Single, but Not Multiple, Amino Acid Replacements in Antibody Vh Cdr 2: a Means of Minimizing B Cell Wastage From Somatic Hypermutation?," Journal of Immunology 156(9):3285-3291 (1996).
Burska, A.N., et al., "Gene Expression Analysis in RA: Towards Personalized Medicine," The Pharmacogenomics Journal 14(2):93-106 (2014).
Cabillic, F., et al., "Interleukin-6 and Vascular Endothelial Growth Factor Release by Renal Cell Carcinoma Cells Impedes Lymphocyte-dendritic Cell Cross-talk," Clinical and Experimental Immunology 146(3):518-523 (2006).
Campbell, I.L., et al., "Essential Role for Interferon-gamma and Interleukin-6 in Autoimmune Insulin-dependent Diabetes in NOD/Wehi Mice", The Journal of Clinical Investigation 87:739-742 (1991).
Campbell, I.L., et al., "Evidence for IL-6 Production by and Effects on the Pancreatic Beta-Cell," Journal of Immunology 143(4):1188-1191 (1989).
Campo, S., et al.."Comparative Activity of Sant7 and Anti-IL-6, Il-6R Monoclonal Antibodies in a Murine Model of B-cell Lymphoma," Cytokine 31(5): 368-374 (2005).
Campochiaro, P.A.,"Retinal and Choroidal Neovascularization,"Journal of Cellular Physiology 184(3):301-310 (2000).
Capelo, A.V., et al., "Visceral Adiposity is Associated with Cytokines and Decrease in Lung Function in Women with Persistent Asthma," Revista Portuguesa De Pneumologia 22(5):255-61 (2016).

(56) References Cited

OTHER PUBLICATIONS

Ceyhan, G.O., et al., "Neural Invasion in Pancreatic Cancer: A Mutual Tropism Between Neurons and Cancer Cells," Biochemical and Biophysical Research Communications 374:442-447 (2008).
Chargé, S.B., and Rudnicki, M.A.,"Cellular and Molecular Regulation of Muscle Regeneration," Physiological Reviews 84(1): 209-238 (2004).
Chau, L.A., et al., "HuM291 (Nuvion), a Humanized Fc Receptor-Nonbinding Antibody Against CD3, Anergizes Peripheral Blood T Cells as Partial Agonist of the T Cell Receptor," Transplantation 71(7):941-950 (2001).
Cheong, Y.C., et al., "Peritoneal Healing and Adhesion Formation/Reformation," Human Reproduction Update 7(6):556-566 (2001).
Chien, N.C., et al., "Significant Structural and Functional Change of an Antigen-binding Site by a Distant Amino Acid Substitution: Proposal of a Structural Mechanism," PNAS 86(14):5532-5536 (1989).
Chihara, et al., "Autoantibody Producing Cells in Neuromyelitis Optica," Journal of Clinical and Experimental Medicine 240:534-535 (2012).
Chirino, A.J., et al., "Minimizing the Immunogenicity of Protein Therapeutics," Drug Discovery Today 9(2):82-90 (2004).
Choi, S.E., et al.,"IL-6 Protects Pancreatic Islet Beta Cells From Pro-inflammatory Cytokines-Induced Cell Death and Functional Impairment in Vitro and in Vivo," Transplant Immunology 13(1): 43-53 (2004).
Choy, E., "Inhibiting Interleukin-6 in Rheumatoid Arthritis," Current Rheumatology Reports 10(5):413-417 (2008).
Christensen, J.R., et al., "Systemic Inflammation in Progressive Multiple Sclerosis Involves Follicular T-Helper, Th17- and Activated B-Cells and Correlates with Progression," PLoS ONE vol. 8:e57820 (2013).
Chu, G.C., et al., "Accumulation of Succinimide in a Recombinant Monoclonal Antibody in Mildly Acidic Buffers Under Elevated Temperatures," Pharmaceutical Research 24(6):1145-1156 (2007).
Chu, S.Y., et al., "Reduction of Total IgE by Targeted Coengagement of IgE B-Cell Receptor and FcγRIIb with Fc-Engineered Antibody," The Journal of Allergy and Clinical Immunology 129(4):1102-1115 (2012).
Chu, D. K., et al., "Therapeutic potential of anti-IL-6 therapies for granulocytic airway inflammation in asthma," Allergy, Asthma Clin Immunol., 11:14 (2015).
"Chugai NMO Clinical Trial Webinar," Sakura Star Study, Dec. 12, 2014, accessed at https://s3.amazonaws.com/gjcf-wp-uploads/wp-content/uploads/2016/05/16162202/12_12_14_Chugai_Webinar_PPT_Complete_Deck_FINAL.pdf, accessed on Sep. 5, 2019, 18 pages.
Chugai Pharmaceutical, A Phase I, Multiple-dose Study of SA237, Study JapicCTI—No. 121786; submitted to Clinicaltrials.jp on Jan. 31, 2014; downloaded from clinicaltrials.jp archive on Sep. 5, 2019 as https://www .clinicaltrials.jp/cti -user/trial/Show .jsp, 5 pages.
Chugai Pharmaceutical, A phase I, Multiple-dose study of SA237, Study JapicCT—No. 121786; submitted to Clinicaltrials.jp on Jun. 19, 2012; downloaded from clinicaltrials.jp archive on Sep. 5, 2019 as https://www.clinicaltrials.jp/ctiuser/ trial/Show.jsp, 5 pages.
Chugai Pharmaceutical, A phase I, Multiple-Dose Study of SA237, Study JapicCTI—No. 121786; Submitted to Clinicaltrials.jp on Mar. 19, 2012; downloaded from clinicaltrials.jp archive on Sep. 5, 2019 as https://www.clinicaltrials.jp/cti-user/trial/Show.jsp, 5 pages.
Chugai Pharmaceutical, "Efficacy and Safety Study of Satralizumab (SA237) as Add-on Therapy to Treat Participants With Neuromyelitis Optica (NMO) and NMO Spectrum Disorder (NMOSD)," Study NCT02028884, Version 1, ClinicalTrials.gov, Jan. 6, 2014, accessed at https://clinicaltrials.gov/ct2/history/NCT02028884?V1= View#StudyPageTop, accessed on Sep. 4, 2019, 6 pages.
Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 2; submitted to ClinicalTrials.gov on Feb. 25, 2014; downloaded from ClinicalTrials.gov archive on Sep. 4, 2019 as https://clinicaltrials.gov/ct2/history/NCT02028884?V2=View#StudyPageTop, 6 pages.
Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 3; submitted to ClinicalTrials.gov on Sep. 4, 2015; downloaded from ClinicalTrials.gov archive on Sep. 4, 2019 as https://clinicaltrials.gov/ct2/history/NCT02028884?V3=View#StudyPageTop, 6 pages.
Chugai Pharmaceutical, "Efficacy and Safety Study of Satralizumab (SA237) as Add-on Therapy to Treat Participants With Neuromyelitis Optica (NMO) and NMO Spectrum Disorder (NMOSD)" Study NCT02028884, version 4, Submitted to ClinicalTrials.gov on Dec. 8, 2015; Downloaded from ClinicalTrials.gov archive on Sep. 4, 2019 as https://clinicaltrials.gov/ct2/history/NCT02028884?V4=View#StudyPageTop, 6 pages.
Chugai Pharmaceutical, "Efficacy and Safety Study of Satralizumab (SA237) as Monotherapy to Treat Participants With Neuromyelitis Optica (NMO) and Neuromyelitis Optica Spectrum Disorder (NMOSD)," Study NCT02073279, Version 1, ClinicalTrials.gov, Feb. 25, 2014, accessed at https://clinicaltrials.gov/ct2/history/NCT02073279?V1=View#StudyPageTop, accessed on Sep. 4, 2019, 6 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 10; submitted to ClinicalTrials.gov on Jul. 7, 2015; downloaded from ClinicalTrials.gov archive on Sep. 5, 2019 as https://clinicaltrials.gov/ct2/history/NCT02073279?V10=View#StudyPageTop, 9 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 11; submitted to ClinicalTrials.gov on Aug. 3, 2015; downloaded from ClinicalTrials.gov archive on Sep. 5, 2019 as https://clinicaltrials.gov/ct2/history/NCT02073279?V11=View#StudyPageTop, 10 pages.
Chugai Pharmaceutical, "Efficacy and Safety Study of Satralizumab (SA237) as Monotherapy to Treat Participants With Neuromyelitis Optica (NMO) and Neuromyelitis Optica Spectrum Disorder (NMOSD)", Study NCT02073279, version 12; submitted to ClinicalTrials.gov on Sep. 3, 2015; downloaded from ClinicalTrials.gov archive on Sep. 5, 2019 as https://clinicaltrials.gov/ct2/history/NCT02073279?V12=View#StudyPageTop, 10 pages.
Chugai Pharmaceutical, "Efficacy and Safety Study of Satralizumab (SA237) as Monotherapy to Treat Participants With Neuromyelitis Optica (NMO) and Neuromyelitis Optica Spectrum Disorder (NMOSD)," Study NCT02073279, Version 13, ClinicalTrials.gov, Oct. 5, 2015, acccessed at https://clinicaltrials.gov/ct2/history/NCT02073279?V13=View#StudyPageTop, accessed on Sep. 5, 2019, 10 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 14; submitted to ClinicalTrials.gov on Dec. 8, 2015; downloaded from ClinicalTrials.gov archive on Sep. 5, 2019 as https://clinicaltrials.gov/ct2/history/NCT02073279?V14=View#StudyPageTop, 10 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 2; submitted to ClinicalTrials.gov on Jul. 22, 2014; downloaded from ClinicalTrials.gov archive on Sep. 5, 2019 as https://clinicaltrials.gov /ct2/history/NCT02073279?V2= View#StudyPageTop, 6 pages.
Chugai Pharmaceutical, "Efficacy and Safety Study of Satralizumab (SA237) as Monotherapy to Treat Participants With Neuromyelitis Optica (NMO) and Neuromyelitis Optica Spectrum Disorder (NMOSD)", Study NCT02073279, version 3; submitted to ClinicalTrials.gov on Dec. 15, 2014; downloaded from ClinicalTrials.gov archive on Sep. 5, 2019 as https://clinicaltrials.gov /ct2/history/NCT02073279?V3= View#StudyPageTop, 7 pages.

(56) References Cited

OTHER PUBLICATIONS

Chugai Pharmaceutical, "Efficacy and Safety Study of Satralizumab (SA237) as Monotherapy to Treat Participants With Neuromyelitis Optica (NMO) and Neuromyelitis Optica Spectrum Disorder (NMOSD)", Study NCT02073279, Version 4; Submitted to ClinicalTrials.gov on Feb. 5, 2015; downloaded from ClinicalTrials.gov archive on Sep. 5, 2019 as https://clinicaltrials.gov/ct2/history/NCT02073279?V4=View#StudyPageTop, 8 pages.

Chugai Pharmaceutical, "Efficacy and Safety Study of Satralizumab (SA237) as Monotherapy to Treat Participants With Neuromyelitis Optica (NMO) and Neuromyelitis Optica Spectrum Disorder (NMOSD)," Study NCT02073279, Version 5, ClinicalTrials.gov, Feb. 6, 2015, accessed at https://clinicaltrials.gov/ct2/history/NCT02073279?V5=View#StudyPageTop, accessed on Sep. 5, 2019, 8 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 6; submitted to ClinicalTrials.gov on Mar. 4, 2015; downloaded from ClinicalTrials.gov archive on Sep. 5, 2019 as https://clinicaltrials.gov/ct2/history/NCT02073279?V6=View#StudyPageTop, 9 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 7; submitted to ClinicalTrials.gov on Apr. 1, 2015; downloaded from ClinicalTrials.gov archive on Sep. 5, 2019 as https://clinicaltrials.gov/ct2/history/NCT02073279?V7=View#StudyPageTop, 9 pages.

Chugai Pharmaceutical, "Efficacy and Safety Study of Satralizumab (SA237) as Monotherapy to Treat Participants With Neuromyelitis Optica (NMO) and Neuromyelitis Optica Spectrum Disorder (NMOSD)", Study NCT02073279, version 8; submitted to ClinicalTrials.gov on May 7, 2015; downloaded from ClinicalTrials.gov archive on Sep. 5, 2019 as https://clinicaltrials.gov/ct2/history/NCT02073279?V8=View#StudyPageTop, 9 pages.

Chugai Pharmaceutical, "Efficacy and Safety Study of Satralizumab (SA237) as Monotherapy to Treat Participants With Neuromyelitis Optica (NMO) and Neuromyelitis Optica Spectrum Disorder (NMOSD)," Study NCT02073279, Version 9, ClinicalTrials.gov, Jun. 5, 2015, accessed at https://clinicaltrials.gov/ct2/history/NCT02073279?V9=View#StudyPageTop, accessed on Sep. 5, 2019, 9 pages.

Clinical Trials, GlaxoSmithKline, "A Phase 2a Study to Evaluate the Effects of Sirukumab in Subjects With Severe Poorly Controlled Asthma," ClinicalTrials.gov, accessed at https://clinicaltrials.gov/ct2/show/NCT02794519, first posted on Jun. 9, 2016, ID: NCT02794519.

Chugai Seiyaku Kabushiki Kaisha, Presentation of the Results of the Phase III International Clinical Trial of Satralizumab in Neuromyelitis Optica Spectrum Disorder at the European Committee for Treatment and Research in Multiple Sclerosis (ECTRIMS), (Oct. 15, 2018) (with English translation).

Chung, Y.C., and Chang, Y.F.,"Serum Interleukin-6 Levels Reflect the Disease Status of Colorectal Cancer," Journal of Surgical Oncology 83(4): 222-226 (2003).

Chuntharapai, A and Kim, K.J., "Generation of Monoclonal Antibodies to Chemokine Receptors," Methods in Enzymology 288:15-27 (1997).

Cocco, M., et al., "In Vitro Generation of Long-Lived Human Plasma Cells", Journal of Immunology 189(12):5773-5785 (2012).

Cole, M.S., et al., "Human IgG2 Variants of Chimeric Anti-CD3 are Nonmitogenic to T Cells," Journal of Immunology 159(7):3613-3621 (1997).

Cordoba, A.J., et al., "Non-Enzymatic Hinge Region Fragmentation of Antibodies in Solution," Journal of Chromatography B 818(2):115-121 (2005).

Culig, Z., et al., "Interleukin-6 Regulates Androgen Receptor Activity and Prostate Cancer Cell Growth", Molecular and Cellular Endocrinology 197:231-238 (2002).

Damschroder, M.M., et al., "Framework Shuffling of Antibodies to Reduce Immunogenicity and Manipulate Functional and Biophysical Properties," Molecular Immunology 44(11):3049-3060 (2007).

Dangott, B., et al., "Dietary Creatine Monohydrate Supplementation Increases Satellite Cell Mitotic Activity During Compensatory Hypertrophy," International Journal of Sports Medicine 21(1):13-16 (2000).

Darr, K.C. and Schultz, E.,"Hindlimb Suspension Suppresses Muscle Growth and Satellite Cell Proliferation," Journal of Applied Physiology 67(5): 1827-1834 (1989).

Davies, G., et al., "The Hgf/sf Antagonist Nk4 Reverses Fibroblast- and Hgf-induced Prostate Tumor Growth and Angiogenesis in Vivo," International Journal of Cancer 106(3):348-354 (2003).

Davies, J., et al., "Affinity Improvement of Single Antibody VH Domains: Residues in All Three Hypervariable Regions Affect Antigen Binding", Immunotechnology 2:169-179 (1996).

De Pascalis, R., et al., "Grafting of "Abbreviated" Complementarity-Determining Regions Containing Specificity-Determining Residues Essential for Ligand Contact to Engineer a Less Immunogenic Humanized Monoclonal Antibody," Journal of Immunology 169(6):3076-3084 (2002).

De Vita, F., et al.,"Serum Levels of Interleukin-6 as a Prognostic Factor in Advanced Non-small Cell Lung Cancer," Oncology Reports 5(3): 649-652 (1998).

Demir, I.E., et al.,"Nerve-cancer Interactions in the Stromal Biology of Pancreatic Cancer," Frontiers in Physiology 3:97 (2012).

Dillon, T.M., et al., "Structural and Functional Characterization of Disulfide Isoforms of the Human IgG2 Subclass," The Journal of Biological Chemistry 283(23):16206-16215 (2008).

Ding, W., et al., "The Change of Plasma Interleukin-6 Level and Cardiac Protective Effect of Monoclonal Antibody to IL-6 During Myocardial Infarction Reperfusion," Chinese Journal of Cardiology 27(1):29-32, (1998) (with English Abstract).

Doerks, T., et al.,"Protein Annotation: Detective Work for Function Prediction," Trends in Genetics 14(6): 248-250 (1998).

Doganci, A., et al., "The IL-6R Alpha Chain Controls Lung CD4+ CD25+ Treg Development and Function During Allergic Airway Inflammation in Vivo," The Journal of Clinical Investigation 115(2):313-325 (2005).

Duluc, D., et al., "Tumor-associated Leukemia Inhibitory Factor and Il-6 Skew Monocyte Differentiation Into Tumor-associated Macrophage-like Cells", Blood 110:4319-4330 (2007).

Ebos, J. M. L., et al., "Accelerated Metastasis after Short-Term Treatment with a Potent Inhibitor of Tumor Angiogenesis," Cancer Cell 15(3):232-239 (2009).

Eder, I.E., et al.,"Targeting the Androgen Receptor in Hormone-refractory Prostate Cancer—new Concepts," Future Oncology 1(1): 93-101 (2005).

Esty, B., et al., "346: Anti-IL-6 Treatment in Two Pediatric Patients with Severe Persistent Asthma with the IL4R576 Variant," The AAAAI/WAO Joint Congress, accessed at https://aaaai.confex.com/aaaai/wao18/webprogram/Paper34378.html, accessed on Mar. 4, 2018.

Ewert, S., et al., "Stability Improvement of Antibodies for Extracellular and Intracellular Applications: CDR Grafting to Stable Frameworks and Structure-based Framework Engineering," Methods (San Diego, Calif.), 34(2):184-199 (2004).

F. Hoffmann-La Roche Ltd., "A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD)," Study EudraCT 2013-003752-21 in Germany; submitted to clinicaltrialsregister.eu on Dec. 20, 2013; downloaded from clinicaltrialsregister.eu archive on Sep. 5, 2019 as https://www.clinicaltrialsregister.eu/ctr-searchltrial/2013-003752-21/DE, 7 pages.

F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Hungary; submitted to clinicaltrialsregister.eu on Feb. 25, 2015; downloaded from clinicaltrialsregister.eu archive on Sep. 5, 2019 ashttps://www.clinicaltrialsregister.eu/ctr-search/trial/2013-003752-21/HU, 6 pages.

(56) References Cited

OTHER PUBLICATIONS

F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Italy; submitted to clinicaltrialsregister.eu on Feb. 6, 2014; downloaded from clinicaltrialsregister.eu archive on Sep. 5, 2019 as https://www.clinicaltrialsregister.eu/ctr-search/trial/2013-003752-21/IT, 5 pages.

F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Poland; submitted to clinicaltrialsregister.eu on Jul. 4, 2014; downloaded from clinicaltrialsregister.eu archive on Sep. 5, 2019 ashttps://www.clinicaltrialsregister.eu/ctr-search/trial/2013-003752-21/GB, 7 pages.

F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Poland; submitted to clinicaltrialsregister.eu on Oct. 15, 2013; downloaded from clinicaltrialsregister.eu archive on Sep. 5, 2019 as https://www.clinicaltrialsregister.eu/ctr-search/trial/2013-003752-21/PL, 7 pages.

F. Hoffmann-La Roche Ltd., "A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD)," Study EudraCT 2013-003752-21 in Spain; submitted to clinicaltrialsregister.eu on Mar. 11, 2015; downloaded from clinicaltrialsregister.eu archive on Sep. 5, 2019 as https://www.clinicaltrialsregister.eu/ctr-search/trial/2013-003752-21/ES, 7 pages.

F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in the United Kingdom; submitted to clinicaltrialsregister.eu on Oct. 15, 2013; downloaded from clinicaltrialsregister.eu archive on Sep. 5, 2019 ashttps://www.clinicaltrialsregister.eu/ctr-search/trial/2013-003752-21/GB, 6 pages.

F. Hoffmann-La Roche Ltd., "A Multicenter, Randomized, Addition to Baseline Treatment, Double-blind, Placebo-controlled, Phase 3 Study to Evaluate the Efficacy and Safety of Satralizumab (SA237) in Patients With Neuromyelitis Optica (NMO) and NMO Spectrum Disorder (NMOSD)," Study EudraCT 2013-003752-21, Italy, clinicaltrialsregister.eu, Feb. 6, 2014, accessed at https://www.clinicaltrialsregister.eu/ctr-search/trial/2013-003752-21/IT, accessed on Sep. 5, 2019, 5 pages.

F. Hoffmann-La Roche Ltd., "A Multicenter, Randomized, Double-blind, Placebo-controlled, Phase 3 Study to Evaluate the Efficacy and Safety of Satralizumab (SA237) as Monotherapy in Patients With Neuromyelitis Optica (NMO) and Neuromyelitis Optica Spectrum Disorder (NMOSD)," Study EudraCT 2015-005431-41 in Croatia; submitted to clinicaltrialsregister.eu on Dec. 15, 2016; downloaded from clinicaltrialsregister.eu archive on Sep. 5, 2019 as https://www.clinicaltrialsregister.eu/ctr-search!trial/2015-005431-41/HR, 6 pages.

F. Hoffmann-La Roche Ltd., "A Multicenter, Randomized, Double-blind, Placebo-controlled, Phase 3 Study to Evaluate the Efficacy and Safety of Satralizumab (SA237) as Monotherapy in Patients With Neuromyelitis Optica (NMO) and Neuromyelitis Optica Spectrum Disorder (NMOSD)," Study EudraCT 2015-005431-41, Poland, clinicaltrialsregister.eu, Apr. 7, 2016; accessed on Sep. 5, 2019, 6 pages.

F. Hoffmann-La Roche Ltd., "Efficacy and Safety Study of Satralizumab (SA237) as Add-on Therapy to Treat Participants With Neuromyelitis Optica (NMO) and NMO Spectrum Disorder (NMOSD)," Study NCT02028884, first posted on clinicaltrialsregister.eu on Jan. 7, 2014 and last updated on Apr. 13, 2021; downloaded from clinicaltrialsregister.eu archive on May 19, 2021, https://clinicaltrials.gov/ct2/show/NCT02028884.

F. Hoffmann-La Roche Ltd., "Efficacy and Safety Study of Satralizumab (SA237) as Monotherapy to Treat Participants With Neuromyelitis Optica (NMO) and Neuromyelitis Optica Spectrum Disorder (NMOSD)," Study NCT02073279, first posted on clinicaltrialsregister.eu on Feb. 27, 2014 and last updated on Mar. 24, 2021; downloaded from clinicaltrialsregister.eu archive on May 19, 2021.

Finkel, M.S., et al., "Negative Inotropic Effects of Cytokines on the Heart Mediated by Nitric Oxide," Science 257(5068):387-389 (1992).

Fisniku, O., et al., "Protective Effects of PG490-88 on Chronic Allograft Rejection by Changing Intragraft Gene Expression Profiles," Transplantation Proceedings 37:1962-1964 (2005).

Ford, H.R., et al., "Evidence that Production of Interleukin 6 within the Rejecting Allograft Coincides with Cytotoxic T Lymphocyte Development," Transplantation 51 (3):656-661 (1991).

Fraunberger, P., et al., "Cytokine and Cytokine-receptor Profiles After Liver and Heart Transplantation," Transplantation Proceedings 27(3):2023-2027 (1995).

Fredj, S., et al., "Role of Interleukin-6 in Cardiomyocyte/Cardiac Fibroblast Interactions During Myocyte Hypertrophy and Fibroblast Proliferation", Journal of Cellular Physiology 204:428-436 (2005).

Fuchs, M., et al., "Role of Interleukin-6 for LV Remodeling and Survival After Experimental Myocardial Infarction," FASEB Journal 17(14):2118-2120 (2003).

Fujita, J., et al.,"Anti-interleukin-6 Receptor Antibody Prevents Muscle Atrophy in Colon-26 Adenocarcinoma-bearing Mice With Modulation of Lysosomal and Atp-ubiquitin-dependent Proteolytic Pathways," International Journal of Cancer 68(5): 637-643 (1996).

Fujiwara, et al., "Control of Tumor Immunity by B Cells and Th2 Cytokines," Annual Reviews 257-269 (1999) (with an unverified English translation).

Furukawa, Y., et al., "Cytokine Gene Expression During the Development of Graft Coronary Artery Disease in Mice", Japanese Circulation Journal 63:775-782 (1999).

Gao, S. P., et al.."Mutations in the EGFR Kinase Domain Mediate STAT3 Activation via IL-6 Production in Human Lung Adenocarcinomas," The Journal of Clinical Investigation 117(12): 3846-3856 (2007).

Garry, D.J., et al., "Myogenic Stem Cell Function is Impaired in Mice Lacking the Forkhead/winged Helix Protein MNF," PNAS 97(10):5416-5421 (2000).

Garry, D.J., et al., "Persistent Expression of MNF Identifies Myogenic Stem Cells in Postnatal Muscles," Developmental Biology 188:280-294 (1997).

Gastroenterology, Digestive Disease Week Meeting 2006/107th Annual Meeting of the American Gastroenterological Association, 130(4) Suppl 2, 750A (May 2006).

Gessner, J.E., et al., "The IgG Fc Receptor Family," Annals of Hematology 76(6):231-248 (1998).

Ghetie, V., et al., "Increasing the Serum Persistence of an IgG Fragment by Random Mutagenesis," Nature Biotechnology 15(7):637-640 (1997).

Ghosh, S. and Karin, M., "Missing Pieces in the NF-KB Puzzle," Cell 109:S81-S96 (2002).

Giugliano, G., et al., "Verapamil Inhibits Interleukin-6 and Vascular Endothelial Growth Factor Production in Primary Cultures of Keloid Fibroblasts," British Journal of Plastic Surgery 56(8):804-809 (2003).

Greenberg, A.S., et al.,"Interleukin 6 Reduces Lipoprotein Lipase Activity in Adipose Tissue of Mice in Vivo and in 3t3-I1 Adipocytes: a Possible Role for Interleukin 6 in Cancer Cachexia," Cancer Research 52(15): 4113-4116 (1992).

Greten, F.R., et al., "IKKbeta Links Inflammation and Tumorigenesis in a Mouse Model of Colitis-associated Cancer," Cell 118(3):285-296 (2004).

Grossniklaus, H.E. and Green, W.R., "Choroidal Neovascularization," American Journal of Ophthalmology 137:496-503 (2004).

Guerne, P.A., et al., "Synovium as a Source of Interleukin 6 in Vitro. Contribution to Local and Systemic Manifestations of Arthritis," The Journal of Clinical Investigation 83(2):585-592 (1989).

(56) References Cited

OTHER PUBLICATIONS

Guice, K.S., et al.,"Anti-tumor Necrosis Factor Antibody Augments Edema Formation in Caerulein-induced Acute Pancreatitis," The Journal of Surgical Research 51(6): 495-499 (1991).
Guillen, I., et al., "Cytokine Signaling During Myocardial Infarction: Sequential Appearance of IL-1 Beta and IL-6," The American Journal of Physiology 269(2 Pt 2):R229-R235 (1995).
Guyre, P.M., et al., "Increased Potency of Fc-Receptor-Targeted Antigens," Cancer Immunology 45(3-4):146-148 (1997).
Gwechenberger, M., et al., "Cardiac Myocytes Product Interleukin-6 in Culture and in Viable Border Zone of Reperfused Infarctions", Circulation 99:546-551 (1999).
Hanahan, D and Weinberg, R.A., "Hallmarks of Cancer: the Next Generation," Cell 144(5):646-674 (2011).
Hanes, J., et al., "Picomolar Affinity Antibodies From a Fully Synthetic Naive Library Selected and Evolved by Ribosome Display," Nature Biotechnology 18(12):1287-1292 (2000).
Hatzi, E., et al., "N-myc Oncogene Overexpression Down-Regulates IL-6; Evidence that IL-6 Inhibits Angiogenesis and Suppresses Neuroblastoma Tumor Growth", Oncogene 21:3552-3561 (2002).
Hinton, P.R., et al., "An Engineered Human IgG1 Antibody With Longer Serum Half-life," Journal of Immunology 176(1):346-356 (2006).
Hirai, I., et al., "Perineural Invasion in Pancreatic Cancer," Pancreas 24(1):15-25 (2002).
Hirano et al., "Complementary DNA for a novel human interleukin (BSF-2) that induces Blymphocytes to produce immunoglobulin," Nature 324: 73-76 (1986).
Hirano, T., et al., "Excessive Production of Interleukin 6/b Cell Stimulatory Factor-2 in Rheumatoid Arthritis," European Journal of Immunology 18(11):1797-1801 (1988).
Hirata, Y., et al., "Characterization of IL-6 Receptor Expression by Monoclonal and Polyclonal Antibodies", Journal of Immunology 143:2900-2906 (1989).
Hirota, H., et al., "Loss of a gp130 Cardiac Muscle Cell Survival Pathway is a Critical Event in the Onset of Heart Failure During Biomechanical Stress," Cell 97:189-198 (1999).
Hirota, H., et al., "Continuous Activation of gp130, a Signal-transducing Receptor Component for Interleukin 6-related Cytokines, Causes Myocardial Hypertrophy in Mice," PNAS 92(11):4862-4826 (1995).
Hisanaga, K., "Neuro-Behcet Disease and Neuro-Sweet Disease," Clinical Neurology 52(11):1234-1236 (2012) (with English Abstract).
Hocking, D.C., et al., "Mechanisms of Pulmonary Edema Induced by Tumor Necrosis Factor-α," Circulation Research 67:68-77 (1990).
Hoffmann, S., et al., "Inhibitory Effects of Verapamil Isomers on the Proliferation of Choroidal Endothelial Cells," Graefe's archive for clinical and experimental ophthalmology 244(3):376-381 (2006).
Holt, L.J., et al., "Domain Antibodies: Proteins for Therapy", Trends in Biotechnology 21:484-490 (2003).
Hong, D. S., et al.,"Interleukin-6 and Its Receptor in Cancer," Cancer 110:1911-1928 (2007).
Horinaga, M., et al., "Clinical and Pathologic Significance of Activation of Signal Transducer and Activator of Transcription 3 in Prostate Cancer," Urology 66:671-675 (2005).
Hornick, P. and Rose, M., "Chronic Rejection in the Heart," Methods in Molecular Biology 333:131-144 (2006).
Hosokawa, T., et al., "The Response to Treatment with Interferon Beta-lb in Patients with Multiple Sclerosis," Shinkei Chiryo 25:589-595 (2008) (English translation).
Houssiau, F.A., et al., "Interleukin-6 in Synovial Fluid and Serum of Patients With Rheumatoid Arthritis and Other Inflammatory Arthritides," Arthritis and Rheumatism 31(6):784-788 (1988).
Houzen, H., et al., "Increased Prevalence, Incidence, and Female Predominance of Multiple Sclerosis in Northern Japan," Journal of the Neurological Sciences 15:323(1-2):117-122 (2012).
Huang, C., et al., "Inhibition of STAT3 Activity with AG490 Decreases the Invasion of Human Pancreatic Cancer Cells in Vitro", Cancer Science 97:1417-1423 (2006).

Huang, C., et al., "Inhibitory Effect of AG490 on Invasion and Metastasis of Human Pancreatic Cancer Cells in Vitro," Chinese Journal of Oncology 28(12):890-892 (2006).
Huang, Y.W. and Vitetta, E.S., "A Monoclonal Anti-Human IL-6 Receptor Antibody Inhibits the Proliferation of Human Myeloma Cells," Hybridoma 12(5):621-630 (1993).
Hudes et al., "Preliminary Results of a Phase I Study: A Chimeric Monoclonal Anti IL-6 Antibody CNTO 328 in Combination with Docetaxel in Patients with Hormone Refractory Prostate Cancer," Journal of Clinical Oncology 25:18S (2007).
Huizinga, T.W., et al., "Sarilumab, A Fully Human Monoclonal Antibody Against IL-6Rα in Patients with Rheumatoid Arthritis and an Inadequate Response to Methotrexate: Efficacy and Safety Results from the Randomised SARIL-RA-MOBILITY Part A Trial", Annals of the Rheumatic Diseases 73:1626-1634 (2014).
Hwang, W.Y., et al., "Use of Human Germline Genes in a CDR Homology-based Approach to Antibody Humanization," Methods (San Diego, Calif.) 36(1):35-42 (2005).
Idezawa, T., et al., "Interleukin-6 Functions as An Autocrine Invasion Factor of Human Pancreatic Cancer Cells," Yamanashi Medical Journal 19(2):53-67 (2004).
Idezawa, T., et al., "Interleukin-6 Functions as An Autocrine Invasion Factor of Human Pancreatic Cancer Cells," Yamanashi Medical Journal 20(2):xxxvi (2005).
Ishikawa, S., et al., Annals of the Rheumatic Diseases, 65(Suppl 2):474 (2006).
Ito, et al., Journal of Japan Surgical Society 107 (special extra issue 2):387, PS-014-5 (2006) (English translation included).
Ito, N., et al., "Induction of Interleukin-6 by Interferon Alfa and Its Abrogation by a Serine Protease Inhibitor in Patients with Chronic Hepatitis C," Hepatology 23(4):669-675 (1996).
Ito, W., et al., "The His-Probe Method: Effects of Histidine Residues Introduced into the Complementarity-Determining Regions of Antibodies on Antigen-Antibody Interactions at Different pH Values," FEBS Letters 309(1):85-88 (1992).
Itoh, et al., "Anti-IL-6 Receptor Antibody Down-Regulates Pro-Inflammation Cytokine Production of Gr-1 *CD11b* Cells and Prevents Early Loss ofIslet Grafts in the Liver of Mice in Association with Engraftments," Transplantation, 82(Supp. 3), World Transplant Congress, Abstract No. 2838 (2006).
Izawa, A., et al., "Critical Role of Interleukin-6 and its Crosstalk with AT1 R Signaling in Acute Rejection of Murine Cardiac Allografts," Circulation Journal 71 (Suppl. 1 ):392 (#PE-269) (2007).
Izawa, A., et al., "Interleukin-6 Blockade Attenuates the Development of Both Acute and Chronic Rejection of Murine Cardiac Allografts: A Potential Crosstalk between Interleukin-6 and Signaling through Angiotensin II Type 1 Receptor," American Journal of Transplantation 7 (Suppl. 11):426 (#1084) (2007).
Jacob, A., et al., "Detrimental Role of Granulocyte-colony Stimulating Factor in Neuromyelitis Optica: Clinical Case and Histological Evidence," Multiple Sclerosis 18:1801-1803 (2012).
Japanese Society of Neurological Therapeutics, "Standard Neurological Therapeutics: Neuromyelitis Optica (NMO)," 30(6):777-794, (2003) (including a partial English translation).
Jego, G., et al., "Interleukin-6 is a Growth Factor for Nonmalignant Human Plasmablasts," Blood 97(6):1817-1822 (2001).
Jejurikar et al., "Skeletal Muscle Denervation Increases Satellite Cell Susceptibility to Apoptosis," Plastic and Reconstructive Surgery 110:160-168 (2002).
Jeron, A., et al., "Systemic Immunosuppression Fails to Suppress Cardiac Cytokine Induction in Pressure Overload Hypertrophy in Rats," Immunobiology 205(1):51-60 (2002).
Johnson, K.A., et al., "Cation Exchange-HPLC and Mass Spectrometry Reveal C-Terminal Amidation of an IgG1 Heavy Chain," Analytical Biochemistry 360(1):75-83 (2007).
Jones, S.W., et al., "Disuse Atrophy and Exercise Rehabilitation in Humans Profoundly Affects the Expression of Genes Associated with the Regulation of Skeletal Muscle Mass," FASEB Journal 18(9):1025-1027 (2004).
Jones, T.D., et al., "Identification and Removal of a Promiscuous CD4+ T Cell Epitope From the C1 Domain of Factor VIII," Journal of Thrombosis and Haemostasis 3(5):991-1000 (2005).

(56) References Cited

OTHER PUBLICATIONS

Jourdan, M., et al., "An in Vitro Model of Differentiation of Memory B Cells Into Plasmablasts and Plasma Cells Including Detailed Phenotypic and Molecular Characterization", Blood 114:5173-5181 (2009).

Kakuron III, "Section 9 Opticospinal Multiple Sclerosis," Tahatsusei Kokasho Chiryo Guideline, Societas Neurologica Japonica, 2010:104-109 (2010).

Kallen, K.-J., et al., "New Developments in Il-6 Dependent Biology and Therapy: Where Do We Stand and What Are the Options?," Expert Opinion on Investigational Drugs 8:1327-1349 (1999).

Kami, K., et al., "Gene Expression of Receptors for IL-6, LIF, and CNTF in Regenerating Skeletal Muscles", Journal of Histochemistry and Cytochemistry 48:1203-1213 (2000).

Kamohara et al., "IL-6 no Suigan Saibo no Zoshoku-Ten'i Oyobosu Eikyo to Kanshitsu Saibo ni yoru Hatsugen Seigyo Kika," Japanese Journal of Gastroenterological Surgery 39(7):1356 (Abstract 2529) (2006).

Kampan, N.C., et al., "Immunotherapeutic Interleukin-6 or Interleukin-6 Receptor Blockade in Cancer: Challenges and Opportunities," Current Medicinal Chemistry 25(36):4785-4806 (2018).

Kan, S., et al., "The Effect of Anti-Cancer Agents on CD4+FoxP3+ Regulatory T Cell," Dai 68 Kai Annual Meeting of the Japan Cancer Association, p. 286, P-0539 (2009).

Kanda, T. and Takahashi, T., "Interleukin-6 and Cardiovascular Diseases," Japanese Heart Journal 45(2):183-193 (2004).

Karin, M. and Lin, A., "NF-KB at the Crossroads of Life and Death", Nature Immunology 3:221-227 (2002).

Karin, M., et al., "NF-kappaB In Cancer: From Innocent Bystander to Major Culprit," Nature Reviews Cancer 2(4):301-310 (2002).

Kato, "A Case of Bronchial Asthma Where IL-6 is Considered to Have Been Involved in Making It Refractory," Shindan To Chiryo, 106(10):1287-1291 (2018).

Kayahara et al., "The Nature of Neural Invasion by Pancreatic Cancer," Pancreas 35:218-223 (2007).

Kayahara, M., et al., "Neural Invasion and Lymph Node Metastasis in the Head of the Pancreas Carcinoma," The Japanese Journal of Gastroenterological Surgery 24(3):813-817 (1991).

Kim, S., et al., "Carcinoma-Produced Factors Activate Myeloid Cells Through TLR2 to Stimulate Metastasis," Nature 457(7225):102-106 (2009).

Kim, S.J., et al., "Antibody Engineering for the Development of Therapeutic Antibodies," Molecules and Cells 20(1):17-29 (2005).

Kishimoto, T., "The Biology of Interleukin-6," Blood 74(1):1-10 (1989).

Kitahara, M., et al., "The in Vivo Anti-Tumor Effect of Human Recombinant Interleukin-6", Japanese Journal of Cancer Research 81:1032-1038 (1990).

Kitazawa, R., et al., "Interleukin-1 Receptor Antagonist and Tumor Necrosis Factor Binding Protein Decrease Osteoclast Formation and Bone Resorption in Ovariectomized Mice," The Journal of Clinical Investigation 94(6):2397-2406 (1994).

Klein, B., et al., "Interleukin-6 in Human Multiple Myeloma," Blood 85(4): 863-872 (1995).

Knulst, A.C., et al., "Cytokine Detection and Modulation in Acute Graft vs. Host Disease in Mice," Mediators of Inflammation 3(1):33-40 (1994).

Kobara, M., et al., "Antibody Against Interleukin-6 Receptor Attenuates Left Ventricular Remodelling After Myocardial Infarction in Mice," Cardiovascular Research 87:424-430 (2010).

Kobara, M., et al., "Inhibition of Interleukin-6 Signaling Attenuates Left Ventricular Remodeling After Myocardian Infarction in Mice," Journal of the American Heart Association 112(851) (2005).

Kobatake, K., et al., "Kdm6a Deficiency Activates Inflammatory Pathways, Promotes M2 Macrophage Polarization, and Causes Bladder Cancer in Cooperation with p53 Dysfunction," Clinical Cancer Research 26(8):2065-2079 (2020).

Koch, S., et al., "IL-6 activated integrated BATF/IRF4 functions in lymphocytes are T-bet-independent and reversed by subcutaneous immunotherapy," Scientific Reports 3(1754):1-9 (2013).

Koide, N., et al., "Establishment of Perineural Invasion Models and Analysis of Gene Expression Revealed an Invariant Chain (CD74) as a Possible Molecule Involved in Perineural Invasion in Pancreatic Cancer," Clinical Cancer Research 12(8):2419-2426 (2006).

Konopatskaya et al., Molecular Vision, Monday, May 1, 2006, 11:15 AM-1:00PM Hall B/C Poster Session Program Number/Board# Range: 1749-1764/B836-B851, 244. Antiangiogenesis: Basic Mechanisms.

Kotake et al., "Interleukin-6 and Soluble Interleukin-6 Receptors in the Synovial Fluids From Rheumatoid Arthritis Patients Are Responsible for Osteoclast-like Cell Formation," Journal of Bone and Mineral Research, 11(1):88-95 (1996).

Krieckaert, C.L., et al., "Immunogenicity of Biologic Therapies—We Need Tolerance," Nature Reviews. Rheumatology 6:558-559 (2010).

Kurdi, M., et al., "Increased Expression of IL-6 and LIF in the Hypertrophied Left Ventricle of TGR(mRen2)27 and SHR rats," Molecular and Cellular Biochemistry 269(1-2):95-101 (2005).

Kurek, J.B., et al., "The Role of Leukemia Inhibitory Factor in Skeletal Muscle Regeneration," Muscle Nerve 20:815-822 (1997).

Kurek, J.B., et al., "Up-regulation of Leukaemia Inhibitory Factor and Interleukin-6 in Transected Sciatic Nerve and Muscle Following Denervation," Neuromuscular Disorders 6(2):105-114 (1996).

Kuroda, K., et al., "Prevention of Cancer Cachexia by a Novel Nuclear Factor kB Inhibitor in Prostate Cancer," Clinical Cancer Research 11(15):5590-5594 (2005).

Latulippe, E., et al., "Comprehensive Gene Expression Analysis of Prostate Cancer Reveals Distinct Transcriptional Programs Associated with Metastatic Disease," Cancer Research 62:4499-4506 (2002).

Lancaster, J.M., et al., "Identification of Genes Associated with Ovarian Cancer Metastasis Using Microarray Expression Analysis," International Journal of Gynecological Cancer 16(5):1733-1745 (2006).

Lechner, M.G., et al., "Characterization of Cytokine-Induced Myeloid-Derived Suppressor Cells from Normal Human Peripheral Blood Mononuclear Cells," Journal of Immunology 185:2273-2284 (2010).

Lee, S.O., et al., "Interleukin-6 Protects LNCaP Cells From Apoptosis Induced by Androgen Deprivation Through the Stat3 Pathway," The Prostate 60(3):178-186 (2004).

Ler, L.D., et al., "Loss of Tumor Suppressor KDM6A Amplifies PRC2-Regulated Transcriptional Repression in Bladder Cancer and Can be Targeted Through Inhibition of EZH2," Science Translational Medicine 9(378):eaai8312 (2017).

Li, T., et al., "Phase II Study of the Proteasome Inhibitor Bortezomib (PS-341, Velcade®) in Chemotherapy-Naive Patients with Advanced Stage in Non-Small Cell Lung Cancer (NSCLC)," Lung Cancer 68:89-93 (2010).

Lin, Y.L., et al., "Critical Role of IL-6 in Dendritic Cell-Induced Allergic Inflammation of Asthma," Journal of Molecular Medicine 94(1):51-59 (2016).

Lotz, M., et al., "B Cell Stimulating Factor 2/interleukin 6 is a Costimulant for Human Thymocytes and T Lymphocytes," Journal of Experimental Medicine 167:1253-1258 (1988).

Lucchinetti, C., et al., "Heterogeneity of Multiple Sclerosis Lesions: Implications for the Pathogenesis of Demyelination," Annals of Neurology 47(6):707-717 (2000).

Luo, H., et al., "A Proteasome Inhibitor Effectively Prevents Mouse Heart Allograft Rejection," Transplantation 72(2):196-202 (2001).

Maccallum, R.M., et al., "Antibody-antigen Interactions: Contact Analysis and Binding Site Topography," Journal of Molecular Biology 262(5):732-745 (1996).

Madhok, R., et al., "Serum Interleukin 6 Levels in Rheumatoid Arthritis: Correlations With Clinical and Laboratory Indices of Disease Activity," Annals of the Rheumatic Diseases 52(3):232-234 (1993).

Maeda et al., "IKKBeta Couples Hepatocyte Death to Cytokine-driven Compensatory Proliferation That Promotes Chemical Hepatocarcinogenesis," Cell 121:977-990 (2005).

Maeda, et al., "Role of iKKbeta I NF-KB Activation for Development of Liver Metastasis," Supplement: The 58th Annual Meeting of the American Association for the Study of Liver Diseases,

(56) References Cited

OTHER PUBLICATIONS

Hepatol., 46:Issue Supplement SI, AASLD Abstracts, p. 518A, abstract No. 630, AASLD (2007).
Maeda, S., et al., "Ikappa B Kinasebeta/nuclear Factor-kappaB Activation Controls the Development of Liver Metastasis by Way of Interleukin-6 Expression," Hepatology 50:1851-1860 (2009).
Maini, R.N., et al., "Double-blind Randomized Controlled Clinical Trial of the Interleukin-6 Receptor Antagonist, Tocilizumab, in European Patients With Rheumatoid Arthritis Who Had an Incomplete Response to Methotrexate," Arthritis and Rheumatism 54(9):2817-2829 (2006).
Märten, A., et al., "Bortezomib is Ineffective in an Orthotopic Mouse Model of Pancreatic Adenocarcinoma," Molecular Cancer Therapeutics 7:3624-3631 (2008).
Martignoni, M.E., et al., "Role of Mononuclear Cells and Inflammatory Cytokines in Pancreatic Cancer-related Cachexia," Clinical Cancer Research 11(16):5802-5808 (2005).
Massoud, A. H., et al., "An asthma-associated IL4R variant exacerbates airway inflammation by promoting conversion of regulatory T cells to TH17-like cells," Nature Medicine 22(9):1013-1022 (2016).
Masui, T., et al., "Expression of IL-6 Receptor in Pancreatic Cancer: Involvement in VEGF Induction," Anticancer Research 22:4093-4100 (2002).
Matsuda, T., et al., "Establishment of an Interleukin 6 (IL 6)/B Cell Stimulatory Factor 2-Dependent Cell Line and Preparation of Anti-IL 6 Monoclonal Antibodies," European Journal of Immunology 18:951-956 (1988).
Matsumoto, M., et al., "Interleukin-10-Producing Plasmablasts Exert Regulatory Function in Autoimmune Inflammation," Immunity 41(6):1040-1051 (2014).
Matsushita et al., "Interleukin-6 soluble Interleukin-6 Receptor Complex Reduces Infarct Size via Inhibiting Myocardial Apoptosis," Laboratory Investigation 85:1210-1223 (2005).
Matzaraki, V., et al., "Evaluation of Serum Procalcitonin and Interleukin-6 Levels as Markers of Liver Metastasis," Clinical Biochemistry 40(5-6):336-342 (2007).
Mauro, A., "Satellite Cell of Skeletal Muscle Fibers," Journal of Biophysical and Biochemical Cytology 9:493-495 (1961).
Maynard et al., "Antibody Engineering," Annual Review of Biomedical Engineering 2:339-76 (2000).
McCormick, K.M. and Schultz, E., "Role of Satellite Cells in Altering Myosin Expression During Avian Skeletal Muscle Hypertrophy," Developmental Dynamics 199(1):52-63 (1994).
Meng, F., et al., "Acquired Resistance To Chemotherapy in Human Cholangiocarcinoma Is Mediated By An Interleukin (il-6) Dependent Activation of the X-Linked Inhibitor of Apoptosis (xiap) Protein," Gastroenterology 128(4):Supplemental 2:A-30, Abstract No. 165 (2005).
Meng, F., et al., "Over-expression of Interleukin-6 Enhances Cell Survival and Transformed Cell Growth in Human Malignant Cholangiocytes," Journal of Hepatology 44:1055-1065 (2006).
Michalaki, V., et al., "Serum Levels of IL-6 and TNF-a Correlate with Clinicopathological Features and Patient Survival in Patients with Prostate Cancer," British Journal of Cancer 90:2312-2316 (2004), article corrected—British Journal of Cancer 91(6):1227 (2004).
Mihara, M., et al., "Tocilizumab Inhibits Signal Transduction Mediated by both mIL-6R and sIL-6R, but not by the Receptors of Other Members of IL-6 Cytokine Family," Int. Immunopharmacol 5:1731-1740 (2005).
Miller, D.H., et al., "Differential Diagnosis of Suspected Multiple Sclerosis: A Consensus Approach," Multiple Sclerosis 14(9):1157-1174 (2008).
Ming, J. E., et al., "IL-6 Enhances the Generation of Cytolytic T Lymphocytes in the Allogeneic Mixed Leucocyte Reaction," Clinical and Experimental Immunology 89(1):148-153 (1992).
Mitsunaga, S., et al., "Detail Histologic Analysis of Nerve Plexus Invasion in Invasive Ductal Carcinoma of the Pancreas and Its Prognostic Impact," The American Journal of Surgical Pathology 31(11):1636-1644 (2007).
Mitsunaga, S., et al., "Nerve Invasion Distance is Dependent on Laminin gamma2 in Tumors of Pancreatic Cancer," International Journal of Cancer 127:805-819 (2010).
Miyamoto, Y., et al., "Interleukin-6 Inhibits Radiation Induced Apoptosis in Pancreatic Cancer Cells," Anticancer Research 21(4A):2449-2456 (2001).
Moss, F.P. and Leblond, C.P., "Satellite Cells as the Source of Nuclei in Muscles of Growing Rats," The Anatomical Record 170:421-435 (1971).
Mozdziak et al., "Hindlimb Suspension Reduces Muscle Regeneration," Journal of Applied Physiology, 78:136-140 (1998).
Mozdziak, P.E., et al., "Muscle Regeneration During Hindlimb Unloading Results in a Reduction in Muscle Size After Reloading," Journal of Applied Physiology 91(1):183-190 (2001).
Mozdziak, P.E., et al., "Quantitation of Satellite Cell Proliferation in Vivo Using Image Analysis," Biotech. Histochem 69:249-252 (1994).
Mozdziak, P.E., et al., "Unloading of Juvenile Muscle Results in a Reduced Muscle Size 9 wk After Reloading," Journal of Applied Physiology 88(1):158-164 (2000).
Mukaida et al., "Cytokines and Immune Network," Rinsho Kensa 35:447-452 (1991).
Mulhearn, B., et al., "Using the Immunophenotype to Predict Response to Biologic Drugs in Rheumatoid Arthritis," J Pers Med. 9(4):46 (2019).
Murata, et al., "Development Mechanism and Pathophysiology," Saishin-Igaku 47:49-56 (1992).
Murphy, R., "The effect of mechanical stretch on proliferation and differentiation ofC2C12 cells," FASEBJ, 18:A743 (Abstract#476.6) (2004).
Nagai, et al., "Suppression of Experimental Choroid Neovascularization by Inhibition ofInterleukin-6 Receptor," Inflammation and Regeneration 26:367 (#90) (2006) (English translation included).
Nakamura, et al., "Clinical Features of Multiple Sclerosis With High Plasmablast Frequency in Peripheral Blood," A Poster Session of 54th Annual Meeting of the Japanese Society of Neurology presented Jun. 1, 2013.
Nakamura, et al., "Clinical Characteristics of Multiple Sclerosis With High Plasmablast Frequency in Peripheral Blood," A Meeting Abstract of 54th Annual Meeting of the Japanese Society of Neurology, published Apr. 30, 2013.
Nakamura, et al., "Clinical features of multiple sclerosis with high plasmablast frequency in peripheral blood" poster session of Multiple Sclerosis by Keystone Symposia of Molecular and Cellular Biology, Big Sky, Montana, presented Jan. 14, 2013.
Nakamura, et al., "Clinical Features of Multiple Sclerosis With High Plasmablast Frequency in Peripheral Blood," Abstract for Poster Session, Multiple Sclerosis by Keystone Symposia, Montana, presented Jan. 11, 2013.
Nakamura, et al., "Clinical features of multiple sclerosis with high plasmablast frequency in peripheral blood" Abstract, Multiple Sclerosis by Keystone Symposia of Molecular and Cellular Biology, Montana, published online Dec. 11, 2012.
Nakamura, et al., "IL-6-dependent Plasmablasts in Pathological Conditions of Relapsing-Remitting Multiple Sclerosis," Japanese Journal of Clinical Immunology 36:345, W5-5 (2013).
Nakamura, M., et al., "Plasmablast in the Pathology of Multiple Sclerosis," Japanese Journal of Clinical Immunology 38(5):403-411 (2015).
Nakamura, The Basics and Clinical Aspects of Angiogenesis—[II] Angiogenesis and Tumors. Invasion/Metastasis/Tumor Suppression of Angiogenesis-Inhibitory Factor NK4 (2002).
Nakashima et al., "Serum Interleukin 6 as a Prognostic Factor in Patients with Prostate Cancer," Clinical Cancer Research 6:2702-2706 (2000).
Narita, et al., "Gemcitabine Selectively Depletes CDIIb+ Gr-1 +Immature Myeloid Cells in Tumor-Bearing Mice and Enhances Anti-Tumor Immune Response," Society for Fundamental Cancer Immunology Sakai Shoroku 10:49, 2006 (with an unverified English translation).

(56) References Cited

OTHER PUBLICATIONS

National Cancer Institute, "SEER Cancer Stat Facts: Pancreas Cancer," https://seer.cancer.gov/statfacts/html/pancreas.html, National Cancer Institute, Bethesda accessed Apr. 25, 2017 (9 pages).
National Cancer Institute, U.S. National Institutes of Health, "Metastatic Cancer: Questions and Answers," accessed Nov. 22, 2014.
Naugler, W.E., et al., "Gender Disparity in Liver Cancer Due to Sex Differences in MyD88-Dependent IL-6 Production," Science 317:121-124 (2007).
Negoro, S., et al., "Activation of JAK/STAT Pathway Transduces Cytoprotective Signal in Rat Acute Myocardial Infarction," Cardiovascular Research 47(4):797-805 (2000).
Ngo, J.T., et al. The Protein Folding Problem and Tertiary Structure Prediction, Merz, Jr. et al. Editors, Birkhauser Boston, 433-506 (1994).
Nishimoto, N., "Clinical Studies in Patients With Castleman's Disease, Crohn's Disease, and Rheumatoid Arthritis in Japan," Clinical Reviews in Allergy & Immunology 28(3):221-30 (2005).
Nishimoto, N, and Kishimoto T., "Inhibition of IL-6 for the Treatment of Inflammatory Diseases," Current Opinion in Pharmacology 4:386-391 (2004).
Nishimoto, N., et al., "Humanized Anti-interleukin-6 Receptor Antibody Treatment of Multicentric Castleman Disease," Blood 106(8):2627-2632 (2005).
Nishimoto, N., et al., "Interleukin 6: From Bench to Bedside," Nature Clinical Practice. Rheumatology 2(11):619-626 (2006).
Nishomoto, N., et al., "Expressions of Immune Response Related Genes Were Normalised After Tocilizumab Treatment in Rheumatoid Arthritis (RA) Patients," Annals of the Rheumatic Diseases 71 (Suppl 3):380, Abstract FRI0198 (2013).
Novick, et al., "Monoclonal Antibodies to the Soluble Human IL-6 Receptor: Affinity Purification, ELISA, and Inhibition of Ligand Binding," Hybridoma 10:137-146 (1991).
Ogata, T., et al., "Anti-IL-6 Receptor Antibody Does Not Ameliorate Radiation Pneumonia in Mice," Experimental and Therapeutic Medicine 4:273-276 (2012).
Ogata, T., et al., "Early Administration of IL-6RA Does Not Prevent Radiation-Induced Lung Injury in Mice," Radiation Oncology 5:26 (2010).
Ohno, S., et al., "Antigen-Binding Specificities of Antibodies Are Primarily Determined by Seven Residues of VH," PNAS 82(9):2945-2949 (1985).
Ohsugi, et al., "Success Story of Pre-market Approved Pipeline," Pharm. Stage 7:13-18 (2007) (English translation included).
Ohsugi, Y. and Tsuchimoto, N., "Pharmacological and Clinical Profile of Humanized Antihuman IL-6 Receptor Antibody (Tocilizumab), a Therapeutic Drug for Castleman's Disease," Folia Pharmacologica Japonica 126(6):419-425 (2005) (with English translation).
Ohtsuka et al., "Relation of Circulating Interleukin-6 to Left Ventricular Remodeling in Patients With Reperfused Anterior Myocardial Infarction," Clinical Cardiology 27(7):417-420 (2004).
Okabe, H., Presentation, "Proprietary Innovative Antibody Engineering Technologies in Chugai Pharmaceutical," 1-78 (2012).
Okada, et al., "IL-6/BSF-2 Functions as a Killer Helper Factor in the in Vitro Induction of Cytotoxic T Cells," Journal of Immunology 141:1543-1549 (1988).
Okada, S., et al., "Elevated Serum Interleukin-6 Levels in Patients with Pancreatic Cancer," Japanese Journal of Clinical Oncology 28:12-15 (1998).
Okada, Y., et al., "Experimental Implication of Celiac Ganglionotropic Invasion of Pancreatic-Cancer Cells Bearing C-Ret Proto-Oncogene With Reference to Glial-cell-line-derived Neurotrophic Factor (GDNF)," International Journal of Cancer 81(1):67-73 (1999).
Okamoto, et al., "Inhibition of Interleukin-6 Signaling Attenuates Left Ventricular Remodeling After Experimental Myocardial Infarction," Journal of Cardiac Failure 11 (9): P066 (2005).
Okamoto, M., et al., "Interleukin-6 as a Paracrine and Autocrine Growth Factor in Human Prostatic Carcinoma Cells in Vitro," Cancer Research 57:141-146 (1997).
Okazaki, M., et al., "Characterization of Anti-Mouse Interleukin-6 Receptor Antibody," Immunology Letters 84(3):231-240 (2002).
Okiyama, N., et al., "Therapeutic Effects of Interleukin-6 Blockade in a Murine Model of Polymyositis That Does Not Require Interleukin-17A," Arthritis & Rheumatism 60(8):2505-2512 (2009).
Onda, M., et al., "Lowering the Isoelectric Point of the Fv Portion of Recombinant Immunotoxins Leads to Decreased Nonspecific Animal Toxicity Without Affecting Antitumor Activity," Cancer Research 61(13):5070-5077 (2001).
Ono, et al., "The Effect of IL-6 on the Des-gamma-carboxy Prothrombin Synthesis in Human Hepatoma Cells," Gastroenterologia Japonica 27:745-750 (1992).
Ono, K., et al., "Cytokine Gene Expression After Myocardial Infarction in Rat Hearts: Possible Implication in Left Ventricular Remodeling," Circulation 98(2):149-156 (1998).
Ozaki, H., et al., "Effectiveness of Multimodality Treatment for Resectable Pancreatic Cancer," International Journal of Pancreatology 7:195-200 (1990).
Ozaki, H., et al., "The Prognostic Significance of Lymph Node Metastasis and Intrapancreatic Perineural Invasion in Pancreatic Cancer After Curative Resection," The Japanese Journal of Surgery 29:16-22 (1999).
Padlan, E.A., et al., "Structure of an Antibody-antigen Complex: Crystal Structure of the HyHEL-10 Fab-Lysozyme Complex," PNAS 86(15):5938-5942 (1989).
Paez-Ribes, M., et al., "Antiangiogenic Therapy Elicits Malignant Progression of Tumors to Increased Local Invasion and Distant Metastasis," Cancer Cell 15(3):220-231 (2009).
Park, H., et al., "Interleukin-6 Protects MIN6 Beta Cells from Cytokin-Induced Apoptosis," Annals of the New York Academy of Sciences 1005:242-249 (2003).
Patel, N.S., et al., "Endogenous Interleukin-6 Enhances the Renal Injury, Dysfunction, and Inflammation Caused by Ischemia/Reperfusion," The Journal of Pharmacology and Experimental Therapeutics 312(3):1170-1178 (2005).
Paul, W.E., "Transplantation and Graft Rejection," Fundamental Immunology 1124-1125, Third Edition (1993).
Paule, B., "Reappraisal of the Concept of Hormone Therapy in Metastatic Prostate Cancer and Implications for Treatment," European Urology 47(6):729-735 (2005).
Pauleikhoff, "Neovascular Age-related Macular Degeneration," Retina 25:1065-84 (2005).
Pavlou, A.K. and Belsey, M.J, "The Therapeutic Antibodies Market to 2008," European Journal of Pharmaceutics and Biopharmaceutics 59(3):389-396 (2005).
Perez-Sanchez, C., et al., "Diagnostic Potential of Netosis-derived Products for Disease Activity, Atherosclerosis and Therapeutic Effectiveness in Rheumatoid Arthritis Patients," Journal of Autoimmunity 82:31-40 (2017).
Peters, S.J., et al., "Engineering an Improved IgG4 Molecule With Reduced Disulfide Bond Heterogeneity and Increased Fab Domain Thermal Stability," The Journal of Biological Chemistry 287(29):24525-24533 (2012).
Peters, M. C., et al., "Plasma IL6 levels, metabolic dysfunction, and asthma severity: a cross-sectional analysis of two cohorts," Lancet Respir Med., 4(7):574-584 (2016).
Phillips, A.J., "The Challenge of Gene Therapy and DNA Delivery," The Journal of Pharmacy and Pharmacology 53(9):1169-1174 (2001).
Pikarsky, E., et al., "NF-KB Functions as a Tumour Promoter in Inflammationassociated Cancer," Nature 431:461-466 (2004).
Pini, A., et al., "Design and Use of a Phage Display Library. Human Antibodies With Subnanomolar Affinity Against a Marker of Angiogenesis Eluted From a Two-dimensional Gel," The Journal of Biological Chemistry 273(34):21769-21776 (1998).
Pirollo, K.F. and Chang, E.H.,"Targeted Delivery of Small Interfering RNA: Approaching Effective Cancer Therapies," Cancer Research 68:1247-1250 (2008).
Poli, V., et al., "Interleukin-6 Deficient Mice Are Protected From Bone Loss Caused by Estrogen Depletion," The EMBO Journal 13(5):1189-1196 (1994).
Polman et al., "Diagnostic Criteria for Multiple Sclerosis: 2010 Revisions to the McDonald Criteria," Annals of Neurology 69(2):292-302 (2011).

(56) References Cited

OTHER PUBLICATIONS

Porgador, A., et al., "Interleukin 6 Gene Transfection Into Lewis Lung Carcinoma Tumor Cells Suppresses the Malignant Phenotype and Confers Immunotherapeutic Competence Against Parental Metastatic Cells,"Cancer Research 52:3679-3686 (1992).
Puhakka, M., et al., "Interleukin-6 and Tumor Necrosis Factor Alpha in Relation to Myocardial Infarct Size and Collagen Formation," Journal of Cardiac Failure 9(4):325-332 (2003).
Q&A de wakaru himan to tounyoubyou, 3(6):982-984 (2004) (with English translation).
Quentmeier, H., et al., "Role of IL-6, IL-2, and IL-4 in the In Vitro Induction of Cytotoxic T Cells," Journal of Immunology 149(10):3316-3320 (1992).
Rajpal, A., et al., "A General Method for Greatly Improving the Affinity of Antibodies by Using Combinatorial Libraries," Proceedings of the National Academy of Sciences of the United States of America 102(24):8466-8471 (2005).
Ramzy, D., et al., "Cardiac Allograft Vasculopathy: A Review," Canadian Journal of Surgery 48(4):319-327 (2005).
Reddy, M.P., et al., "Elimination of Fc Receptor-dependent Effector Functions of a Modified lgG4 Monoclonal Antibody to Human Cd4," Journal of Immunology 164(4):1925-1933 (2000).
Reichert, J. M., "Antibodies to watch in 2014," mAbs 6(4): 799-802 (2014).
Reichert, J.M., et al., "Monoclonal Antibody Successes in the Clinic," Nature Biotechnology 23(9):1073-1078 (2005).
Revez, J.N.M.A., "The Role of the Interleukin-6 Pathway in Asthma," A thesis submitted for the degree of Doctor of Philosophy 78-115, University of Queensland, Australia (2018). [retrieved on Mar. 13, 2019], [Retrieved from the Internet:URL: https://espace.library.uq.edu.au/view/UQ:5f9d90b/s43414462_final_thesis.pdf].
Rikiishi, H., et al., "The Roles of Cytokine in Organ-Specific Tumor Metastasis," Human Cell 6(1):21-28 (1993).
Roitt, et al., Immunology, Moscow, Mir, 110 (2000).
Rothe, A., et al., "Ribosome Display for Improved Biotherapeutic Molecules," Expert Opinion on Biological Therapy 6(2):177-187 (2006).
Rudikoff, S., et al., "Single Amino Acid Substitution Altering Antigen-binding Specificity," Proceedings of the National Academy of Sciences of the United States of America 79(6):1979-1983 (1982).
Ruiz-Limon, P., et al., "Tocilizumab Improves the Proatherothrombotic Profile of Rheumatoid Arthritis Patients Modulating Endothelial Dysfunction, NETosis, and Inflammation," Translational Research 183:87-103 (2017).
Saadoun, S., et al., "Neutrophil Protease Inhibition Reduces Neuromyelitis Optica-Immunoglobulin G-Induced Damage in Mouse Brain," Annals of Neurology 71(3):323-333 (2012).
Sacchi, et al., "Treatment With Monoclonal Antibody to a Lewis Lung Carcinoma-Associated Antigen: Different Effects on Primary Tumor and its Metastases," Cancer Treatment Reviews 69:985-991 (1985).
Sack, U., et al., "Interleukin-6 in Synovial Fluid is Closely Associated With Chronic Synovitis in Rheumatoid Arthritis," Rheumatology International 13(2):45-51 (1993).
Salfeld, J.G., "Isotype Selection in Antibody Engineering," Nature Biotechnology 25(12):1369-1372 (2007).
Salgado, R., et al., "Circulating Interleukin-6 Predicts Survival in Patients with Metastatic Breast Cancer," International Journal of Cancer 103(5):642-646 (2003).
Sanayama, Y., et al., "Prediction of Therapeutic Responses to Tocilizumab in Patients With Rheumatoid Arthritis: Biomarkers Identified by Analysis of Gene Expression in Peripheral Blood Mononuclear Cells Using Genome-Wide DNA Microarray," Arthritis & Rheumatology 66(6):1421-1431 (2014).
Sansone, P., et al., "IL-6 Triggers Malignant Features in Mammospheres From Human Ductal Breast Carcinoma and Normal Mammary Gland," Journal of Clinical Investigation 117(12):3988-4002 (2007).
Sarkar, F. H., et al., "Back to the Future: COX-2 Inhibitors for Chemoprevention and Cancer Therapy," Mini-Reviews in Medicinal Chemistry 7(6):599-608 (2007).
Sato, K., et al., "Reshaping a Human Antibody to Inhibit the Interleukin 6-dependent Tumor Cell Growth," Cancer Research 53(4):851-856 (1993).
Schultz, E., "Satellite Cell Proliferative Compartments in Growing Skeletal Muscles," Developmental Biology 175:84-94 (1996).
Schultz, E., et al., "Acute Effects of Hindlimb Unweighting on Satellite Cells of Growing Skeletal Muscle," Journal of applied physiology 76(1):266-70 (1994).
Schultz et al., "Response of Satellite Cells to Focal Skeletal Muscle Injury," Muscle Nerve 8:217-222 (1985).
Sebba, A., "Tocilizumab: The First Interleukin-6-Receptor Inhibitor," American Journal of Health-System Pharmacy 65(15):1413-1418 (2008).
Seddon, J. M., et al., "Progression of Age-related Macular Degeneration," Arch Ophthalmol. 123:774-782 (2005).
Shang, G.S., et al., "IL-6 and TNF-α Promote Metastasis of Lung Cancer by Inducing Epithelial-Mesenchymal Transition," Oncology Letters 13(6):4657-4660 (2017).
Shewach, D. S. and Lawrence, T. S., "Gemcitabine and Radiosensitization in Human Tumor Cells," Investigational New Drugs 14:257-263 (1996).
Shimazaki, et al., "Hito Kotsuzuishu Model to Ko hito IL-6 Juyotai Kotai no Ko Shuyo Koka," Rinsho Ketsueki 38:281-284 (1997) (English translation provided).
Shimizu, J., et al., "IFNβ-1b May Severely Exacerbate Japanese Optic-spinal Ms in Neuromyelitis Optica Spectrum," Neurology 75(16):1423-1427 (2010).
Shimizu, H., et al., "KRP-203, a Novel Synthetic Immunosuppressant, Prolongs Graft Survival and Attenuates Chronic Rejection in Rat Skin and Heart Allografts," Circulation 111(2):222-22 (2005).
Shimizu, K. and Oku, N., "Cancer Anti-Angiogenic Therapy," Biological and Pharmaceutical Bulletin 27(5):599-605, (2004).
Shinriki, S., et al., "Humanized Anti-interleukin-6 Receptor Antibody Suppresses Tumor Angiogenesis and in Vivo Growth of Human Oral Squamous Cell Carcinoma," Clinical Cancer Research 15(17):5426-5434 (2009).
Shire, S.J., et al., "Challenges in the Development of High Protein Concentration Formulations," Journal of Pharmaceutical Sciences 93(6):1390-1402 (2004).
Sideleva, O., et al., "Obesity and Asthma: An Inflammatory Disease of Adipose Tissue Not the Airway," American Journal of Respiratory and Critical Care Medicine 186(7):598-605 (2012).
Skolnick, J. and Fetrow, J.S., "From Genes to Protein Structure and Function: Novel Applications of Computational Approaches in the Genomic Era," Trends in Biotechnology 18(1):34-39 (2000).
Skurkovich, S.V., et al., "Anticytokine Therapy—New Approach to the Treatment of Autoimmune and Cytokine-Disturbance Diseases," Oncology and Immunopathology 2:71-80 (2003) (Partial English translation).
Sleeman, J. and Steeg, P. S., "Cancer metastasis as a therapeutic target," Eur J Cancer, 46(7):1177-1180 (2010).
Smith, P. C. and Keller, E. T., "Anti-Interleukin-6 Monoclonal Antibody Induces Regression of Human Prostate Cancer Xenografts in Nude Mice," Prostate 48:47-53 (2001).
Smith, T.F., et al., "The Challenges of Genome Sequence Annotation or "the Devil is in the Details"," Nature Biotechnology 15(12):1222-1223 (1997).
Snow, M.H., "Satellite Cell Response in Rat Soleus Muscle Undergoing Hypertrophy Due to Surgical Ablation of Synergists," The Anatomical Record 227(4):437-446 (1990).
Snow, M.H., et al., "Myogenic Cell Formation in Regenerating Rat Skeletal Muscle Injured by Mincing. I. A Fine Structural Study," The Anatomical Record 188(2):181-199 (1977).
Sparano, A., et al., "Modulation of Th1 and Th2 Cytokine Profiles and Their Association With Advanced Head and Neck Squamous Cell Carcinoma," Otolaryngology—Head and Neck Surgery 131(5):573-576 (2004).
Srivastava, et al., "Potassium Channel KIR4.1 as an Immune Target in Multiple Sclerosis," The New England Journal of Medicine 12, 367:115-123 (2012).

(56) References Cited

OTHER PUBLICATIONS

Stan, A.C., et al., "In Vivo Inhibition of Angiogenesis and Growth of the Human U-87 Malignant Glial Tumor by Treatment With an Antibody Against Basic Fibroblast Growth Factor," Journal of Neurosurgery 82(6):1044-1052 (1995).
Steeg, P. S. and Theodorescu, D., "Metastasis: a Therapeutic Target for Cancer," Nature Clinical Practice Oncology 5(4):206-219 (2008).
Steeg, P. S., "Tumor Metastasis: Mechanistic Insights and Clinical Challenges," Nature Medicine 12(8):895-904 (2006).
Strand, V., et al., "Biologic Therapies in Rheumatology: Lessons Learned, Future Directions," Nature Reviews. Drug Discovery 6(1):75-92 (2007).
Strassmann, G., et al., "Evidence for the Involvement of Interleukin 6 in Experimental Cancer Cachexia," The Journal of Clinical Investigation 89(5):1681-1684 (1992).
Studebaker et al., "Fibroblasts Isolated From Common Sites of Breast Cancer Metastasis Enhance Cancer Cell Growth Rates and Invasiveness in an Interleukin-6-dependent Manner," Cancer Research 68(21):9087-9095 (2008).
Sugahara, H., et al., "Expression of Interleukin-6 in Human Intrahepatic Biliary Tract and its Pathologic Significance; An Inununohistochemical and In situ Hybridization Study," Juzen Medical Society 105:819-833 (1996).
Sumida, K., et al., "Anti-IL-6 receptor mAb eliminates myeloid-derived suppressor cells and inhibits tumor growth by enhancing T-cell responses," Eur J Immunol., 42:2060-2072 (2012).
Suzuki, et al., "Gemcitabine Selectively Eliminates Splenic Gr-1+/CDIIb+ Myeloid Suppressor Cells in Tumor-Bearing Animals and Enhances Antitumor Immune Activity," Clinical Cancer Research 11:6713-6721 (2005).
Taga, T., et al., "Interleukin-6 Triggers the Association of Its Receptor With a Possible Signal Transducer, gp130," Cell 58(3):573-581 (1989).
Taga, T., et al., "Receptors for B Cell Stimulatory Factor 2" The Journal of Experimental Medicine 166:967-981 (1987).
Takahashi, H., et al., "Antiproteases in Preventing the Invasive Potential of Pancreatic Cancer Cells," Journal of the Pancreas 8(4 Suppl):501-508 (2007).
Takeda, K., et al., "Murine Tumor Cells Metastasizing Selectively in the Liver: Ability to Produce Hepatocyte-Activating Cytokines Interleukin-1 and/or -6," Japanese Journal of Cancer Research 82:1299-1308 (1991).
Takeshita, et al., Rinsho Shinkeigaku vol. 59(Supplement 224 O-08-6) (2019).
Takeshita, Y., et al., "The Effect of NMO-IgG and Anti-IL-6 Receptor Monoclonal Antibody (SA237) for the Blood-Brain Barrier," Abstract for presentation No. O-08-6, 60th Annual Meeting of the Japanese Society of Neurology, accessed at http://www.neurology-jp.org/neuro2019/abstract/pdf/adoption_03.pdf, accessed on Feb. 18, 2019.
Takeshita, Y., et al., "Effects of Neuromyelitis Optica-IgG at the Blood-Brain Barrier in Vitro," Neurology Neuroimmunology & Neuroinflammation 4(1):e311 (2016).
Takizawa, H., et al., "Growth Inhibition of Human Lung Cancer Cell Lines by Interleukin 6 in Vitro: A Possible Role in Tumor Growth via an Autocrine Mechanism," Cancer Research 53:4175-4181 (1993).
Takkinen, K., et al., "Affinity and Specificity Maturation by CDR Walking," Antibody Engineering 38:540-545 (2001).
Tamura, T., et al., "Soluble Interleukin-6 Receptor Triggers Osteoclast Formation by Interleukin 6," PNAS 90:11924-11928 (1993).
Tan, P.H., et al., "Engineering the Isoelectric Point of a Renal Cell Carcinoma Targeting Antibody Greatly Enhances ScFv Solubility," Immunotechnology: an International Journal of Immunological Engineering, 4(2):107-114 (1998).
Tanaka, F., et al., "The Anti-Human Tumor Effect and Generation of Human Cytotoxic T Cells in SCID Mice Given Human Peripheral Blood Lymphocytes by the in Vivo Transfer of the Interleukin-6 Gene Using Adenovirus Vector," Cancer Research 57(7):1335-1343 (1997).
Tanaka, T., et al., "Therapeutic Targeting of the Interleukin-6 Receptor," Annu Rev Pharmacol Toxicol., 52:199-219 (2012).
Tantraworasin, A., et al., "Prognostic Factors of Tumor Recurrence in Completely Resected Non-Small Cell Lung Cancer," Cancer Management and Research 5:77-84 (2013).
Teeling, J.L., et al., "The Biological Activity of Human CD20 Monoclonal Antibodies is Linked to Unique Epitopes on CD20," Journal of Immunology (Baltimore, Md.: 1950) 177(1):362-371 (2006).
Tintore, M., et al., "Isolated Demyelinating Syndromes: Comparison of Different MR Imaging Criteria to Predict Conversion to Clinically Definite Multiple Sclerosis," AJNR American Journal of Neuroradiology 21:702-706 (2000).
Tisdale, M.J., "Biology of Cachexia," Journal of the National Cancer Institute 89(23):1763-1773 (1997).
Tobe et al., "Targeted Disruption of the FGF2 Gene does not Prevent Choroidal Neovascularization in the Murine Model," The American Journal of Pathology 153:1641-1646 (1998).
Trikha, M., et al., "Targeted Anti-Interleukin-6 Monoclonal Antibody Therapy for Cancer: A Review of the Rationale and Clinical Evidence," Clinical Cancer Research 9(13):4653-4665 (2003).
Tsuchiya, M., "Therapeutic Antibody," Credit Suisse Seminar at Fuji-Gotemba Research Laboratories, p. 21 (2006) (with English translation).
Tsujinaka, T., et al., "Interleukin 6 Receptor Antibody Inhibits Muscle Atrophy and Modulates Proteolytic Systems in Interleukin 6 Transgenic Mice," The Journal of Clinical Investigation 97(1):244-249 (1996).
Uchida, T., et al., "Increased Cerebrospinal Fluid Metalloproteinase-2 and Interleukin-6 are Associated with Albumin Quotient in Neuromyelitis Optica: Their Possible Role on Blood-Brain Barrier Disruption," Multiple Sclerosis 23(8):1072-1084 (2017).
Ulich, T. R., et al., "Intratracheal Injection of Endotoxin and Cytokines, Ii. Lnterleukin-6 and Transforming Growth Factor Bela Inhibit Acute Inftammation," The American Journal of Pathology 138(5):1097-1101 (1991).
Unverified English language translation of French Patent FR2694767A1, published Feb. 18, 1994, 12 pages.
U.S. National Library of Medicine (NIH) publication (online), MedlinePlus Medical Encyclopedia, "Liver metastases," Accessed Nov. 22, 2014.
Vajdos, F.F., et al., "Comprehensive Functional Maps of the Antigen-binding Site of an Anti-ErbB2 Antibody Obtained With Shotgun Scanning Mutagenesis," Journal of Molecular Biology 320(2):415-428 (2002).
Valantine, H., "Cardiac Allograft Vasculopathy After Heart Transplantation: Risk Factors and Management," The Journal of Heart and Lung Transplantation 23:S187-S193 (2004).
Van Der Meulen, J., et al., "The H3K27me3 Demethylase UTX in Normal Development and Disease," Epigenetics 9(5):658-668 (2014).
Van Haaften, G., et al., "Somatic Mutations of the Histone H3K27 Demethylase Gene UTX in Human Cancer," Nature Genetics 41(5):521-523 (2009).
Van Walle, I., et al., "Immunogenicity Screening in Protein Drug Development," Expert Opinion on Biological Therapy 7(3):405-418 (2007).
Vidal, L., et al., "Making Sense of Antisense," European Journal of Cancer 41:2812-2818 (2005).
Vincent, J., et al., "5-fluorouracil Selectively Kills Tumor-associated Myeloid-derived Suppressor Cells Resulting in Enhanced T Cell-dependent Antitumor Immunity," Cancer Research 70(8):3052-3061 (2010).
Wang, H., et al., "Phase II Study of Panobinostat and Bortezomib in Patients with Pancreatic Cancer Progressing on Gemcitabine-Based Therapy," Anticancer Research 32:1027-1032 (2012).
Wang, J., et al., "Endogenous and Exogenous IL-6 Inhibit Aeroallergen-Induced Th2 Inflammation," Journal of Immunology 165(7):4051-4061 (2000).
Wang, L. and Shilatifard, A., "UTX Mutations in Human Cancer," Cancer Cell 35(2):168-176 (2019).
Wang, X.D., et al., "Mechanical Load-dependent Regulation of Satellite Cell and Fiber Size in Rat Soleus Muscle," American Journal of Physiology 290(4):C981-C989 (2006).

(56) References Cited

OTHER PUBLICATIONS

Wang, J., et al., "IL-6 pathway-driven investigation of response to IL-6 receptor inhibition in rheumatoid arthritis," BMJ Open, 3:e003199 (2013).
Warren, G.L., et al., "Physiological Role of Tumor Necrosis Factor Alpha in Traumatic Muscle Injury," FASEB Journal 16(12):1630-1632 (2002).
Waubant, et al., "Clinical Characteristics of Responders to Interferon Therapy for Relapsing MS," Neurology 61:184-189 (2003).
Webber, S. A., et al., "Heart and lung transplantation in children," Lancet 368:53-69 (2006).
Weber, G.F., "Why Does Cancer Therapy Lack Effective Anti-Metastasis Drugs?," Cancer Letters 328(2):207-211 (2013).
Wells, J.A., "Additivity of Mutational Effects in Proteins," Biochemistry 29(37):8509-8517 (1990).
Weyand, M., et al., "Serial Interleukin-6 Blood Levels Early After Cardiac Transplantation," Transplantation Proceedings 24(6):2546 (1992).
Wilansky, S., "Echocardiography in the Assessment of Complications of Myocardial Infarction," Texas Heart Institute Journal 18(4):237-242 (1991).
Wingerchuk, D.M., et al., "International Consensus Diagnostic Criteria for Neuromyelitis Optica Spectrum Disorders," Neurology 85:177-189 (2015).
Wingerchuk, D.M., et al., "Revised Diagnostic Criteria for Neuromyelitis Optica," Neurology 66(10):1485-1489 (2006).
Wingerchuk, D.M., et al., "The Spectrum of Neuromyelitis Optica," The Lancet. Neurology 6(9):805-815 (2007).
Wong, B. W., et al., "Progress in Heart Transplantation," Cardiovascular Pathology 14:176-180 (2005).
Wright, H.L., et al., "Neutrophil Biomarkers Predict Response to Therapy with Tumor Necrosis Factor Inhibitors in Rheumatoid Arthritis," Journal of Leukocyte Biology 101(3):785-795 (2017).
Wu, C.T., et al., "Predictive Value of CD44 in Muscle-Invasive Bladder Cancer and Its Relationship with IL-6 Signaling," Annals of Surgical Oncology 25(12):3518-3526 (2018).
Wu, H., et al., "Humanization of a Murine Monoclonal Antibody by Simultaneous Optimization of Framework and CDR Residues," Journal of Molecular Biology 294(1):151-162 (1999).
Wu, H., et al., "Detory Syncytial Virus Infection in the Upper and Lower Respiratory Tractvelopment of Motavizumab, an Ultrapotent Antibody for the Prevention of Respira," Journal of Molecular biology 368(3):652-665 (2007).
Xing, Y., et al., "The Effect of Interleukin-6 on the Proliferation of Prostate Cancer Cells in vitro and the Modulation of This Procedure", Journal of Tongji Medical University 21:225-227 (2001).
Yamakawa, Y., et al., "Astrocytes Promote the Proliferation of Lung Cancer Cells in Brain Metastases via Inflammatory Cytokines, Especially IL-6," Neuroscience 48(2/3):216, P-22 (poster presentation) (2009).
Yamamoto, N., et al., "Regulatory Mechanisms for Production of IFN-γ and TNF by Antitumor T Cells or Macroophages in the Tumor-Bearing State," Journal of Immunology 154:2281-2290(1995).
Yamamura, "Anti-IL-6 Receptor Therapy for Neuromyelitis Optica," Neurological Therapeutics 33(5):SI20 (2016) (with English translation).
Yamamura, T., et al., "A Double-Blind Placebo-Controlled Study of Satralizumab (SA237), a Recycling Anti-IL-6 Receptor Monoclonal Antibody, as add-on Therapy for Neuromyelitis Optica (NMO) and NMO Spectrum Disorder (NMOSD)," European Journal of Neurology, 2018, 25 (Suppl. 2), p. 536, abstract EPR3103 for presentation given on Jun. 16, 2018). EPR3103 (https://ipp-ean18.netkey.at/index.php?p=recorddetail&rid=f16c1ff3-f5ec-4b71-8a99-7c39bdc90418&t).
Yamamura, "Treatment failures in NMO are Due to Specific Immunologic Mechanisms," Meeting of the 9th Annual International Roundtable Conference on NMO, Mar. 13, 2017, 17 pages.
Yamasaki, K., et al., "Cloning and Expression of the Human Interleukin-6 (BSF-2/IFN/3 2) Receptor," Science 241(4867):825-828 (1988).
Yamauchi-Takihara, K., et al., "Hypoxic Stress Induces Cardiac Myocyte-derived Interleukin-6", Circulation 91:1520-1524 (1995).
Yan, L., "(II) Abdominal discomfort and pain," Theory and Practice of Oncology, C43 Shandong Science and Technology Press, 2 pages (2006).
Yang, Y.F., et al., "Enhanced Induction of Antitumor T-Cell Responses by Cytotoxic T Lymphocyte-associated Molecule-4 Blockade: The Effect Is Manifested Only at the Restricted Tumor-bearing Stage," Cancer Research 57: 4036-4041 (1997).
Yokota, S., et al., "Clinical Study of Tocilizumab in Children With Systemic-Onset Juvenile Idiopathic Arthritis," Clinical Reviews in Allergy & Immunology 28(3):231-238 (2005).
Yoshio-Hoshino et al., "Establishment of a New Interleukin-6 (IL-6) Receptor Inhibitor Applicable to the Gene Therapy for IL-6-Dependent Tumor," Cancer Research 67:871-875 (2007).
Yue, P., et al., "Cytokine Expression Increases in Nonmyocytes From Rats With Postinfarction Heart Failure," The American Journal of Physiology 275(1):H250-H258 (1998).
Zaki, M.H., et al., "CNTO 328, A Monoclonal Antibody to IL-6, Inhibits Human Tumor-induced Cachexia in Nude Mice," International Journal of Cancer 111:592-595 (2004).
Zangari, M., et al., "Immunomodulatory Drugs in Multiple Myeloma," Expert Opinion on Investigational Drugs 14(11):1411-1418 (2005).
Zhang, G. J. and Adachi, I., "Serum Interleukin-6 Levels Correlate to Tumor Progression and Prognosis in Metastatic Breast Carcinoma," Anticancer Research 19:1427-1432 (1999).
Zijun, L., "Tissue Infiltration," Tumor Metastasis, Shanxi Science and Technology Press, 5 pages (2007).
U.S. Appl. No. 07/364,056, filed Jun. 9, 1989, Donough, et al.
U.S. Appl. No. 07/530,580, filed May 30, 1990, Novick, et al.
U.S. Appl. No. 07/634,278, filed Dec. 19, 1990, Queen, et al.
U.S. Appl. No. 08/137,117, filed Dec. 20, 1993, Tsuchiya, et al.
U.S. Appl. No. 08/197,834, filed Feb. 17, 1994, Shimamura, et al.
U.S. Appl. No. 08/329,785, filed Oct. 27, 1994, Novick, et al.
U.S. Appl. No. 08/357,080, filed Dec. 15, 1994, Kishimoto.
U.S. Appl. No. 08/436,717, filed May 8, 1995, Tsuchiya, et al.
U.S. Appl. No. 08/553,501, filed Feb. 20, 1996, Tsuchiya, et al.
U.S. Appl. No. 08/817,084, filed Apr. 7, 1997, Kishimoto, et al.
U.S. Appl. No. 08/875,927, filed Aug. 13, 1997, Tsujinaka, et al.
U.S. Appl. No. 08/882,447, filed Jun. 26, 1997, Barbera-Guillem.
U.S. Appl. No. 09/205,231, filed Dec. 4, 1998, Tsuchiya, et al.
U.S. Appl. No. 09/646,188, filed Sep. 14, 2000, Ito, et al.
U.S. Appl. No. 09/756,125, filed Jan. 9, 2001, Kishimoto, et al.
U.S. Appl. No. 10/030,915, filed May 23, 2002, Isobe, et al.
U.S. Appl. No. 10/120,272, filed Apr. 9, 2002, Kirk, et al.
U.S. Appl. No. 10/141,766, filed May 10, 2002, Mihara, et al.
U.S. Appl. No. 10/280,716, filed Oct. 26, 2002, Giles-Komar, et al.
U.S. Appl. No. 10/351,748, filed Jan. 24, 2003, Winter.
U.S. Appl. No. 10/399,979, filed Apr. 24, 2003, Ito; Hiroaki, et al.
U.S. Appl. No. 10/496,793, filed Nov. 30, 2004, Blay, et al.
U.S. Appl. No. 10/546,149, filed Aug. 22, 2005, Okano, et al.
U.S. Appl. No. 10/554,407, filed Oct. 24, 2005, Okuda, et al.
U.S. Appl. No. 10/569,831, filed Feb. 28, 2006, Nakade, et al.
U.S. Appl. No. 10/573,528, filed Mar. 24, 2006, Ochiai, et al.
U.S. Appl. No. 10/575,455, filed Aug. 9, 2006, Nishimoto, et al.
U.S. Appl. No. 10/593,786, filed Aug. 26, 2008, Kano, et al.
U.S. Appl. No. 10/607,050, filed Jun. 27, 2003, Yamamura, et al.
U.S. Appl. No. 10/677,227, filed Oct. 3, 2003, Ito, et al.
U.S. Appl. No. 10/714,353, filed Nov. 14, 2003, Schuurman, et al.
U.S. Appl. No. 10/837,904, filed May 4, 2004, Tsuchiya, et al.
U.S. Appl. No. 10/922,675, filed Aug. 20, 2004, McSwiggen, et al.
U.S. Appl. No. 10/926,806, filed Aug. 26, 2004, Shima, et al.
U.S. Appl. No. 11/089,426, filed Mar. 24, 2005, Gillies, et al.
U.S. Appl. No. 11/197,488, filed Aug. 5, 2005, Young, et al.
U.S. Appl. No. 11/244,142, filed Oct. 6, 2005, Lawless.
U.S. Appl. No. 11/340,412, filed Jan. 25, 2006, Mihara.
U.S. Appl. No. 11/514,217, filed Sep. 1, 2006, Yoshizaki, et al.
U.S. Appl. No. 11/585,172, filed Oct. 24, 2006, Kishimoto, et al.
U.S. Appl. No. 11/608,342, filed Dec. 8, 2006, Zaki, et al.
U.S. Appl. No. 11/631,128, filed Feb. 20, 2007, Kudou, et al.

(56) References Cited

OTHER PUBLICATIONS

U.S. Appl. No. 11/809,482, filed Jun. 1, 2007, Stevens, et al.
U.S. Appl. No. 11/858,418, filed Sep. 20, 2007, Nemeth.
U.S. Appl. No. 12/085,065, filed Jun. 1, 2009, Okada, et al., related application.
U.S. Appl. No. 12/090,061, filed Mar. 6, 2009, Yasunami, related application.
U.S. Appl. No. 12/090,676, filed Feb. 25, 2009, Kobara, related application.
U.S. Appl. No. 12/094,644, filed Feb. 27, 2009, Nakashima, et al., related application.
U.S. Appl. No. 12/153,612, filed May 21, 2008, Garcia-Martinez, et al.
U.S. Appl. No. 12/159,778, filed Jun. 30, 2008, Morichika, et al.
U.S. Appl. No. 12/161,733, filed Mar. 9, 2009, Ishida.
U.S. Appl. No. 12/232,341, filed Sep. 16, 2008, Mihara, et al.
U.S. Appl. No. 12/296,193, filed Apr. 15, 2009, Nishimoto, et al.
U.S. Appl. No. 12/502,581, filed Jul. 14, 2009, Garcia-Martinez, et al.
U.S. Appl. No. 12/524,041, filed Sep. 18, 2009, Takahashi, et al., related application.
U.S. Appl. No. 12/679,922, filed Oct. 1, 2010, Igawa, et al.
U.S. Appl. No. 12/680,082, filed Jun. 25, 2010, Igawa, et al.
U.S. Appl. No. 12/680,087, filed Jan. 3, 2011, Igawa, et al.
U.S. Appl. No. 12/680,112, filed Jun. 23, 2010, Igawa, et al., related application.
U.S. Appl. No. 12/780,006, filed May 14, 2010, Radin, et al.
U.S. Appl. No. 12/936,587, filed Jan. 3, 2011, Igawa, et al.
U.S. Appl. No. 12/996,162, filed Mar. 7, 2011, Mitsunaga, et al., related application.
U.S. Appl. No. 13/283,177, filed Oct. 27, 2011, Chen, et al.
U.S. Appl. No. 13/290,366, filed Nov. 7, 2011, Zhang, et al.
U.S. Appl. No. 13/387,292, filed Apr. 3, 2012, Maeda, related application.
U.S. Appl. No. 13/524,528, filed Jun. 15, 2012, Igawa, et al., related application.
U.S. Appl. No. 13/700,355, filed Apr. 2, 2013, Nishimura, related application.
U.S. Appl. No. 13/959,489, filed Aug. 5, 2013, Igawa, et al., related application.
U.S. Appl. No. 14/520,423, filed Oct. 22, 2014, Igawa, et al., related application.
U.S. Appl. No. 14/878,163, filed Oct. 8, 2015, Mitsunaga, et al.
U.S. Appl. No. 14/897,498, filed Dec. 10, 2015, Yamamura, et al., related application.
U.S. Appl. No. 15/263,617, filed Sep. 13, 2016, Igawa, et al., related application.
U.S. Appl. No. 15/503,441, filed Feb. 13, 2017, Fukuda, et al.
U.S. Appl. No. 15/553,609, filed Aug. 25, 2017, Igawa, et al., related application.
U.S. Appl. No. 15/575,027, filed Nov. 17, 2017, Yamamura, et al., related application.
U.S. Appl. No. 15/877,894, filed Jan. 23, 2018, Maeda, related application.
U.S. Appl. No. 16/041,976, filed Jul. 23, 2018, Igawa, et al., related application.
U.S. Appl. No. 16/609,053, filed Oct. 28, 2019, Matsuoka, et al., related application.
U.S. Appl. No. 16/963,311, filed Jul. 20, 2020, Kato, et al., related application.
U.S. Appl. No. 17/097,298, filed Nov. 13, 2020, Igawa, et al., related application.
U.S. Appl. No. 17/437,448, filed Sep. 9, 2021, Takeshita, et al., related application.
U.S. Appl. No. 17/509,128, filed Oct. 25, 2021, Igawa, et al., related application.
U.S. Appl. No. 17/601,831, filed Oct. 6, 2021, Honda, et al., related application.
U.S. Appl. No. 17/829,641, filed Jun. 1, 2022, Igawa, et al., related application.
U.S. Appl. No. 12/085,065, filed Jun. 1, 2009, Okada, et al.
U.S. Appl. No. 12/090,061, filed Mar. 6, 2009, Yasunami.
U.S. Appl. No. 12/090,676, filed Feb. 25, 2009, Kobara.
U.S. Appl. No. 12/094,644, filed Feb. 27, 2009, Nakashima, et al.
U.S. Appl. No. 12/524,041, filed Sep. 18, 2009, Takahashi, et al.
U.S. Appl. No. 12/680,112, filed Jun. 23, 2010, Igawa, et al.
U.S. Appl. No. 12/996,162, filed Mar. 7, 2011, Mitsunaga, et al.
U.S. Appl. No. 13/387,292, filed Apr. 3, 2012, Maeda.
U.S. Appl. No. 13/524,528, filed Jun. 15, 2012, Igawa, et al.
U.S. Appl. No. 13/700,355, filed Apr. 2, 2013, Nishimura.
U.S. Appl. No. 13/959,489, filed Aug. 5, 2013, Igawa, et al.
U.S. Appl. No. 14/520,423, filed Oct. 22, 2014, Igawa, et al.
U.S. Appl. No. 14/897,498, filed Dec. 10, 2015, Yamamura, et al.
U.S. Appl. No. 15/263,617, filed Sep. 13, 2016, Igawa, et al.
U.S. Appl. No. 15/553,609, filed Aug. 25 2017, Igawa, et al.
U.S. Appl. No. 15/575,027, filed Nov. 17, 2017, Yamamura, et al.
U.S. Appl. No. 15/877,894, filed Jan. 23, 2018, Maeda.
U.S. Appl. No. 16/041,976, filed Jul. 23, 2018, Igawa, et al.
U.S. Appl. No. 16/609,053, filed Oct. 28, 2019, Matsuoka, et al.
U.S. Appl. No. 16/963,311, filed Jul. 20, 2020, Kato, et al.
U.S. Appl. No. 17/097,298, filed Nov. 13, 2020, Igawa, et al.
U.S. Appl. No. 17/437,448, filed Sep. 9, 2021, Takeshita, et al.
U.S. Appl. No. 17/509,128, filed Oct. 25, 2021, Igawa, et al.
U.S. Appl. No. 17/601,831, filed Oct. 6, 2021, Honda, et al.
U.S. Appl. No. 17/829,641, filed Jun. 1, 2022, Igawa, et al.
Actemra (tocilizumab), Highlights of Prescribing Information, revised Aug. 2017, 1 page.
Anonymous, "Interleukin 6—Wikipedia," XP055598802, edited Feb. 22, 2019, retrieved from the internet on Jun. 24, 2019, https://en.wikipedia.org/wiki/Intereukin_6, 20 pages.
Balint, B., et al., "Alterations of the peripheral B cell compartment in pediatric-onset multiple sclerosis," Journal of Neurology, 258(Suppl1):S202, Abstract No. P732 (2011).
Chihara, N., et al., "Interleukin 6 signaling promotes anti-aquaporin 4 autoantibody production from plasmablasts in neuromyelitis optica," PNAS, 108(9):3701-3706 (2011).
Costa, L., et al., "Efficacy of tocilizumab in a patient with refractory psoriatic arthritis," Clin Rheumatol., 33:1355-1357 (2014).
Dall'Acqua, W. F., et al., "Properties of Human IgG1s Engineered for Enhanced Binding to the Neonatal Fc Receptor (FcRn)," J Biol Chem., 281(33):23514-23524 (2006).
Feaver, R., et al., "The Anti-IL-6 Antibody Sirukumab Inhibits Vascular Inflammation in a Human Surrogate Model of Atherosclerosis," American College of Rheumatology Meeting Abstracts, Abstract No. 439 (2014).
Furuya, Y., et al., "Interleukin-6 as a Potential Therapeutic Target for Pulmonary Arterial Hypertension," Int J Rheumatol., 2010:720305 (2010), 8 pages.
Habara, T., et al., "The biological effects of antiadhesion agents on activated RAW264.7 macrophages," J Biomed Mater Res., 61:628-633 (2002).
Hashizume, M., et al., "Tocilizumab, a humanized anti-interleukin-6 receptor antibody, improved anemia in monkey arthritis by suppressing IL-6-induced hepcidin production," Rheumatol Int., 30:917-923 (2010).
Hashizume, M., et al., "IL-6 plays an essential role in neutrophilia under inflammation," Cytokine, 54:92-99 (2011).
Hashizume, M. and Ohsugi, Y., "IL-6 as a target in autoimmune disease and inflammation," Folia Pharmacol Jpn., 144:172-177 (2014).
Holmdahl, L., "The Role of Fribrinolysis in Adhesion Formation," Eur J Surg., Suppl 577:24-31 (1997).
Honda, S-I., et al., "Marginal zone B cells exacerbate endotoxic shock via interleukin-6 secretion induced by Fcα/μR-coupled TLR4 signalling," Nat Commun., 7:11498 (2016), 10 pages.
Igawa, T., et al., "pH-dependent antigen-binding antibodies as a novel therapeutic modality," Biochim Biophys Acta, 1844:1943-1950 (2014).
Iijima, T., et al., "Tocilizumab improves systemic rheumatoid vasculitis with necrotizing crescentic glomerulonephritis," Mod Rheumatol., 25(1):138-142 (2015).
International Search Report dated Jan. 22, 2019 in International Patent Application No. PCT/JP2018/038955.

(56) References Cited

OTHER PUBLICATIONS

Kishimoto, T., "Interleukin-6 and its Receptor in Autoimmunity," J Autoimmun., 5(Suppl A):123-132 (1992).

Kondo, M., et al., Letters to the Editor, "A case of overlap syndrome successfully treated with tocilizumab: a hopeful treatment strategy for refractory dermatomyositis?" Rheumatology—Oxford Journals, British Society for Rheumatology, 53:1907-1908 (2014).

Kosaka, H., et al., "Intergeron-γ is a therapeutic target molecule for prevention of postoperative adhesion formation," Nat Med., 14(4):437-441 (2008).

Mihara, M., et al., "Anti-Interleukin 6 Receptor Antibody Inhibits Murine AA-Amyloidosis," J Immunol., 31:1132-1138 (2004).

Mori, K., et al., "Novel models of cancer-related anemia in mice inoculated with IL-6-producing tumor cells," Biomed Res., 30(1):47-51 (2009).

Motozawa, N., et al., "Unique circumferential peripheral keratitis in relapsing polychondritis," Medicine, 96(41):e7951 (2017).

Narazaki, M., et al., Letters to the Editor, "Therapeutic effect of tocilizumab on two patients with polymyositis," Rheumatology—Oxford Journals, British Society for Rheumatology, 50:1344-1346 (2011).

Nishimoto, N., et al., "Anti-interleukin 6 receptor antibody treatment in rheumatic disease," Ann Rheum Dis., 59(suppl 1):i21-i27 (2000).

Ohashi, K., et al., "Interferon γ and plasminogen activator inhibitor 1 regulate adhesion formation after partial hepatectomy," Br J Surg., 101:398-407 (2014).

Reed, K. L., et al., "A neurokinin 1 receptor antagonist decreases postoperative peritoneal adhesion formation and increases peritoneal fibrinolytic activity," PNAS, 101(24):9115-9120 (2004).

Saba, A. A., et al., "Effects on Interleukin-6 and its Neutralizing Antibodies on Peritoneal Adhesion Formation and Wound Healing," Am Surg., 62(7):569-572 (1996).

Serada, S., et al., "IL-6 blockade inhibits the induction of myelin antigen-specific Th17 cells and Th1 cells in experimental autoimmune encephalomyelitis," PNAS, 105(26):9041-9046 (2008).

Shima, Y., et al., "Tocilizumab, a humanized anti-interleukin-6 receptor antibody, ameliorated clinical symptoms and MRI findings of a patient with ankylosing spondylitis," Mod Rheumatol., 21:436-439 (2011).

Shimizu, H. and Nishioka, H., "Successful treatment with tocilizumab for refractory scleritis associated with relapsing polychondritis," Scand J Rheurmatol., 46:418-419 (2017).

Silpa-Archa, S., et al., "Outcome of tocilizumab treatment in refractory ocular inflammatory diseases," Acta Ophthalmol., 94:e400-e406 (2016).

Suzuki, H., et al., "Anti-murine IL-6 receptor antibody inhibits IL-6 effects in vivo," Immunol Lett., 30:17-22 (1991).

Suzuki, M., et al., "Anti-inflammatory mechanism of tocilizumab, a humanized anti-IL-6R antibody: effect on the expression of chemokine and adhesion molecule," Rheumatol Int., 30:309-315 (2010).

Wei, G., et al., "Keratinocyte Growth Factor Combined with a Sodium Hyaluronate Gel Inhibits Postoperative Intra-Abdominal Adhesions," Int J Mol Sci., 17:1611 (2016), 17 pages.

U.S. Appl. No. 16/838,415, filed Apr. 2, 2020, Igawa, T., et al., related application.

U.S. Appl. No. 16/983,115, filed Aug. 3, 2020, Kakehi, T., related application.

* cited by examiner

PBS-administered group

MR16-1-administered group (10 mg)

SEQUENCE LISTING

```
<160> NUMBER OF SEQ ID NOS: 4

<210> SEQ ID NO 1
<211> LENGTH: 119
<212> TYPE: PRT
<213> ORGANISM: Artificial Sequence
<220> FEATURE:
<223> OTHER INFORMATION: An artificially synthesized polypeptide
      sequence

<400> SEQUENCE: 1

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser
        115

<210> SEQ ID NO 2
<211> LENGTH: 107
<212> TYPE: PRT
<213> ORGANISM: Artificial Sequence
<220> FEATURE:
<223> OTHER INFORMATION: An artificially synthesized polypeptide
      sequence

<400> SEQUENCE: 2

Asp Ile Gln Met Thr Gln Ser Pro Ser Ser Leu Ser Ala Ser Val Gly
1               5                   10                  15

Asp Ser Val Thr Ile Thr Cys Gln Ala Ser Thr Asp Ile Ser Ser His
            20                  25                  30

Leu Asn Trp Tyr Gln Gln Lys Pro Gly Lys Ala Pro Glu Leu Leu Ile
        35                  40                  45

Tyr Tyr Gly Ser His Leu Leu Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu
            100                 105

<210> SEQ ID NO 3
<211> LENGTH: 443
<212> TYPE: PRT
<213> ORGANISM: Artificial Sequence
<220> FEATURE:
<223> OTHER INFORMATION: An artificially synthesized polypeptide
      sequence

<400> SEQUENCE: 3

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140
```

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Ser Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
                260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Phe Arg Val Val Ser Val Leu
        290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
                340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Glu Gly Asn Val Phe Ser Cys Ser Val Met His Glu Ala Leu His Ala
            420                 425                 430

His Tyr Thr Gln Lys Ser Leu Ser Leu Ser Pro
        435                 440

<210> SEQ ID NO 4
<211> LENGTH: 214
<212> TYPE: PRT
<213> ORGANISM: Artificial Sequence
<220> FEATURE:
<223> OTHER INFORMATION: An artificially synthesized polypeptide
      sequence

<400> SEQUENCE: 4

Asp Ile Gln Met Thr Gln Ser Pro Ser Ser Leu Ser Ala Ser Val Gly
1               5                   10                  15

Asp Ser Val Thr Ile Thr Cys Gln Ala Ser Thr Asp Ile Ser Ser His
                20                  25                  30

Leu Asn Trp Tyr Gln Gln Lys Pro Gly Lys Ala Pro Glu Leu Leu Ile
            35                  40                  45

Tyr Tyr Gly Ser His Leu Leu Ser Gly Val Pro Ser Arg Phe Ser Gly
        50                  55                  60
```

```
Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85              90              95

Thr Phe Gly Gln Gly Thr Lys Val Glu Ile Glu Arg Thr Val Ala Ala
            100             105             110

Pro Ser Val Phe Ile Phe Pro Pro Ser Asp Glu Gln Leu Lys Ser Gly
            115             120             125

Thr Ala Ser Val Val Cys Leu Leu Asn Asn Phe Tyr Pro Arg Glu Ala
        130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
                165             170             175

Ser Thr Leu Thr Leu Ser Lys Ala Asp Tyr Glu Lys His Lys Val Tyr
            180             185             190

Ala Cys Glu Val Thr His Gln Gly Leu Ser Ser Pro Val Thr Lys Ser
            195             200             205

Phe Asn Arg Gly Glu Cys
    210
```

ANTI-IL-6 RECEPTOR ANTIBODY-CONTAINING MEDICINAL COMPOSITION FOR PREVENTING POST-SURGICAL ADHESION

CROSS-REFERENCE TO RELATED APPLICATIONS

This application is a U.S. National Phase of PCT Application No. PCT/JP2018/038955, filed Oct. 19, 2018, which claims the benefit of Japanese Patent Application No. 2017-203271, filed Oct. 20, 2017, each of which is incorporated herein by reference in its entirety.

REFERENCE TO SEQUENCE LISTING SUBMITTED ELECTRONICALLY:

The content of the electronically submitted sequence listing (Name: 6663_0134 Sequence_Listing.txt; Size: 8.29 kilobytes; and Date of Creation: Apr. 14, 2020) filed with the application is incorporated herein by reference in its entirety.

TECHNICAL FIELD

The present invention relates to methods and pharmaceutical compositions for suppressing postoperative adhesion formation. Specifically, the present invention relates to methods for suppressing postoperative adhesion formation and pharmaceutical compositions for suppressing postoperative adhesion formation (suppressor of postoperative adhesion), which comprise using an anti-IL-6 receptor antibody (herein, also referred to as anti-IL-6R antibody, IL-6R antibody, or IL-6 receptor antibody) and/or an anti-neutrophil neutralizing antibody (herein, also referred to as a neutralizing antibody against neutrophils).

BACKGROUND ART

Adhesion that occurs after surgical operation is a complication caused at high probability by surgery, although varying in their degree. Adhesion is not a problem when there are no symptoms, but at times, they may cause abdominal pain, intestinal obstruction, infertility, and such, and various measures have been taken to protect from adhesion.

Intestinal adhesion that occurs after intraabdominal surgery often cause postoperative complications such as intestinal obstruction, which is a problem. With regard to the mechanism by which intestinal adhesion is formed after intraabdominal surgery, it is known that fibrin is induced and precipitates due to surgical invasion of the intestinal tract, and adhesion is avoided when the fibrinolytic system is enhanced on fibrin, whereas adhesion is promoted when the coagulation system is enhanced. Furthermore, tissue plasminogen activator (tPA) is known as a factor which enhances the fibrinolytic system, and plasminogen activator inhibitor 1 (PAI-1) is known as a factor which enhances the coagulation system (NPL 1).

In addition, surgical invasion has been reported to induce expression of the neurotransmitter Substance P, weaken the fibrinolytic system, and induce and/or promote intestinal adhesion (NPL 2). Furthermore, it has been disclosed that the use of an antagonist of Substance P receptor NK-1R suppressed intestinal adhesion (NPL 2).

Furthermore, it has been reported that tachykinin, a neuropeptide induced in the intestine through the axonal reflex caused by surgical invasion, stimulates NKT cells that accumulated in the intestinal tract similarly due to surgical invasion and induces IFN-$\gamma$ production, IFN-$\gamma$ enhances PAI-1 expression and suppresses tPA, and thereby adhesion formation is promoted (PTL 1, and NPL 3). On the other hand, administration of an anti-IFN-$\gamma$ antibody or hepatocyte growth factor (HGF) protein has been reported to suppress the induction of PAI-1 and enable prevention of the onset of postoperative intestinal adhesion (PTL 1).

Also, as with postoperative intestinal adhesion, IFN-$\gamma$ has been reported to play an important role in adhesion formation after partial hepatectomy and that formation of adhesion is inhibited when the HGF protein is administered (NPL 4).

As another method for controlling intestinal adhesion, the result of examining the effect of an antibody (anti-IL-6 antibody) against IL-6 (interleukin 6) known to be a multifunctional cytokine has been reported (NPL 5). According to this report, it is asserted that adhesion was controlled by administering an anti-IL-6 antibody to an adhesion model; however, macroscopic pictures and pathological pictures showing the adhesion grade are not disclosed as data supporting this assertion. In addition, the report points out doubts in the appropriateness of the model and the credibility of the significant differences between the results of the control group and the anti-IL-6 antibody-administered group.

CITATION LIST

Patent Literature

PTL 1 U.S. Pat. No. 5,530,635

Non-Patent Literature

NPL 1 Eur. J. Surg. Suppl., 1997, 577, 24-31
NPL 2 Proc. Natl. Acad. Sci. U.S.A, 2004, 101, 9115-9120
NPL 3 Nature medicine vol. 14, no. 4, April 2008, 437-441
NPL 4 British Journal of Surgery vol. 101, Issue 4, March 2014; 398-407
NPL 5 Am Surg. 1996 July; 62(7):569-72

SUMMARY OF INVENTION

Technical Problem

The present invention has been made in view of the above-mentioned circumstances. Technical problem underlying the present invention is to provide novel methods and pharmaceutical compositions for suppressing postoperative adhesion formation.

Solution to Problem

To confirm the suppressive effect of the IL-6-neutralizing antibody on adhesion formation, the present inventors used a mouse model in which adhesion formation is examined on the seventh day after cecal cauterization, and examined the adhesion-suppressing effect of IL-6-neutralizing antibody (1000 µg/20 g mouse: 200-fold dose per body weight as compared to the dose described in NPL 4) administration on the day before surgery, and did not observe any adhesion-suppressing effect at all.

As a result of dedicated examination, the present inventors unexpectedly found out that administration of an anti-IL-6 receptor antibody suppresses formation of intestinal adhesion after surgical operation. In addition, they found that administration of an anti-IL-6 receptor antibody has the effect of suppressing the elevation of neutrophil-inducing chemokine levels caused by surgery, and as a result, an effect of suppressing the migration of neutrophils to the site of surgical invasion was also obtained. Furthermore, they found that administration of neutralizing antibodies against neutrophils can also suppress postoperative adhesion formation. Furthermore, when the effect on wound healing by administration of an anti-IL-6 receptor antibody in a full-thickness skin defect model was examined, no suppressing effect on wound healing was observed.

The present invention is based on such findings, and specifically provides, for example, the following:
- [1] a pharmaceutical composition for suppressing postoperative adhesion, which comprises an anti-IL-6 receptor antibody as an active ingredient;
- [2] the pharmaceutical composition of [1], which is administered to a subject preoperatively;
- [2-2] the pharmaceutical composition of [1], which is administered between 48 hours before surgery to 24 hours after surgery;
- [3] the pharmaceutical composition of [1] or [2], wherein the adhesion is gastrointestinal adhesion or liver adhesion;
- [4] the pharmaceutical composition of [3], wherein the adhesion is intestinal adhesion;
- [4-2] the pharmaceutical composition of any one of [1] to [4], which does not suppress wound healing at an invasion site;
- [5] a pharmaceutical composition for suppressing neutrophil migration, which comprises an anti-IL-6 receptor antibody as an active ingredient;
- [6] the pharmaceutical composition of [5], which is for suppressing migration of neutrophils to a site of surgical invasion; and
- [7] a pharmaceutical composition for suppressing postoperative adhesion, which comprises a neutralizing antibody against neutrophils as an active ingredient.

Furthermore, the present invention also provides the following:
- [1A] a method for suppressing postoperative adhesion, wherein the method comprises administering an anti-IL-6 receptor antibody to a subject;
- [1B] an anti-IL-6 receptor antibody for use in suppressing postoperative adhesion;
- [1C] use of an anti-IL-6 receptor antibody in the manufacture of a pharmaceutical composition for suppressing postoperative adhesion;
- [1D] a suppressor of postoperative adhesion, which comprises an anti-IL-6-receptor antibody as an active ingredient;
- [2A] a method for suppressing neutrophil migration, wherein the method comprises administering an anti-IL-6 receptor antibody to a subject;
- [2B] an anti-IL-6 receptor antibody for use in suppressing neutrophil migration;
- [2C] use of an anti-IL-6 receptor antibody in the manufacture of a pharmaceutical composition for suppressing neutrophil migration;
- [2D] a suppressor of neutrophil migration, which comprises an anti-IL-6-receptor antibody as an active ingredient;
- [3A] a method for suppressing postoperative adhesion, wherein the method comprises administering to a subject a neutralizing antibody against neutrophils;
- [3B] a neutralizing antibody against neutrophils for use in suppressing postoperative adhesion;
- [3C] use of a neutralizing antibody against neutrophils in the manufacture of a pharmaceutical composition for suppressing postoperative adhesion; and
- [3D] a suppressor of postoperative adhesion, which comprises a neutralizing antibody against neutrophils as an active ingredient.

Effects of the Invention

The present inventors succeeded in confirming the effect of suppressing adhesion formation by administering an anti-IL-6 receptor antibody. This finding was unexpected because the above effect was not confirmed when an anti-IL-6 antibody was administered to an animal model of intestinal adhesion. The present inventors also found that neutrophil migration is suppressed by administering an anti-IL-6 receptor antibody. Furthermore, the inventors also found that administration of an anti-IL-6 receptor antibody does not suppress wound healing. Therefore, the pharmaceutical composition of the present invention comprising an anti-IL-6 receptor antibody and/or an anti-neutrophil neutralizing antibody as an active ingredient provides new means that can achieve the effects of suppressing neutrophil migration, and consequently suppressing postoperative adhesion formation.

DESCRIPTION OF EMBODIMENTS

Figure 1:
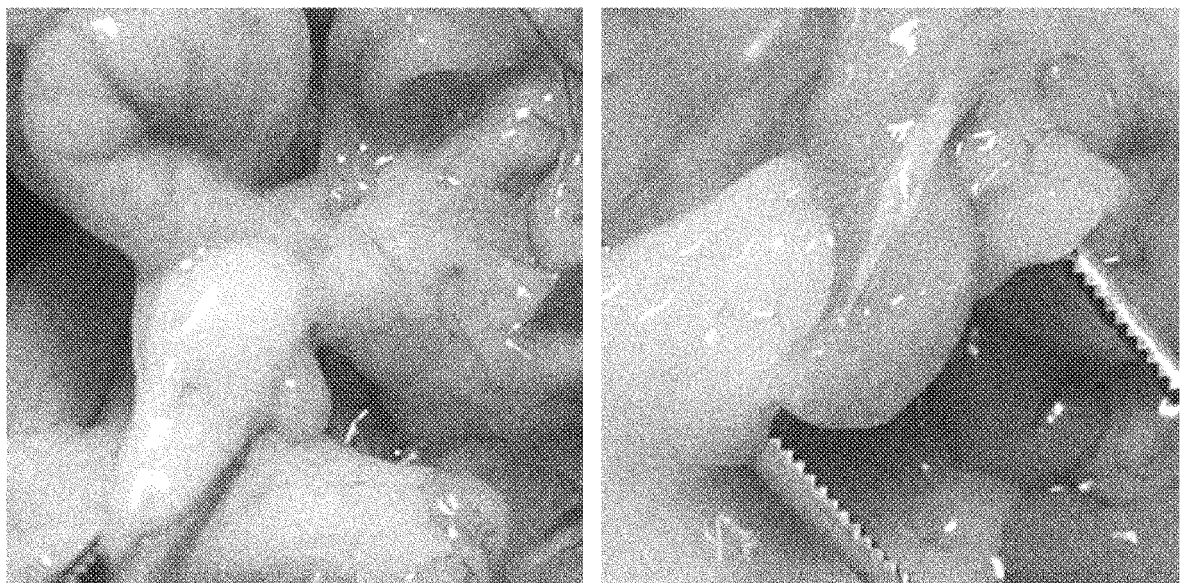
FIG. 1 is a set of photographs of the damaged portion of the intestinal tract of the PBS-administered group.

A pharmaceutical composition of the present invention comprises an anti-IL-6 receptor antibody and/or an anti-neutrophil neutralizing antibody as an active ingredient, and when it is administered to a subject, adhesion formation at the site of surgical invasion can be suppressed. Therefore, pharmaceutical compositions of the present invention can also be described as suppressors of postoperative adhesion (formation).

Furthermore, by administration to a subject, a pharmaceutical composition of the present invention can suppress migration of neutrophils, and consequently suppress infiltration of neutrophils to the site of surgical invasion. Therefore, the pharmaceutical composition of the present invention can also be described as a neutrophil migration suppressor.

Herein, "adhesion" refers to a state in which surfaces of tissues which should be separated from one another are connected or fused by fibrous tissue. Adhesion that occurs after surgical operations is known to occur in the abdomen, chest, and various other sites throughout the living body, and specific examples include, the digestive tract (including the intestine (small and large intestines) and the stomach), liver, uterus, lung, heart, and tendon.

Examples of the "adhesion" of the present invention include, but are not limited to, "gastrointestinal adhesion". "Gastrointestinal adhesion" means adhesion between one part of the digestive tract and another part of this digestive tract as well as adhesion between the digestive tract and another organ. Moreover, while "adhesion" is, for example, "liver adhesion", it is not particularly limited thereto. "Liver adhesion" means adhesion of one part of the liver to another part of the liver as well as adhesion of the liver to another organ. Other examples of "adhesion" include "intestinal adhesion", but are not particularly limited thereto. "Intestinal adhesion" means adhesion between a part of the intestinal tract and another part of this intestinal tract as well as adhesion between the intestinal tract and another organ. In one embodiment, the pharmaceutical composition of the present invention is a pharmaceutical composition for suppressing postoperative intestinal adhesion (a suppressor of postoperative intestinal adhesion), which can suppress the formation of intestinal adhesion caused by surgery involving invasion of the intestinal tract.

Herein, "suppression of adhesion" refers to reducing the formation of adhesion. Suppression of adhesion does not necessarily require complete protection from adhesion formation, and adhesion formation may only be reduced as compared to the state when the pharmaceutical composition of the present invention is not applied. That is, "suppression of adhesion" may be reworded as reduction of adhesion, and indicates, for example, that one or more selected from the frequency, range, and degree of adhesion, are reduced. The "suppression of adhesion" can be evaluated by a known evaluation method. Examples of such an evaluation method include evaluations by score determination using a six-step evaluation by adhesion scores 0 to 5, as described in the Examples herein. "Suppression of adhesion" includes protection from (prevention of) adhesion.

Herein, "suppression of neutrophil migration" does not necessarily require complete protection from neutrophil migration, and neutrophil migration may only be reduced as compared to the state when the pharmaceutical composition of the present invention is not applied. In one embodiment, "suppression of neutrophil migration" refers to suppression of migration of neutrophils to the site of surgical invasion. In another embodiment, "suppression of neutrophil migration" refers to suppression of infiltration of neutrophils at the site of surgical invasion. The "suppression of neutrophil migration" can be evaluated by a known evaluation method. Examples of such an evaluation method include evaluation by immunostaining with a neutrophil marker (rat Ly6G or human CD177) using a tissue section containing the site of invasion as described in the Examples herein.

Herein, "suppression of wound healing" refers to reducing or delaying wound healing at the site of invasion. Suppressing wound healing does not necessarily require complete stop of wound healing at the site of invasion. In one embodiment, application of the pharmaceutical composition of the present invention does not lead to observation of a significant suppressive effect on wound healing as compared to the state when the composition is not applied. Therefore, application of the pharmaceutical composition of the present invention suppresses postoperative adhesion formation and leads to wound healing at the site of invasion. The suppressive effect on wound healing can be tested by confirming wound healing of the postoperative skin suture (specifically, the thoracoabdominal skin suture) of a patient who has been administered the pharmaceutical composition of the present invention.

The pharmaceutical composition of the present invention is administered at a dose at which the active ingredients, the anti-IL-6 receptor antibody and/or anti-neutrophil neutralizing antibody, can suppress adhesion. Suppression of adhesion can be evaluated, for example, by the adhesion grade evaluation method as described in the Examples (see Surgery 120: 866-870, 1996), and when the average value of the adhesion grade is lower than that when the pharmaceutical composition of the present invention was not applied, adhesion is shown to be suppressed. Therefore, the dose of the pharmaceutical composition of the present invention can be appropriately adjusted by using such an index.

In one embodiment, the pharmaceutical composition of the present invention may be formulated as a unit dosage form containing an effective amount of an anti-IL-6 receptor antibody and/or an anti-neutrophil neutralizing antibody. Herein, an "effective amount" refers to an amount at the necessary dose and over the necessary period effective for achieving the desired suppressive or preventive result.

The dose of the pharmaceutical composition of the present invention can be appropriately set according to the condition of the subject of administration, the degree of invasion caused by surgery, the administration method (for example, number of administration times, frequency of administration, timing for administration, and administration route), and the like. In one embodiment, specific examples of the amount of anti-IL-6 receptor antibody contained in the pharmaceutical composition of the present invention per administration are: 2 to 600 mg/kg, 120 to 600 mg/kg, 140 to 600 mg/kg, 160 to 600 mg/kg, 180 to 600 mg/kg, 200 to 600 mg/kg, 220 to 600 mg/kg, 240 to 600 mg/kg, 260 to 600 mg/kg, 280 to 600 mg/kg, 300 to 600 mg/kg, 320 to 600 mg/kg, 340 to 600 mg/kg, 360 to 600 mg/kg, 380 to 600 mg/kg, 400 to 600 mg/kg, 420 to 580 mg/kg, 440 to 560 mg/kg, 460 to 540 mg/kg, 480 to 520 mg/kg, 500 mg/kg, 2 to 40 mg/kg, 2 to 30 mg/kg, 10 to 40 mg/kg, 20 to 40 mg/kg, 2 to 20 mg/kg, 0.5 to 10 mg/kg, 2 to 10 mg/kg, 2 to 8 mg/kg, 8 mg/kg, and 2 mg/kg; or alternatively, 50 to 800 mg, 10 to 240 mg, 50 to 300 mg, 100 to 300 mg, 120 to 250 mg, 150 to 200 mg, 80 to 200 mg, 80 to 160 mg, 162 mg, and 120 mg; but are not limited thereto.

The pharmaceutical composition of the present invention is preferably administered preoperatively, and such administration can prevent adhesion formation at the site of surgical invasion. Therefore, the pharmaceutical composition of the present invention can also be described as a pharmaceutical composition for preventing postoperative adhesion (formation), an agent for preventing postoperative adhesion (formation), and such.

The timing for administration of the pharmaceutical composition of the present invention can be appropriately set according to the condition of the subject of administration, the degree of invasion that will be caused by surgery, the administration method, and the like, and examples include the period from 48 hours before surgical operation to 24 hours after the operation, such as, 36 to 24 hours before operation, or for example 24 hours before operation, but are not limited thereto.

The number of doses and frequency of administration of the pharmaceutical composition of the present invention can be appropriately set according to the condition of the subject of administration, the degree of invasion that will be caused by surgery, the administration method (for example, dose, timing for administration, and administration route), and the like, and examples include once or several times between 48 hours before surgical operation and 24 hours after the operation, such as once 24 hours before surgery. Such administration enables prevention of adhesion formation at the site of surgical invasion.

The subject of administration of the pharmaceutical composition of the present invention is a mammal. Mammals include, but are not limited to, domestic animals (for example, cows, sheep, cats, dogs, and horses), primates (for example, humans and non-human primates such as monkeys), rabbits, and rodents (for example, mice and rats). In a particular embodiment, the subject of administration of the pharmaceutical composition of the present invention is a human. In another embodiment, the subject of administration is a non-human mammal.

The pharmaceutical composition of the present invention comprises, as an active ingredient, an antibody against the IL-6 receptor and/or a neutralizing antibody against neutrophils.

The IL-6 receptor, which is a ligand-binding protein with a molecular weight of approximately 80 kD, binds to IL-6 to form an IL-6/IL-6 receptor complex. Then, binding of this complex to gp130, a membrane protein with a molecular weight of approximately 130 kD involved in non-ligand binding signal transduction, causes the biological activity of IL-6 to be transduced into cells.

In another embodiment, the present invention relates to an anti-IL-6 receptor antibody for use in suppressing postoperative adhesion. Alternatively, the present invention relates to a method for suppressing postoperative adhesion in a subject, which comprises administering an effective amount of an anti-IL-6 receptor antibody to the subject, or an anti-IL-6 receptor antibody for use in the method. The "subject" in such embodiments is an individual who is to undergo a surgical operation. The individual is preferably a human but may be a non-human mammal. In one such embodiment, the method further comprises a step of administering to the subject an effective amount of at least one additional pharmaceutical agent (for example, an anti-neutrophil antibody). The combined use of the anti-IL-6 receptor antibody and the additional pharmaceutical agent includes co-administration (two or more pharmaceutical agents are contained in the same or separate formulations) and separate administration, and in the case of separate administration, administration of the anti-IL-6 receptor antibody may be performed prior to, simultaneously with, and/or subsequent to administration of the additional pharmaceutical agent.

Alternatively, the present invention relates to a pharmaceutical composition for suppressing postoperative adhesion, which comprises an effective amount of an anti-IL-6 receptor antibody. Alternatively, the present invention relates to the use of an anti-IL-6 receptor antibody in the manufacture of a pharmaceutical for suppressing postoperative adhesion. Alternatively, the present invention relates to the use of an anti-IL-6 receptor antibody in the suppression of postoperative adhesion. Alternatively, the present invention relates to a method for producing a pharmaceutical composition for suppressing postoperative adhesion, which comprises a step of mixing an anti-IL-6 receptor antibody and a pharmaceutically acceptable carrier. Such a pharmaceutical or pharmaceutical composition may comprise, in addition to the anti-IL-6 receptor antibody and the pharmaceutically acceptable carrier, at least one additional pharmaceutical agent (for example, an anti-neutrophil antibody).

In a further embodiment, the invention relates to an anti-IL-6 receptor antibody for use in suppressing neutrophil migration. Alternatively, the present invention relates to a method for suppressing neutrophil migration in a subject, which comprises administering an effective amount of an anti-IL-6 receptor antibody to the subject, or an anti-IL-6 receptor antibody for use in this method. The "subject" in such embodiments is an individual who is to undergo a surgical operation. The individual is preferably a human, but may be a non-human mammal. In one such embodiment, the method suppresses neutrophil migration (infiltration) to the site of surgical invasion in the subject. In one such embodiment, the method further comprises a step of administering to the subject an effective amount of at least one additional pharmaceutical agent (for example, an anti-neutrophil antibody). The combined use of the anti-IL-6 receptor antibody and the additional pharmaceutical agent includes co-administration (two or more pharmaceutical agents are contained in the same or separate formulations) and separate administration, and in the case of separate administration, administration of the anti-IL-6 receptor antibody may be performed prior to, simultaneously with, and/or subsequent to administration of the additional pharmaceutical agent.

Alternatively, the present invention relates to a pharmaceutical composition for suppressing neutrophil migration, which comprises an effective amount of an anti-IL-6 receptor antibody. Alternatively, the present invention relates to the use of an anti-IL-6 receptor antibody in the manufacture of a pharmaceutical for suppressing neutrophil migration. Alternatively, the present invention relates to the use of an anti-IL-6 receptor antibody in the suppression of neutrophil migration. Alternatively, the present invention relates to a method for producing a pharmaceutical composition for suppressing neutrophil migration, which comprises a step of mixing an anti-IL-6 receptor antibody and a pharmaceutically acceptable carrier. Such a pharmaceutical or pharmaceutical composition may comprise, in addition to the anti-IL-6 receptor antibody and the pharmaceutically acceptable carrier, at least one additional pharmaceutical agent (for example, an anti-neutrophil antibody).

An anti-IL-6 receptor antibody used in the present invention can be obtained as either a polyclonal or monoclonal antibody using known methods. A monoclonal antibody derived from a mammal is particularly preferred for the anti-IL-6 receptor antibody used in the present invention. The monoclonal antibodies derived from a mammal include those produced by a hybridoma and those produced by a host transformed with an expression vector containing an antibody gene using genetic engineering methods. By binding to an IL-6 receptor, this antibody inhibits the binding of IL-6 to an IL-6 receptor, and blocks transduction of the IL-6 biological activity into cells.

Examples of such an antibody include the MR16-1 antibody (Tamura, T. et al. Proc. Natl. Acad. Sci. USA (1993) 90, 11924-11928), PM-1 antibody (Hirata, Y et al., J. Immunol. (1989) 143, 2900-2906), AUK12-20 antibody, AUK64-7 antibody, and AUK146-15 antibody (International Patent Application Publication No. WO 92-19759). Among them, the PM-1 antibody is listed as an example of a preferred monoclonal antibody against the human IL-6 receptor, and the MR16-1 antibody is listed an example of a preferred monoclonal antibody against the mouse IL-6 receptor.

Basically, hybridomas that produce an anti-IL-6 receptor monoclonal antibody can be produced using known techniques as below. Specifically, the hybridomas can be produced by performing immunization by a conventional immunization method using an IL-6 receptor as a sensitizing antigen, fusing the resulting immune cells with known parent cells by a conventional cell fusion method, and then screening for cells that produce monoclonal antibodies using a conventional screening method.

Specifically, anti-IL-6 receptor antibodies can be produced as below. A human IL-6 receptor or mouse IL-6 receptor to be used as a sensitizing antigen for obtaining antibodies can be obtained by, for example, using the IL-6 receptor gene and/or amino acid sequences respectively disclosed in European Patent Application Publication No. EP 325474 and Japanese Patent Application Kokai Publication No. (JP-A) H03-155795 (unexamined, published Japanese patent application).

There are two types of IL-6 receptor proteins: one expressed on the cell membrane and the other separated from the cell membrane (soluble IL-6 receptor) (Yasukawa, K. et al., J. Biochem. (1990) 108, 673-676). The soluble IL-6 receptor is essentially composed of the extracellular region of the IL-6 receptor bound to the cell membrane, and differs from the membrane-bound IL-6 receptor in that it lacks the transmembrane region or both the transmembrane and intracellular regions. Any IL-6 receptor may be employed as the IL-6 receptor protein, as long as it can be used as a sensitizing antigen for producing an anti-IL-6 receptor antibody to be used in the present invention.

After an appropriate host cell is transformed with a known expression vector system inserted with an IL-6 receptor gene sequence, the target IL-6 receptor protein is purified from the inside of the host cell or from the culture supernatant using a known method. This purified IL-6 receptor protein may be used as a sensitizing antigen. Alternatively, a cell expressing the IL-6 receptor or a fusion protein of the IL-6 receptor protein and another protein may be used as a sensitizing antigen.

Mammals to be immunized with a sensitizing antigen are not particularly limited, but are preferably selected in consideration of the compatibility with parent cells used for cell fusion. Typically, rodents such as mice, rats, and hamsters are used.

Animals are immunized with a sensitizing antigen according to known methods. Typically, immunization is performed by, for example, intraabdominal or subcutaneous injection of the sensitizing antigen to a mammal. Specifically, it is preferable to dilute or suspend the sensitizing antigen in phosphate-buffered saline (PBS), physiological saline, and such, to an appropriate volume, and mix it with an appropriate amount of a conventional adjuvant such as Freund's complete adjuvant if desired and emulsify, and then administer to the mammal every four to 21 days for several times. An appropriate carrier may also be used for immunization with the sensitizing antigen.

After immunizing the mammal in this manner, and confirming that the serum level of a desired antibody has increased, immunized cells are removed from the mammal and subjected to cell fusion. Spleen cells are particularly preferred as the immunized cells to be subjected to cell fusion.

Myeloma cells from mammals are used as parent cells to be fused with the immunized cells. So far, various known cell lines such as P3X63Ag8.653 (Keamey, J. F. et al., J. Immunol (1979) 123, 1548-1550), P3X63Ag8U.1 (Current Topics in Microbiology and Immunology (1978) 81, 1-7), NS-1 (Kohler, G. and Milstein, C., Eur. J. Immunol. (1976) 6, 511-519), MPC-11 (Margulies, D. H. et al., Cell (1976) 8, 405-415), SP2/0 (Shulman, M. et al., Nature (1978) 276, 269-270), FO (de St. Groth, S. F. et al., J. Immunol. Methods (1980) 35, 1-21), S194 (Trowbridge, I. S., J. Exp. Med. (1978) 148, 313-323), and R210 (Galfre, G. et al., Nature (1979) 277, 131-133) are suitably used.

Basically, cell fusion of the aforementioned immune cells with myeloma cells can be performed according to known methods such as the method of Milstein et al. (Kohler, G. and Milstein, C., Methods Enzymol. (1981) 73, 3-46).

More specifically, the cell fusion is performed, for example, in a conventional nutrient culture medium in the presence of a cell fusion promoter. For example, polyethylene glycol (PEG) or Sendai virus (HVJ) is used as the fusion promoter, and if desired, an adjuvant such as dimethyl sulfoxide can be further added for use in improving the fusion efficiency.

The ratio of immune cells to myeloma cells used is preferably, for example, 1 to 10 immune cells for each myeloma cell. The culture medium used for the cell fusion is, for example, an RPMI1640 or MEM culture medium suitable for the proliferation of the myeloma cell lines. Other conventional culture media used for this type of cell culture can also be used. Furthermore, serum supplements such as fetal calf serum (FCS) can also be used in combination.

For cell fusion, the fusion cells (hybridomas) of interest are formed by thoroughly mixing predetermined amounts of the aforementioned immune cell and myeloma cell in the aforementioned culture medium, adding a PEG solution (for example, a solution of PEG with an average molecular weight of about 1,000 to 6,000) pre-heated to about 37° C., usually at a concentration of 30% to 60% (w/v), and then mixing them. Then, cell fusion agents and such that are unsuitable for the growth of hybridomas can be removed by repeating the operation of sequentially adding an appropriate culture medium and removing the supernatant by centrifugation.

The hybridomas are selected by culturing in a general selection culture medium, for example, the HAT culture medium (a culture medium containing hypoxanthine, aminopterin, and thymidine). Culturing in the HAT culture medium is continued for a sufficient period, generally from several days to several weeks, to kill cells other than the hybridomas of interest (unfused cells). Then, a standard limiting dilution method is performed to screen for and clone hybridomas that produce an antibody of interest.

Besides obtaining the hybridomas by immunizing non-human animals with an antigen, desired human antibodies having a binding activity to a desired antigen or antigen-expressing cell can be obtained by sensitizing a human lymphocyte with a desired antigen protein or antigen-expressing cell in vitro, and fusing the sensitized B lymphocyte with a human myeloma cell such as U266 (see, Japanese Patent Application Kokoku Publication No. (JP-B) H01-59878 (examined, approved Japanese patent application published for opposition)). Further, an antigen or antigen-expressing cell may be administered to a transgenic animal having a repertoire of human antibody genes, and then a desired human antibody may be obtained following the aforementioned method (see, International Patent Application Publication Nos. WO 93/12227, WO 92/03918, WO 94/02602, WO 94/25585, WO 96/34096, and WO 96/33735).

The hybridomas prepared as such that produce monoclonal antibodies can be subcultured in a conventional culture medium and stored in liquid nitrogen for a long period.

To obtain monoclonal antibodies from the hybridomas, the following methods may be employed: culturing the hybridomas according to conventional methods and obtaining the antibodies as a culture supernatant or proliferating the hybridomas by administering them to a compatible mammal and obtaining the antibodies from ascites; and so on. The former method is suitable for obtaining antibodies with high purity, and the latter is suitable for large-scale antibody production.

For example, hybridomas that produce anti-IL-6 receptor antibodies can be prepared by the method disclosed in JP-A (Kokai) H03-139293. Such a preparation can be carried out by injecting hybridomas that produce PM-1 antibodies into the abdominal cavity of a BALB/c mouse, obtaining ascites, and then purifying the PM-1 antibodies from the ascites; or by culturing the hybridomas in an appropriate medium (such as an RPMI 1640 medium containing 10% fetal bovine serum, and 5% BM-Condimed H1 (Boehringer Mannheim); the hybridoma SFM medium (GIBCO-BRL); or the PFHM-II medium (GIBCO-BRL)) and then purifying the PM-1 antibodies from the culture supernatant.

Recombinant antibodies can be used as the monoclonal antibodies of the present invention, wherein the recombinant antibodies are produced using genetic recombination techniques by cloning an antibody gene from a hybridoma, inserting the gene into an appropriate vector, and then introducing the vector into a host (see, for example, Borrebaeck, C. A. K. and Larrick, J. W., THERAPEUTIC MONOCLONAL ANTIBODIES, Published in the United Kingdom by MACMILLAN PUBLISHERS LTD, 1990).

More specifically, mRNAs coding for antibody variable (V) regions are isolated from cells that produce antibodies of interest, such as hybridomas. mRNAs can be isolated by preparing total RNAs according to known methods, such as the guanidine ultracentrifugation method (Chirgwin, J. M. et al., Biochemistry (1979) 18, 5294-5299) and the AGPC method (Chomczynski, P. et al., Anal. Biochem. (1987) 162, 156-159), and preparing mRNAs using an mRNA Purification Kit (Pharmacia) and such. Alternatively, mRNAs can be directly prepared using the QuickPrep mRNA Purification Kit (Pharmacia).

cDNAs of the antibody V regions are synthesized from the obtained mRNAs using reverse transcriptase. cDNAs may be synthesized using the AMV Reverse Transcriptase First-strand cDNA Synthesis Kit and such. Further, to synthesize and amplify the cDNAs, the 5'-RACE method (Frohman, M. A. et al., Proc. Natl. Acad. Sci. USA (1988) 85, 8998-9002; Belyavsky, A. et al., Nucleic Acids Res. (1989) 17, 2919-2932) using 5'-Ampli FINDER RACE Kit (Clontech) and PCR may be used. A DNA fragment of interest is purified from the obtained PCR products and then ligated with a vector DNA. Then, a recombinant vector is prepared by using the above, and introduced into *Escherichia coli* and such, and then its colonies are selected to prepare a desired recombinant vector. The nucleotide sequence of the DNA of interest is confirmed by a known method such as the dideoxy method.

When a DNA encoding the V region of the antibody of interest is obtained, the DNA is ligated with a DNA encoding the constant region (C region) of a desired antibody, and inserted into an expression vector. Alternatively, a DNA encoding an antibody V region may be inserted into an expression vector comprising a DNA of an antibody C region.

To produce an antibody to be used in the present invention, an antibody gene is inserted into an expression vector such that it is expressed under the control of an expression-regulating region such as an enhancer and promoter, as described below. Then, the antibody can be expressed by transforming a host cell with this expression vector.

In the present invention, artificially modified recombinant antibodies, for example, chimeric antibodies, humanized antibodies, or human antibodies can be used, for example, to reduce heteroantigenicity against humans. These modified antibodies can be prepared using known methods.

A chimeric antibody can be obtained by ligating a DNA encoding an antibody V region obtained as above with a DNA encoding a human antibody C region, inserting it into an expression vector, and introducing the vector into a host to produce the chimeric antibody (see, European Patent Application Publication No. EP 125023; International Patent Application Publication No. WO 92-19759). This known method can be used to obtain chimeric antibodies useful for the present invention.

Humanized antibodies are also referred to as reshaped human antibodies or antibodies made into the human type. They are produced by transplanting the complementarity determining regions (CDRs) of an antibody from a non-human mammal (for example, a mouse) into the CDRs of a human antibody. General methods for this gene recombination are also known (see, European Patent Application Publication No. EP 125023, International Patent Application Publication No. WO 92-19759).

More specifically, DNA sequences designed to ligate the CDRs of a mouse antibody with the framework regions (FRs) of a human antibody are synthesized by PCR from several oligonucleotides produced to contain overlapping portions at their termini. The obtained DNA is ligated with a DNA encoding a human antibody C region and inserted into an expression vector, and the expression vector is introduced into a host to produce the humanized antibody (see, European Patent Application Publication No. EP 239400, International Patent Application Publication No. WO 92-19759).

Human antibody FRs to be ligated via the CDRs are selected so that the CDRs form satisfactory antigen binding sites. The amino acid(s) within the framework regions of the antibody variable regions may be substituted as necessary so that the CDRs of the reshaped human antibody form appropriate antigen binding sites (Sato, K. et al., Cancer Res. (1993) 53, 851-856).

Human antibody C regions are used for the chimeric and humanized antibodies. Examples of human antibody C regions include Cγ, and for example, Cγ1, Cγ2, Cγ3, or Cγ4 may be used. Furthermore, to improve the stability of the antibodies or their production, the human antibody C regions may be modified.

Chimeric antibodies are composed of the variable region of an antibody derived from a non-human mammal and the C region derived from a human antibody; and humanized antibodies are composed of the CDRs of an antibody derived from a non-human mammal and the framework regions and C regions derived from a human antibody. Their antigenicity in the human body is reduced, and thus they are useful as antibodies for use in the present invention.

Preferred specific examples of humanized antibodies for use in the present invention include a humanized PM-1 antibody (see, International Patent Application Publication No. WO 92-19759).

Furthermore, in addition to the aforementioned methods for obtaining human antibodies, techniques for obtaining human antibodies by panning using a human antibody library are also known. For example, the variable region of a human antibody can be expressed on a phage surface as a single chain antibody (scFv) by using the phage display method, and antigen-binding phages can then be selected. By analyzing the genes of the selected phages, the DNA sequence encoding the variable region of the human antibody which binds to the antigen can be determined. Once the DNA sequence of an scFv which binds to the antigen is revealed, an appropriate expression vector comprising the sequence can be prepared to obtain a human antibody. These methods are already known, and the publications, WO 92/01047, WO 92/20791, WO93/06213, WO 93/11236, WO 93/19172, WO 95/01438, and WO 95/15388, can be used as references.

The antibody gene constructed as described above can be expressed according to known methods. When a mammalian cell is used, the antibody gene can be expressed by using a DNA in which a commonly used effective promoter, the antibody gene to be expressed, and a poly A signal on the 3' side (downstream) of the antibody gene are operatively linked together, or by using a vector comprising the DNA. Examples of a promoter/enhancer include the human cytomegalovirus immediate early promoter/enhancer.

Furthermore, other promoters/enhancers that can be used for expressing the antibodies for use in the present invention include viral promoters/enhancers from retroviruses, polyoma viruses, adenoviruses, simian virus 40 (SV40), and such; and mammalian cell-derived promoters/enhancers such as human elongation factor 1α (HEF1α). The expression can be easily performed, for example, by following the method in Mulligan et al. (Mulligan, R. C. et al., Nature (1979) 277, 108-114) when using the SV40 promoter/enhancer, or by following the method in Mizushima et al. (Mizushima, S. and Nagata S., Nucleic Acids Res. (1990) 18, 5322) when using the HEF1α promoter/enhancer.

When E. coli is used, the antibody gene can be expressed by operatively linking a commonly used effective promoter, a signal sequence for antibody secretion, and the antibody gene to be expressed. Examples of the promoter include a lacZ promoter and an araB promoter. A lacZ promoter can be used according to the method of Ward et al. (Ward, E. S. et al., Nature (1989) 341, 544-546; Ward, E. S. et al., FASEB J. (1992) 6, 2422-2427); and an araB promoter can be used according to the method of Better et al. (Better, M. et al., Science (1988) 240, 1041-1043).

When the antibody is produced into the periplasm of E. coli, the pel B signal sequence (Lei, S. P. et al., J. Bacteriol. (1987) 169, 4379-4383) may be used as a signal sequence for antibody secretion. The antibody produced into the periplasm is isolated, and then appropriately refolded into the antibody structure to be used (see, for example, WO 96/30394).

As the replication origin, those derived from SV40, polyoma virus, adenovirus, bovine papilloma virus (BPV) and such may be used. In addition, to increase the gene copy number in a host cell system, the expression vector may comprise the aminoglycoside phosphotransferase (APH) gene, thymidine kinase (TK) gene, E. coli xanthine-guanine phosphoribosyltransferase (Ecogpt) gene, dihydrofolate reductase (dhfr) gene, and such, as a selection marker.

Any production system may be used to prepare the antibodies for use in the present invention. The production systems for antibody preparation include in vitro and in vivo production systems. In vitro production systems include those using eukaryotic cells or those using prokaryotic cells.

When eukaryotic cells are used, the production systems include those using animal cells, plant cells, or fungal cells. Such animal cells include (1) mammalian cells such as CHO, COS, myeloma, baby hamster kidney (BHK), HeLa, and Vero; (2) amphibian cells such as Xenopus oocytes; and (3) insect cells such as sf9, sf21, and Tn5. Known plant cells include cells derived from Nicotiana tabacum, which may be cultured in callus. Known fungal cells include yeasts such as Saccharomyces (e.g., Saccaromyces cerevisiae) and mold fungi such as Aspergillus (e.g., Aspergillus niger).

When prokaryotic cells are used, production systems include those using bacterial cells. Known bacterial cells include E. coli and Bacillus subtilis.

Antibodies can be obtained by introducing the antibody gene of interest into these cells by transformation, and then culturing the transformed cells in vitro. Cells are cultured according to known methods. For example, DMEM, MEM, RPMI 1640, or IMDM may be used as the culture medium, and serum supplements such as fetal calf serum (FCS) may be used in combination. Alternatively, cells introduced with the antibody gene may be transferred into the abdominal cavity and such of an animal to produce the antibodies in vivo.

Meanwhile, in vivo production systems include those using animals or those using plants. When using animals, production systems include those using mammals or insects.

Mammals that can be used include goats, pigs, sheep, mice, and bovines (Vicki Glaser, SPECTRUM Biotechnology Applications, 1993). Further, insects that can be used include silkworms. When using plants, tobacco and such may be used.

An antibody gene is introduced into these animals or plants, and the antibodies are produced in the body of the animals or plants and then recovered. For example, an antibody gene can be prepared as a fusion gene by inserting it into the middle of a gene encoding a protein uniquely produced into milk, such as goat R3 casein. DNA fragments comprising the fusion gene, which includes the inserted antibody gene, are injected into goat embryos, and the embryos are introduced into female goats. The desired antibodies are obtained from milk produced by transgenic goats born from the goats that received the embryos, or their progenies. When appropriate, the transgenic goats may be given hormones to increase the volume of milk containing the desired antibodies that they produce (Ebert, K. M. et al., Bio/Technology (1994) 12, 699-702).

When silkworms are used, the silkworms are infected with a baculovirus inserted with the antibody gene of interest, and the desired antibodies are obtained from the body fluids of these silkworms (Maeda, S. et al., Nature (1985) 315, 592-594). Moreover, when tobacco is used, the antibody gene of interest is inserted into a plant expression vector such as pMON530, and the vector is introduced into bacteria such as *Agrobacterium tumefaciens*. This bacterium is used to infect tobacco such as *Nicotiana tabacum*, and then the desired antibody is obtained from the leaves of this tobacco (Julian, K.-C. Ma et al., Eur. J. Immunol. (1994) 24, 131-138).

When producing antibodies using in vitro or in vivo production systems as described above, DNAs encoding an antibody heavy chain (H chain) and light chain (L chain) may be inserted into separate expression vectors, and a host is then co-transformed with the vectors. Alternatively, the H chain-encoding DNA and L chain-encoding DNA may be inserted into a single expression vector for transforming a host (see International Patent Application Publication No. WO 94-11523).

The antibodies used in the present invention may be antibody fragments or modified products thereof, as long as they can be suitably used in the present invention. For example, antibody fragments include Fab, F(ab')2, Fv, and single chain Fv (scFv) in which the Fvs of the H and L chains are linked via an appropriate linker.

Specifically, the antibody fragments are produced by treating antibodies with enzymes such as papain or pepsin, or alternatively, by constructing genes encoding these antibody fragments and introducing them into expression vectors, and then expressing the vectors in appropriate host cells (see, for example, Co, M. S. et al., J. Immunol. (1994) 152, 2968-2976; Better, M. & Horwitz, A. H., Methods in Enzymology (1989) 178, 476-496; Plueckthun, A. & Skerra, A., Methods in Enzymology (1989) 178, 497-515; Lamoyi, E., Methods in Enzymology (1989) 121, 652-663; Rousseaux, J. et al., Methods in Enzymology (1989) 121, 663-666; and Bird, R. E. et al., TIBTECH (1991) 9, 132-137).

An scFv can be obtained by linking the H-chain V region and the L-chain V region of an antibody. In this scFv, the H-chain V region and the L-chain V region are linked via a linker, preferably via a peptide linker (Huston, J. S. et al., Proc. Natl. Acad. Sci. USA (1988) 85, 5879-5883). The V regions of the H and L chains in an scFv may be derived from any of the antibodies described above. Peptide linkers for linking the V regions include, for example, an arbitrary single chain peptide consisting of 12 to 19 amino acid residues.

A DNA encoding an scFv can be obtained by amplifying a DNA portion that encodes the desired amino acid sequence in template sequences with PCR using a primer pair which defines the termini of the portion, wherein a DNA encoding an H chain or an H-chain V region and a DNA encoding an L chain or an L-chain V region of the aforementioned antibodies are used as the templates, and then further amplifying the amplified DNA portion with a DNA that encodes a peptide linker portion and a primer pair that defines both ends of the linker so that it may be linked to each of the H and L chains.

Once an scFv-encoding DNA has been prepared, an expression vector comprising the DNA and a host transformed with the expression vector can be obtained according to conventional methods. In addition, an scFv can be obtained according to conventional methods by using the host.

Similarly to the above, the antibody fragments can be produced by obtaining their genes, expressing them, and then using a host. An "antibody" as used herein encompasses such antibody fragments.

Antibodies bound to various molecules such as polyethylene glycol (PEG) may also be used as modified antibodies. An "antibody" as used herein encompasses such modified antibodies. These modified antibodies can be obtained by chemically modifying the obtained antibodies. Such methods are already established in the art.

Antibodies produced and expressed as above can be isolated from the inside or outside of the cells or from the hosts, and then purified to homogeneity. The antibodies for use in the present invention can be isolated and purified by affinity chromatography. Columns used for the affinity chromatography include protein A columns and protein G columns. Carriers used for the protein A columns include HyperD, POROS, and Sepharose F. F. Other methods used for the isolation and/or purification of ordinary proteins may be used without limitation.

For example, the antibodies used for the present invention may be isolated and purified by appropriately selecting and combining chromatographies other than the above-described affinity chromatography, filtration, ultrafiltration, salting-out, dialysis, and such. Examples of chromatographies include ion-exchange chromatography, hydrophobic chromatography, and gel filtration. These chromatographies can be applied to high performance liquid chromatography (HPLC). Alternatively, reverse phase HPLC may be used.

The concentration of the antibodies obtained as above can be determined by absorbance measurement, ELISA, and such. Specifically, when using absorbance measurement, the concentration can be determined by appropriately diluting the antibody solution with PBS(−), measuring its absorbance at 280 nm, and calculating the concentration by using the conversion factor 1.35 OD/1 mg/ml. Alternatively, when using ELISA, the concentration can be determined as below. Specifically, 100 μl of goat anti-human IgG (TAG) diluted to 1 μg/ml with 0.1 M bicarbonate buffer (pH 9.6) is added to a 96-well plate (Nunc) and incubated overnight at 4° C. to immobilize the antibody. After blocking, 100 μl of an appropriately diluted antibody to be used in the present invention or an appropriately diluted sample comprising the antibody, or human IgG (CAPPEL) as a standard is added, and the plate is incubated for one hour at room temperature.

After washing, 100 μl of 5,000× diluted alkaline phosphatase-labeled anti-human IgG (BIO SOURCE) is added, and the plate is incubated for one hour at room temperature. After another wash, the substrate solution is added, the plate is incubated, and absorbance at 405 nm is measured using Microplate Reader Model 3550 (Bio-Rad) to calculate the concentration of the antibody of interest.

The antibodies used in the present invention may be conjugate antibodies that are bound to various molecules such as polyethylene glycol (PEG), radioactive substances, and toxins. Such conjugate antibodies can be obtained by chemically modifying the obtained antibodies. Methods for antibody modification have been already established in this field. Accordingly, the term "antibody" as used herein encompasses such conjugate antibodies.

Preferred examples of an "IL-6 receptor antibody" of the present invention include tocilizumab which is a humanized anti-IL-6 receptor IgG1 antibody, and humanized anti-IL-6 receptor antibodies produced by modifying the variable and constant regions of tocilizumab, specifically, an antibody containing a heavy-chain variable region comprising the sequence of SEQ ID NO: 1 and a light-chain variable region comprising the sequence of SEQ ID NO: 2. A more preferable example is an antibody containing a heavy chain comprising the sequence of SEQ ID NO: 3 (heavy chain of SA237) and a light chain comprising the sequence of SEQ ID NO: 4 (light chain of SA237). SA237 is particularly preferred.

Such antibodies can be obtained according to the methods described in WO2010/035769, WO2010/107108, WO2010/106812, and such. Specifically, antibodies can be produced using genetic recombination techniques known to those skilled in the art, based on the sequence of the above-mentioned IL-6 receptor antibody (see, for example, Borrebaeck C A K and Larrick J W, THERAPEUTIC MONOCLONAL ANTIBODIES, Published in the United Kingdom by MACMILLAN PUBLISHERS LTD, 1990). A recombinant antibody can be obtained by cloning a DNA encoding the antibody from a hybridoma or an antibody-producing cell such as an antibody-producing sensitized lymphocyte, inserting the DNA into an appropriate vector, and introducing the vector into a host (host cell) to produce the antibody.

Such antibodies can be isolated and purified using isolation and purification methods conventionally used for antibody purification, without limitation. For example, the antibodies can be isolated and purified by appropriately selecting and combining column chromatography, filtration, ultrafiltration, salting-out, solvent precipitation, solvent extraction, distillation, immunoprecipitation, SDS-polyacrylamide gel electrophoresis, isoelectric focusing, dialysis, recrystallization, and such.

Herein, examples of neutralizing antibodies against neutrophils (anti-neutrophil neutralizing antibodies) include antibodies that bind to an antigen expressed on neutrophils. Specific examples include, but are not limited to, antibodies against Ly6G present on mouse neutrophils. Other examples include antibodies against CD177 expressed on human neutrophils (Blood. 2012 Aug. 16; 120 (7): 1489-1498).

Herein, the terms "pharmaceutical composition" and "suppressor" indicate preparations in a form that allows the biological activity of the active ingredient contained therein to exert an effect, which do not contain any additional ingredient that is toxic to an unacceptable degree to the subject to which a formulation is administered. The pharmaceutical composition of the present invention may comprise more than one active ingredient, if that is necessary for its suppressive or preventive purpose. Those with complementary activities that do not adversely affect each other are preferred. For example, the pharmaceutical composition of the present invention may contain an anti-neutrophil neutralizing antibody as an active ingredient in addition to an anti-IL-6 receptor antibody. Such active ingredients are present in suitable combination in amounts that are effective for the intended purpose.

Pharmaceutical compositions of the present invention used for suppressive or preventive purposes can be formulated to produce freeze-dried formulations or solution formulations by mixing, if necessary, with suitable pharmaceutically acceptable carriers, vehicles, and such. The suitable pharmaceutically acceptable carriers and vehicles include, for example, sterilized water, physiological saline, stabilizers, excipients, antioxidants (such as ascorbic acid), buffers (such as phosphate, citrate, histidine, and other organic acids), antiseptics, surfactants (such as PEG and Tween), chelating agents (such as EDTA), and binders. Other low-molecular-weight polypeptides, proteins such as serum albumin, gelatin, and immunoglobulins, amino acids such as glycine, glutamine, asparagine, glutamic acid, aspartic acid, methionine, arginine, and lysine, sugars and carbohydrates such as polysaccharides and monosaccharides, and sugar alcohols such as mannitol and sorbitol may also be contained. When preparing an aqueous solution for injection, physiological saline and isotonic solutions comprising glucose and other adjuvants such as D-sorbitol, D-mannose, D-mannitol, and sodium chloride may be used; and appropriate solubilizers such as alcohol (for example, ethanol), polyalcohols (such as propylene glycol and PEG), and nonionic surfactants (such as polysorbate 80, polysorbate 20, poloxamer 188, and HCO-50) may be used in combination. By mixing hyaluronidase into the formulation, a larger fluid volume can be administered subcutaneously (Expert Opin. Drug Deliv. 2007 July; 4(4): 427-40). Furthermore, syringes may be prefilled with the pharmaceutical composition of the present invention. Solution formulations can be prepared according to the method described in WO2011/090088.

If necessary, the pharmaceutical compositions of the present invention may be encapsulated in microcapsules (e.g., those made of hydroxymethylcellulose, gelatin, and poly(methylmetacrylate)), or incorporated into colloidal drug delivery systems (e.g., liposomes, albumin microspheres, microemulsion, nanoparticles, and nanocapsules) (see, for example, "Remington's Pharmaceutical Science 16th edition", Oslo Ed. (1980)). Methods for preparing the pharmaceutical agents as controlled-release pharmaceutical agents are also known, and such methods may be applied to the pharmaceutical compositions of the present invention (Langer et al., J. Biomed. Mater. Res. 15: 267-277 (1981); Langer, Chemtech. 12: 98-105 (1982); U.S. Pat. No. 3,773,919; European Patent Application Publication No. EP 58,481; Sidman et al., Biopolymers 22: 547-556 (1983); and EP 133,988).

The pharmaceutical composition of the present invention can be administered to a patient via any appropriate route. For example, it can be administered to a patient intravenously by bolus injection or by continuous infusion, intramuscularly, intraabdominally, intracerebrospinally, transdermally, subcutaneously, intraarticularly, sublingually, intrasynovially, orally, by inhalation, locally, or externally, for a certain period of time. In one embodiment, administration of the pharmaceutical composition of the present invention is systemic administration, and shows an adhesion-suppressing effect at sites of surgical invasion in the whole body.

All prior art documents cited in the present specification are incorporated herein by reference.

Example 1

(Summary of Experimental Results)

The adhesion-suppressing effects of an anti-IL-6 antibody (MP5-20F3) and an anti-IL-6 receptor antibody (MR16-1) were examined using a mouse postoperative intestinal adhesion model. The mouse adhesion model is a model prepared by brief ablation of the mouse cecum using a bipolar electrocautery. Mice were divided into six grades (adhesion scores) ranging from grade 0 to 5 according to the degree of intra-abdominal adhesion formation on the seventh day after surgery. The anti-IL-6 antibody was intraabdominally administered (100 μg/mouse administration group and 1 mg/mouse administration group) one day before surgery, and adhesion was examined on the seventh day. The adhesion scores (M±SEM) were 5.00±0.00 in the PBS-administered group, and 4.67±0.648 (100 μg/mouse administration group) and 5.00±0.00 (1 mg/mouse administration group) in the anti-IL-6 antibody-administered group, so that no adhesion-suppressing effect was observed even when the amount of antibody was increased. Next, the anti-IL-6 receptor antibody (MR16-1) was used to examine the adhesion-suppressing effect. Administration of MR16-1 (10 mg/mouse) one day before surgery gave adhesion scores of 4.83±0.17 in the PBS-administered group and 2.25±0.65 in the MR16-1-administered group, so that a significant (p=0.006) adhesion-suppressing effect was observed. Furthermore, when examined using rat IgG (10 mg/mouse) as the control group, the adhesion scores were 5.00±0.00 for the rat IgG group and 1.00±0.00 for the MR16-1-administered group, so that a significant (p=0.00005) adhesion-suppressing effect was observed. According to histopathological examination, the MR16-1-administered group showed a marked reduction in fibrous tissue/collagen tissue formation and inflammatory cell infiltration of mainly neutrophils at intestinal adhesion sites, which were observed in the PBS group, and this was consistent with the gross visual observation of the adhesion score improvement. In addition, a marked decrease in neutrophil-inducing chemokines (CXCL and CXCL2) was observed in the injured intestinal tissue on the first day after surgery. Furthermore, when the same experiment was performed using a neutralizing antibody against neutrophils (anti-Ly6G antibody), a remarkable adhesion suppression (p=0.0004) was observed in the anti-Ly6G antibody-administered group. These results demonstrate the adhesion-suppressing effect of the anti-IL-6 receptor antibody (MR16-1) in the mouse intestinal adhesion model.

Hereinafter, these study results are described in detail.

Materials and Methods

As mice, 10-week-old female BALB/c mice (weight per animal: 20 g) were used. The intestinal adhesion models were prepared using a bipolar electrocautery burning method on mouse cecum (see Nat. Med. 14: 437-441, 2008). Briefly, the cecum was exposed to the outside of the body through a 5-mm abdominal midline incision, contacted for about one second with a bipolar electrocautery (30 W, 500 kHz, 150Ω), the cecum was returned to the abdominal cavity immediately after burning, the abdominal wall was single-layer sutured, and abdominal closure was performed with a 4-0 prolene thread. The evaluation of intestinal adhesion was performed by sacrificing mice on the seventh day after surgery, and the score was evaluated by gross visual observation using a 6-step evaluation with adhesion scores ranging from 0 to 5 (see Surgery 120: 866-870, 1996). The contents of scores 0 to 5 are as follows:

0: no adhesion;
1: formation of thin membranous adhesion at a single location;
2: formation of thin membranous adhesion at two or more locations;
3: formation of local thick adhesion;
4: formation of thick adhesion attached in the form of dots or formation of thick adhesion at two or more sites;
5: formation of extremely thick adhesion accompanied by neovascularization or formation of locally thick adhesion at two or more sites.

The anti-IL-6 antibody (MP5-20F3) was purchased from SouthernBiotech. MR16-1 was used for the anti-IL-6 receptor antibody. The anti-neutrophil neutralizing antibody (anti-Ly6G) and rat IgG were purchased from Bio X Cell. In experiments for determining the effects of the anti-IL-6 antibody (MP5-20F3), 1 mL of PBS (n=4), or 100 μg/mL/mouse (n=3) or 1 mg/mL/mouse (n=4) of the anti-IL-6 antibody MP5-20F3 was intraabdominally administered 24 hours before surgery. Also, in the anti-IL-6 receptor antibody (MR16-1) experiment, 1 mL/mouse of PBS (n=10), 10 mg/mL/mouse of rat IgG (n=4), 2 mg/mL/mouse of the anti-IL-6 receptor antibody MR16-1 (n=3), or 10 mg/mL/mouse of MR16-1 (n=11) was intraabdominally administered 24 hours before the operation. In the neutrophil-neutralizing antibody experiments, 500 μg of the isotype (n=5) and 500 μg (n=6) of the anti-Ly6G antibody were intraabdominally administered.

On the seventh day after surgery, a pathological specimen containing the adhered intestine was sampled, and after fixation using formalin or a zinc solution, paraffin blocks were prepared, and thin slices of the blocks were used to perform Hematoxylin-Eosin (HE) staining. The evaluation of fibrosis was performed by Azan Mallory/Sirius Red staining. Evaluation of infiltration and accumulation of neutrophils into tissues was performed by Ly6G immunostaining (anti-Ly6G antibody was purchased from BD Pharmingen). Moreover, mRNA was purified from the specimen. Then, the purified mRNA sample was subjected to real time PCR to measure the expression levels of CXCL1 and CXCL2.

Statistical analyses were performed using Student's t-test in all experiments, and P<0.05 was determined to show existence of significant difference.

(Result 1) Anti-IL-6 Antibody (MP5-20F3) Administration Experiment

Figure 2:
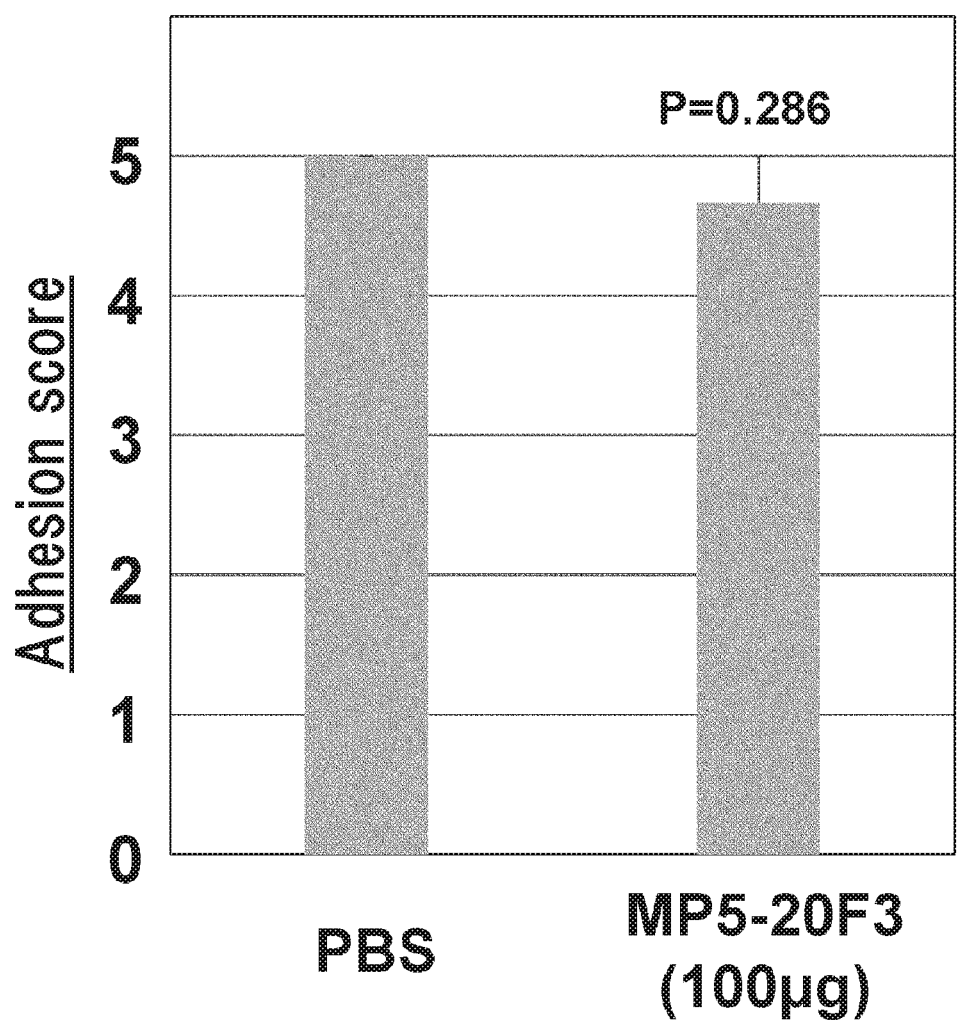
FIG. 2 is a graph showing the adhesion scores of the damaged portion of the intestinal tract of the PBS-administered group and the MP5-20F3-administered group (100 mg/mouse).
Figure 3:
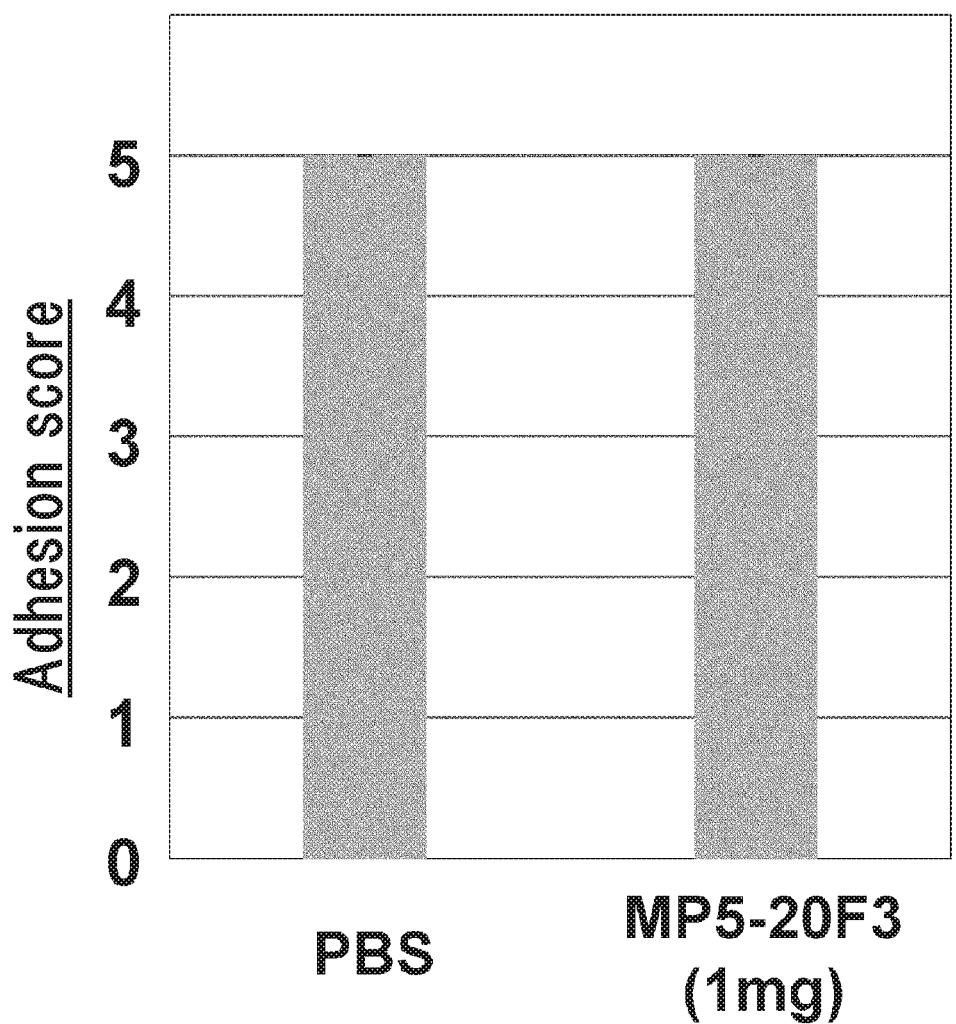
FIG. 3 is a graph showing the adhesion scores of the damaged portion of the intestinal tract of the PBS-administered group and the MP5-20F3-administered group (1 mg/mouse).

For the PBS-administered group, both the PBS-administered group (n=4) used as a control group for the MP5-20F3 (100 mg/mouse)-administered group and the PBS-administered group (n=4) used as a control group for the MP5-20F3 (1 mg/mouse)-administered group were found to show strong adhesion with an adhesion score of 5 (FIG. 1). The adhesion scores of the MP5-20F3-administered group were 4.67±0.648 (100 mg/mouse administration group: n=3) and 5.00±0.00 (1 mg/mouse administration group: n=4), and no adhesion-suppressing effect was observed even when the amount of antibody was increased (FIGS. 2 and 3).

(Result 2) Anti-IL-6 Receptor Antibody (MR16-1) Administration Experiment

Figure 4:
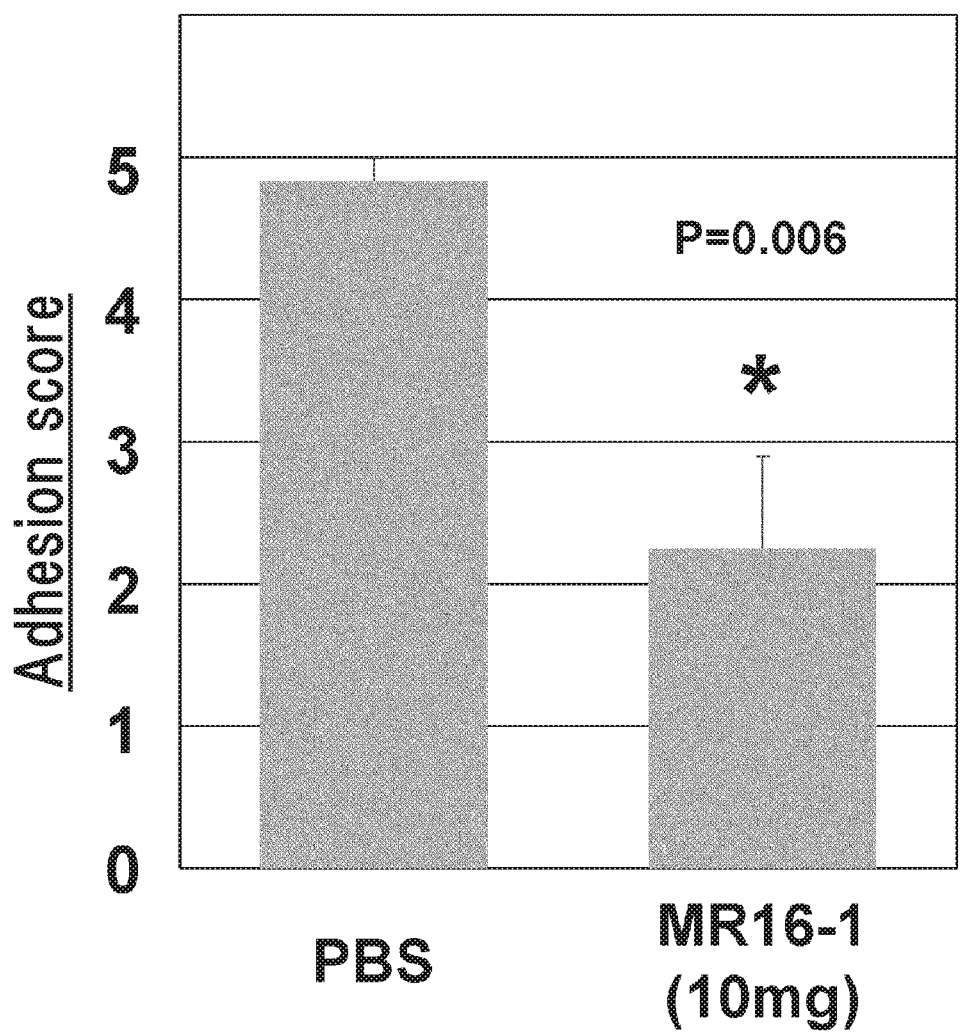
FIG. 4 is a graph showing the adhesion scores of the damaged portion of the intestinal tract of the PBS-administered group and the MR16-1-administered group (10 mg/mouse).
Figure 5:
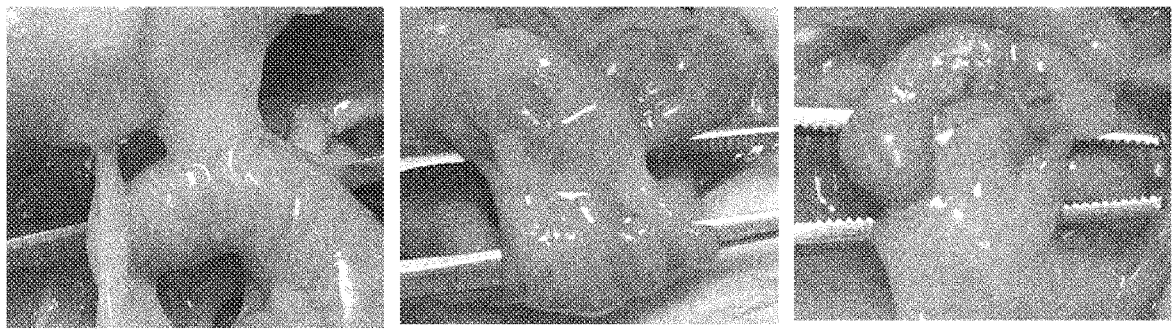
FIG. 5 is a set of photographs of the damaged portion of the intestinal tract of the PBS-administered group and the MR16-1-administered group.
Figure 5:
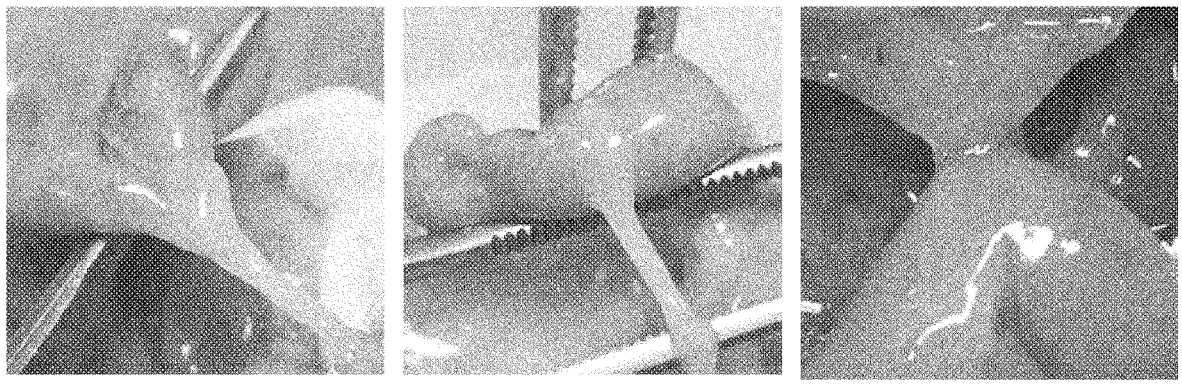

Adhesion score for the PBS-administered group (n=10) used as a control group was 4.83±0.167, and the adhesion score of the MR16-1 (10 mg/mL/mouse)-administered group (n=8) was 2.25±0.648, and a significant (p=0.006) adhesion-suppressing effect was observed by administration of MR16-1 at 10 mg/mL/mouse (FIGS. 4 and 5).

Figure 6:
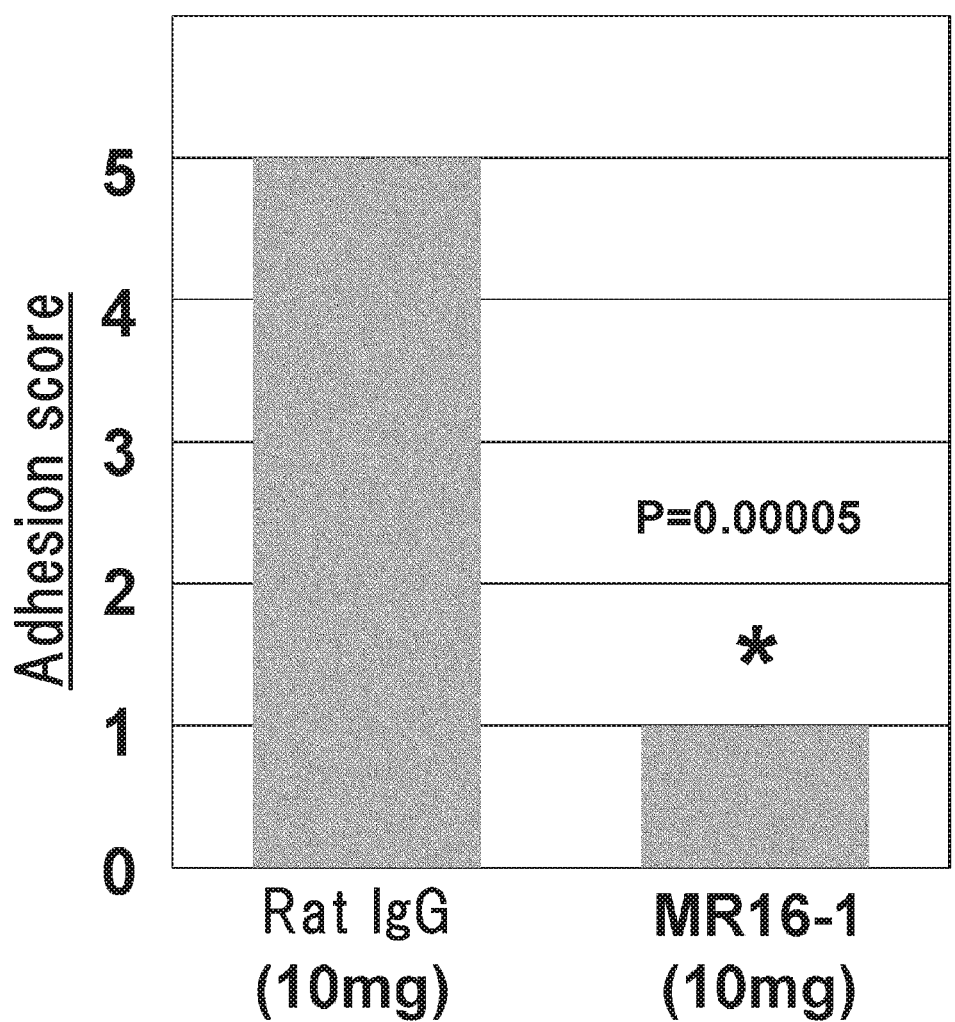
FIG. 6 is a graph showing the adhesion scores of the damaged portion of the intestinal tract of the rat IgG-administered group and the MR16-1-administered group.

Furthermore, when examined using rat IgG (10 mg/mouse) as the control group, the adhesion score for the rat IgG-administered group (n=4) was 5.00±0.00, the adhesion score for the MR16-1 (10 mg/mL/mouse)-administered group (n=3) was 1.00±0.00, and a significant (p=0.00005) adhesion-suppressing effect was observed by administration of MR16-1 at 10 mg/mL/mouse (FIG. 6).

Figure 7:
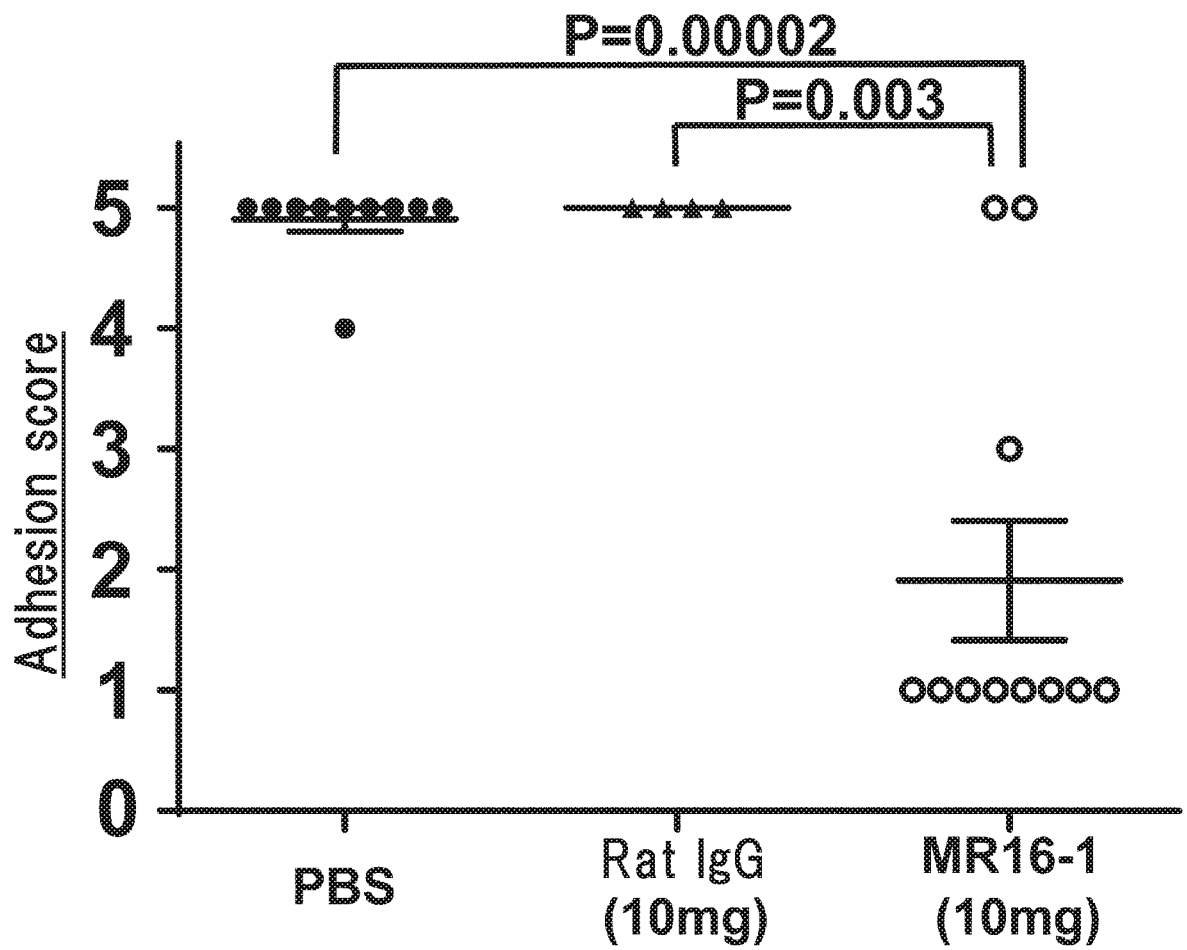
FIG. 7 is a graph showing the adhesion scores of the damaged portion of the intestinal tract of the PBS-administered group, the rat IgG-administered group, and the MR16-1-administered group.

To summarize the results of the above MR16-1 administration experiment (FIG. 7), the MR16-1 (10 mg/mL/mouse)-administered group (n=11) demonstrated a significant (p=0.00002) adhesion-suppressing effect as compared to the PBS-administered group (n=10), and also demonstrated a significant (p=0.003) adhesion-suppressing effect as compared to the rat IgG (10 mg)-administered group (n=4).

Figure 8:
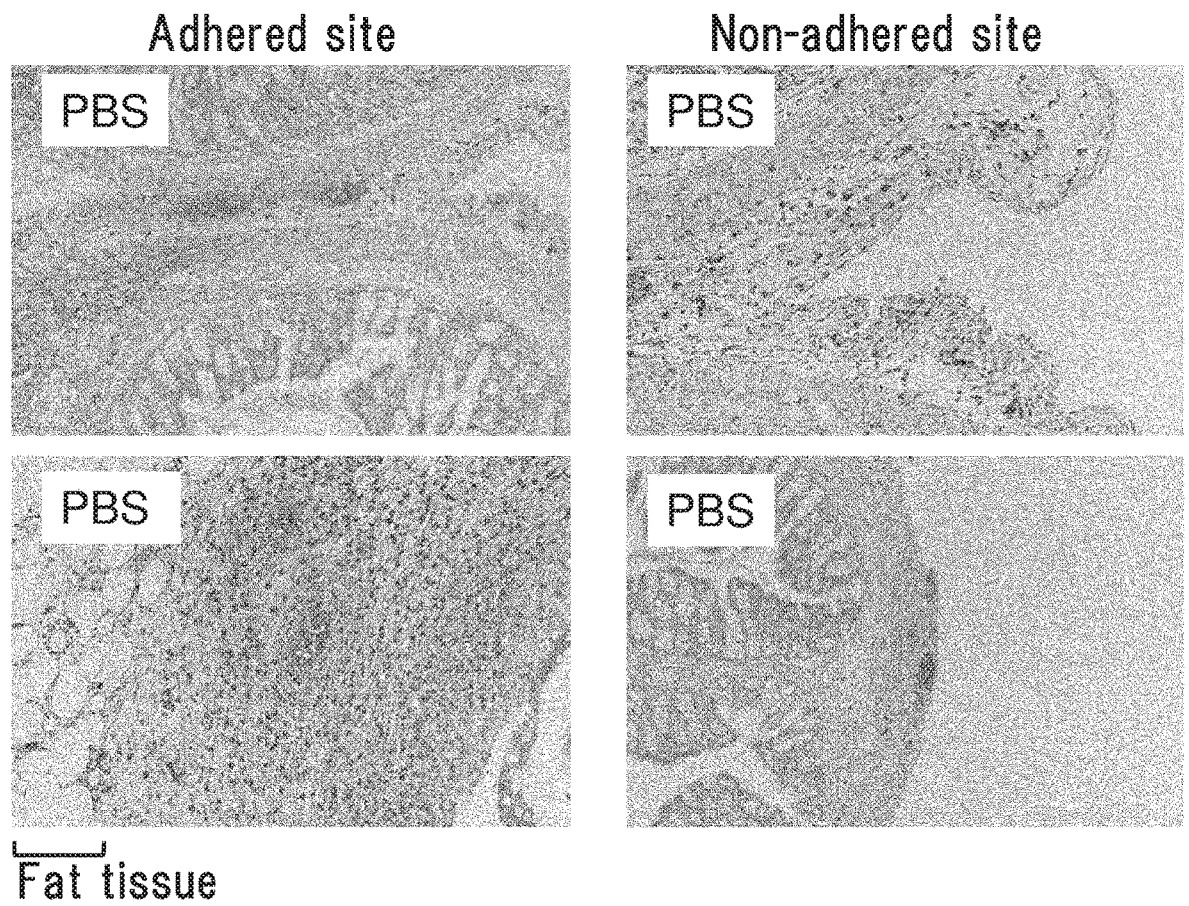
FIG. 8 is a set of photographs showing the Ly-6G staining results of the adhered and non-adhered portions of the intestinal tract of the PBS-administered group.
Figure 9:
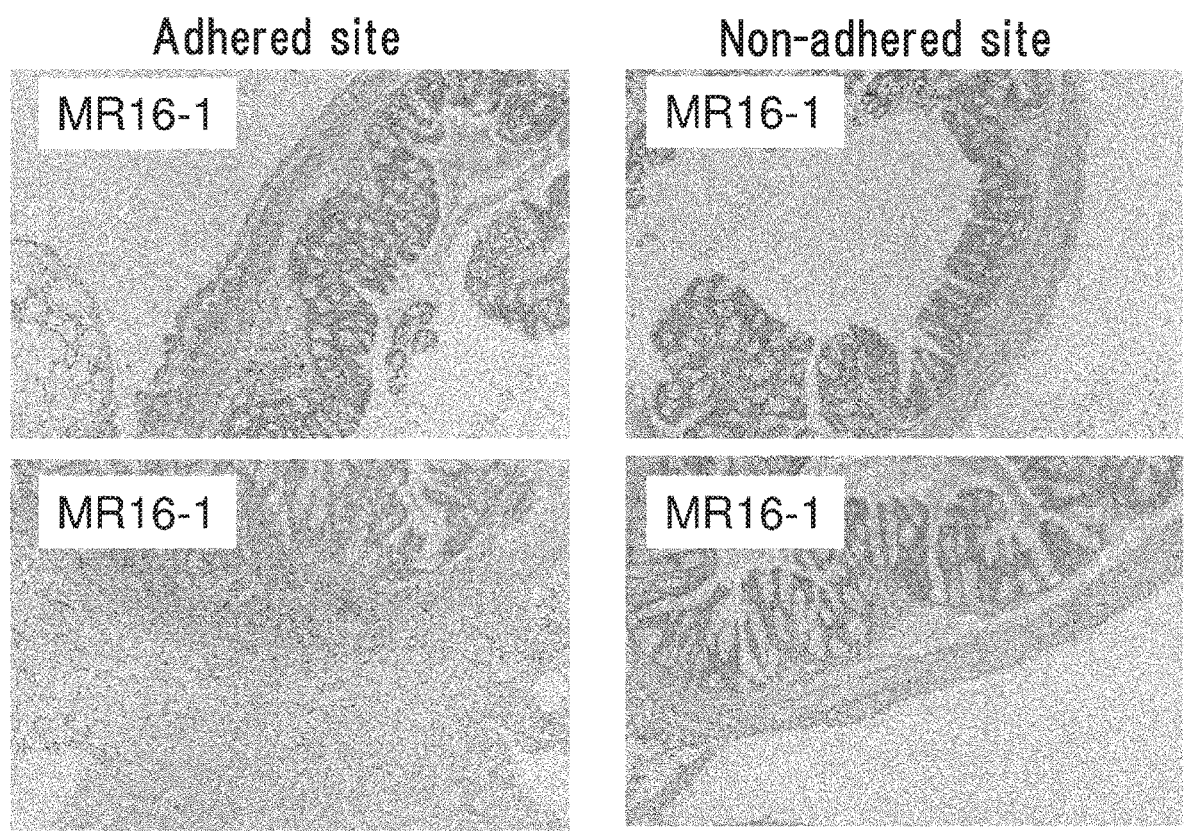
FIG. 9 is a set of photographs showing the Ly-6G staining results of the adhered and non-adhered portions of the intestinal tract of the MR16-1-administered group.

(Result 3) Histopathological Examination of the Intestinal Tissue at the Site of Adhesion and Measurement of Chemokines in the Tissue In the MR16-1-administered group, a marked decrease in inflammatory findings and fibrous tissues were observed by HE staining as well as fibrous immunostaining. When tissue infiltration of neutrophils was examined by immunostaining (Ly-6G staining), tissue infiltration of neutrophils was found to be markedly reduced in both the adhesion and non-adhesion sites of the intestine in the MR16-1 (10 mg/mL/mouse)-administered group (FIG. 9) in comparison to the PBS-administered group (FIG. 8).

Figure 10:
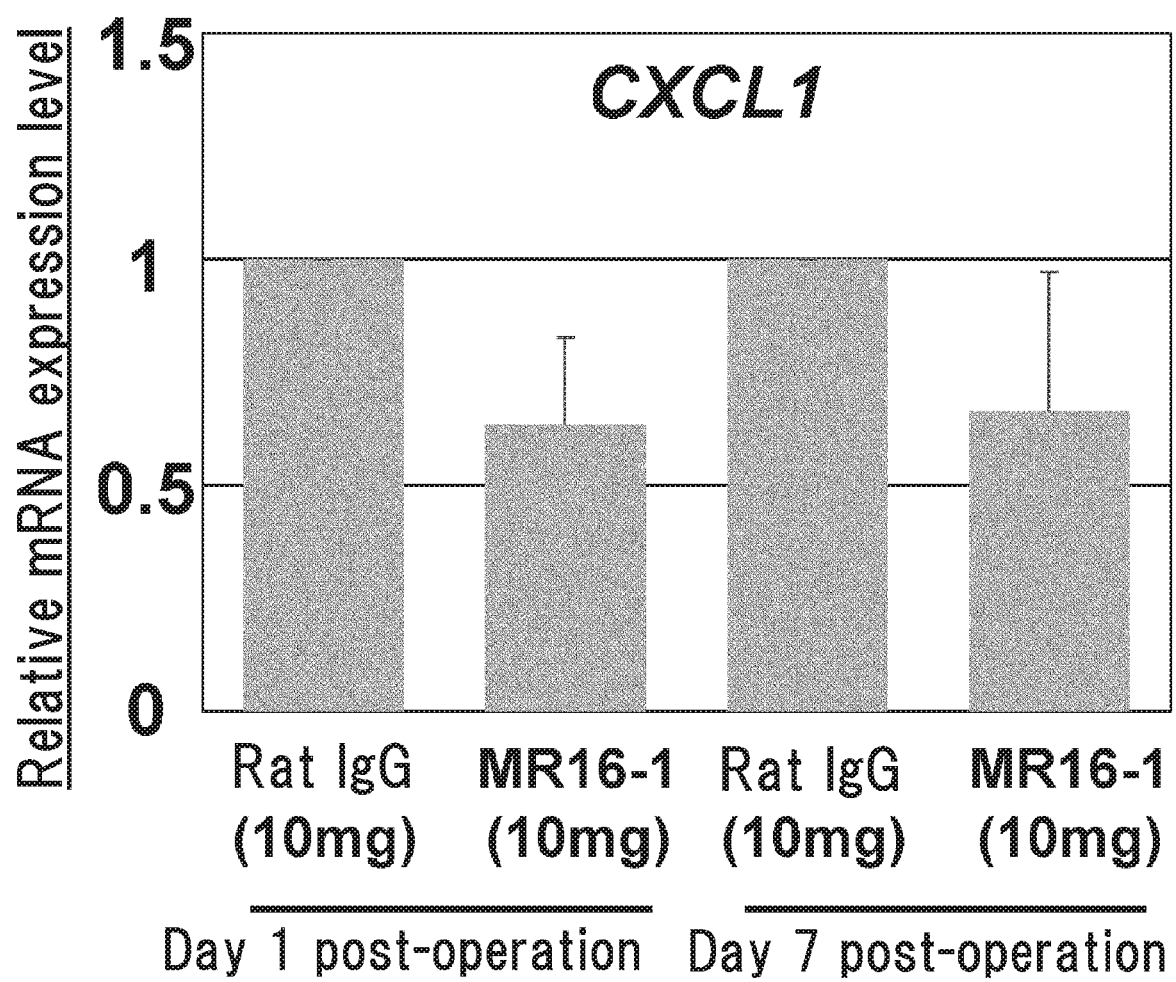
FIG. 10 is a graph showing the relative mRNA expression levels of CXCL1 in the damaged portion of the intestinal tract of the rat IgG-administered group and the MR16-1-administered group.
Figure 11:
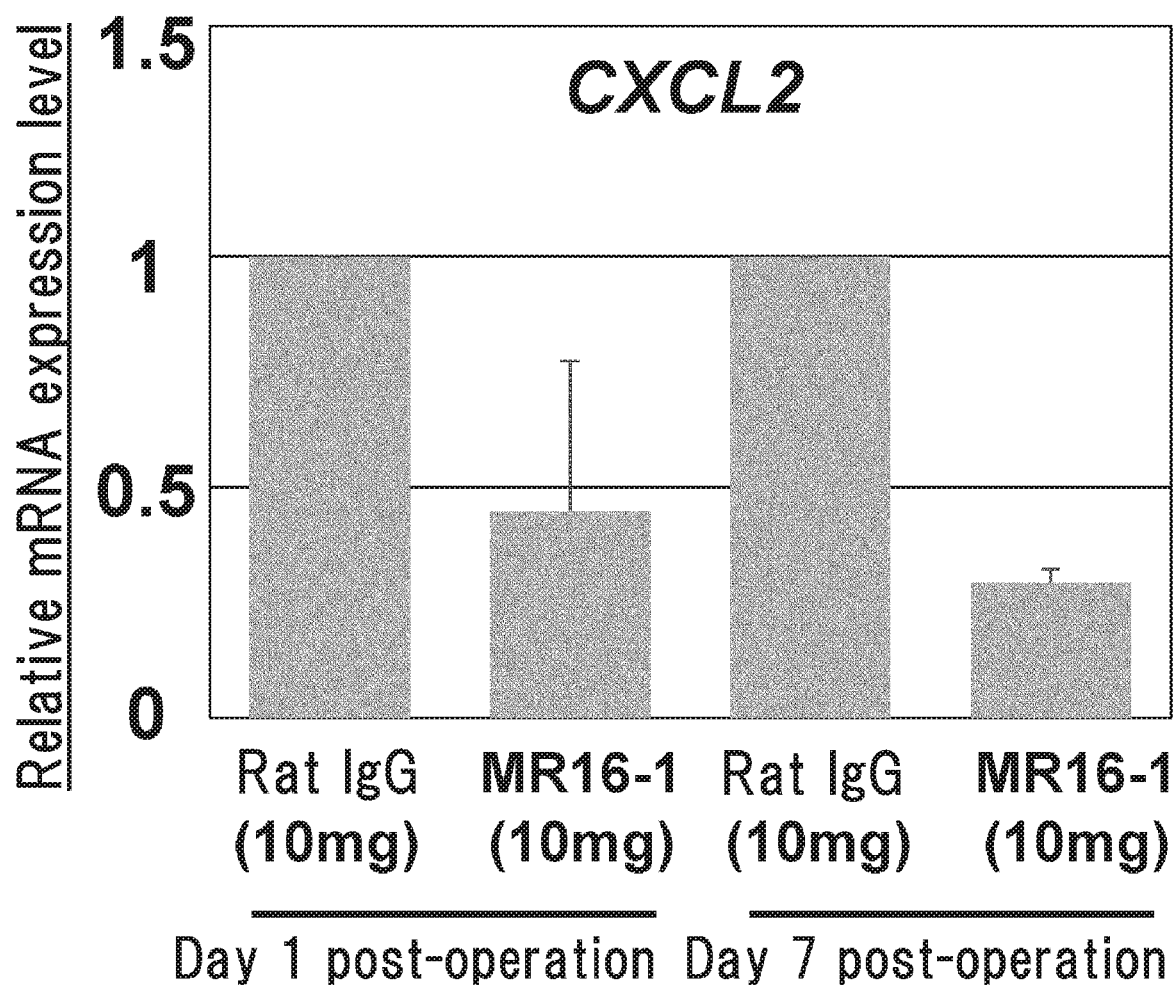
FIG. 11 is a graph showing the relative mRNA expression levels of CXCL2 in the damaged portion of the intestinal tract of the rat IgG-administered group and the MR16-1-administered group.

In addition, when mRNA expressions at the damaged intestine part of CXCL1/CXCL2, which are chemokines related to neutrophil migration, were measured by real time PCR, a marked decrease in the CXCL1/CXCL2 expression levels was observed on both the first day and seventh day after surgery in the MR16-1 (10 mg/mouse)-administered group (FIGS. 10 and 11).

(Result 4) Intestinal Adhesion-Suppressing Experiment by Administration of a Neutrophil-Neutralizing Antibody (Anti-Ly-6G Antibody)

Figure 12:
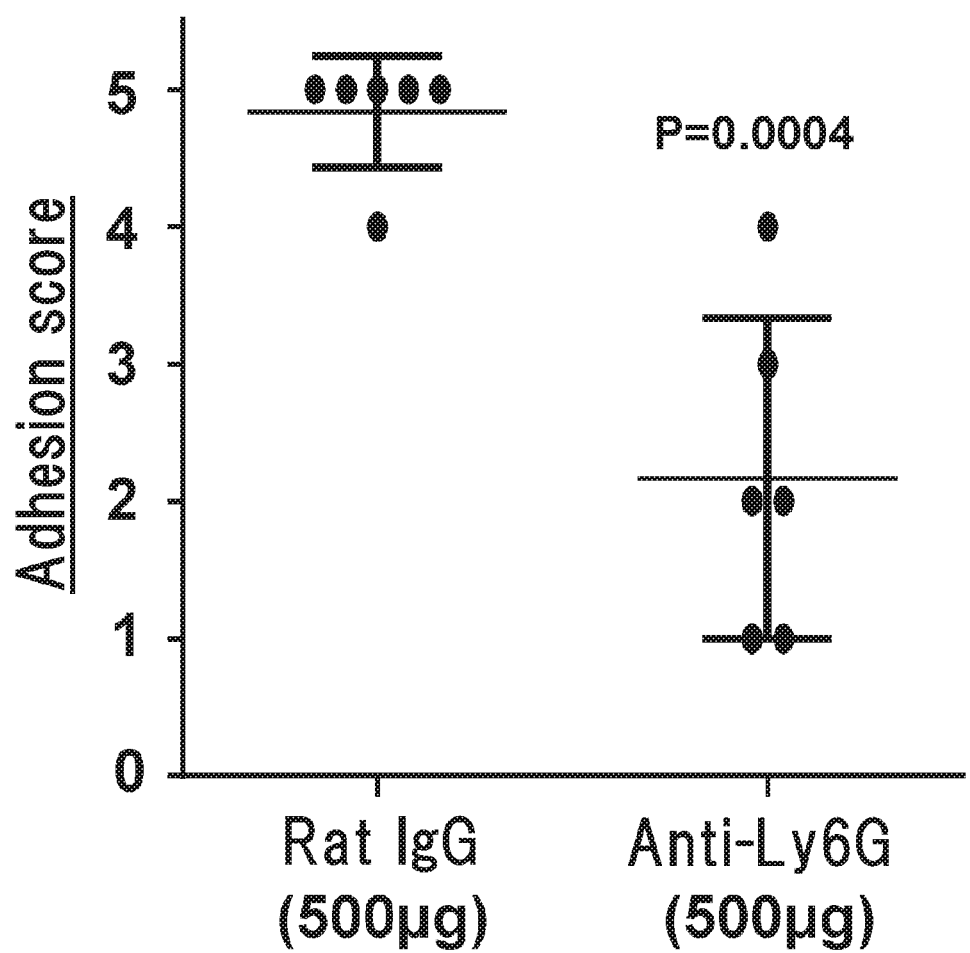
FIG. 12 is a graph showing the adhesion scores of the damaged portion of the intestinal tract of the rat IgG-administered group and the anti-Ly-6G antibody-administered group.

The adhesion score of the rat IgG-administered group (n=6) was 4.83±0.24, but the adhesion score of the anti-Ly-6G antibody-administered group (n=6) was 2.17±0.67, so that a significant (p=0.0004) adhesion-suppressing effect was observed by anti-Ly-6G antibody administration (FIG. 12).

Example 2

Objective

The suppressive effect of MR16-1 on wound healing was examined in a full-thickness skin defect model prepared using a skin biopsy punch.

Method

The animals used were Balbc mice (male, 8 weeks old), and a control group (n=4) which was given intraabdominal administration of 10 mg of Rat IgG and a subject group (n=4) which was given intraabdominal administration of MR16-1 (10 mg) were prepared 24 hours before performing skin defect treatment using a biopsy punch. The skin defect treatment was performed by shaving the back under isoflurane (concentration: 3%; carrier gas: 30% oxygen and 70% laughing gas) inhalation anesthesia, wiping using ethanol for disinfection, and then making skin excisions of approximately 5 mm in diameter using a skin biopsy punch (Nipro Corp., Osaka). The area of the skin defect was measured over time from the day of treatment to evaluate wound healing, and the wound healing-suppressing effect of MR16-1 was examined by comparison between the Rat IgG-administered group and the MR16-1-administered group. The area was measured using J-image (free software from NIH) after taking photographs of the skin defects.

Results

Figure 13:
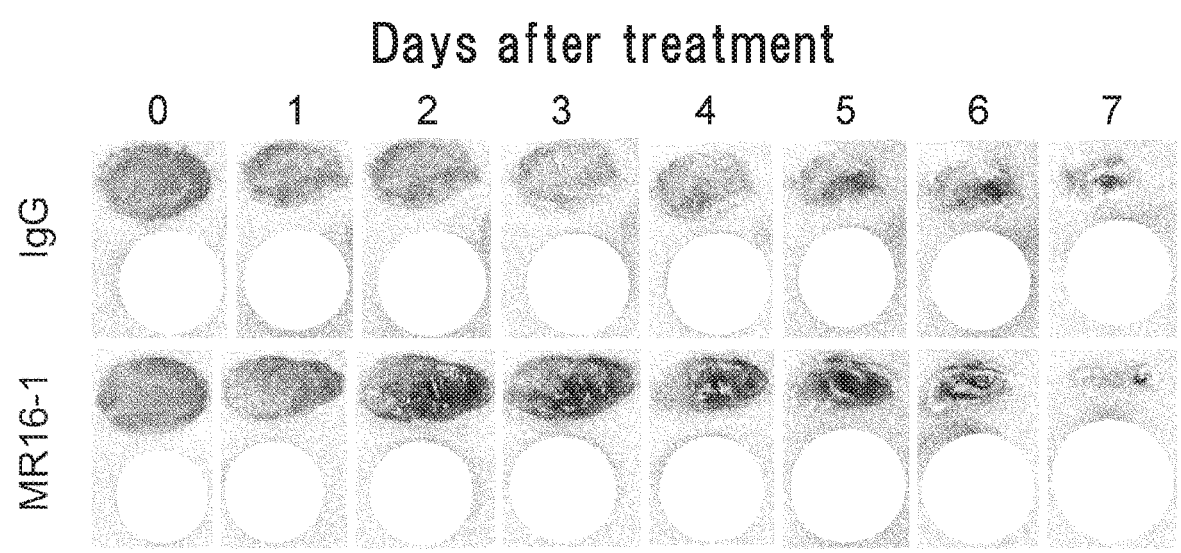
FIG. 13 is a set of photographs showing the wound healing process of the rat IgG-administered group and the MR16-1-administered group. The changes in the defective part of the skin produced by a skin biopsy punch are shown.
Figure 14:
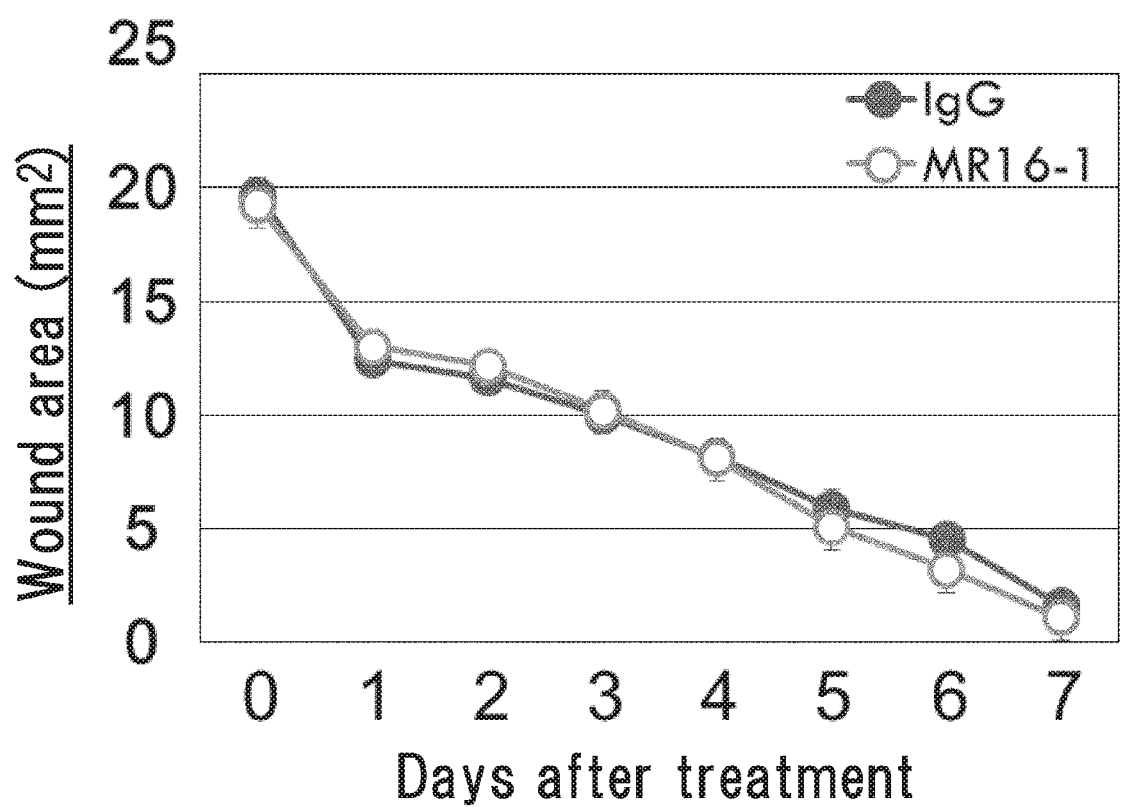
FIG. 14 is a graph showing the influence of MR16-1 on wound healing. The wound healing process in a skin defect model using a skin biopsy punch on the MR16-1-administered group was compared to that of the rat IgG-administered group used as a control. No significant wound healing-suppressing effect was observed by the administration of MR16-1 during the 7-day observation period.

Areas of skin defects in the Rat IgG-administered group and the MR16-1-administered group on the day of treatment were 19.68±0.75 mm2 and 19.20±0.53 mm2, respectively (FIGS. 1 and 2). Skin defect areas in the Rat IgG-administered group and the MR16-1-administered group on the third day and seventh day after treatment were 9.98±1.11 mm2 and 10.21±0.65 mm2, respectively (on the third day), and 1.6±0.291.11 mm2 and 1.07±0.09 mm2, respectively (on the seventh day), so that there was no significant difference in wound healing between the two groups (FIGS. 13 and 14). From the above-mentioned results, no significant suppressive effect by MR16-1 was observed on skin defect wound healing.

Therefore, administration of an IL-6 receptor antibody is expected to suppress postoperative adhesion formation and achieve wound healing at a site of invasion.

INDUSTRIAL APPLICABILITY

The pharmaceutical compositions of the present invention provide new means that can achieve the effects of suppressing neutrophil migration, and consequently suppressing postoperative adhesion formation.

The invention claimed is:

1. A method for suppressing postoperative adhesion, which comprises administering an effective amount of an anti-IL-6 receptor antibody to a subject, wherein the adhesion is gastrointestinal adhesion or liver adhesion.

2. The method of claim 1, wherein the anti-IL-6 receptor antibody is administered to the subject preoperatively.

3. The method of claim 1, wherein the adhesion is intestinal adhesion.

4. The method of claim 1, wherein the adhesion is gastrointestinal adhesion.

5. The method of claim 1, wherein the adhesion is liver adhesion.

6. The method of claim 1, wherein the administered anti-IL-6 receptor antibody is tocilizumab.

7. The method of claim 1, wherein the administered anti-IL-6 receptor antibody comprises a heavy-chain variable region comprising the sequence of SEQ ID NO: 1 and a light-chain variable region comprising the sequence of SEQ ID NO: 2.

8. The method of claim 1, wherein the administered anti-IL-6 receptor antibody comprises a heavy-chain region comprising the sequence of SEQ ID NO: 3 and a light-chain region comprising the sequence of SEQ ID NO: 4.

9. The method of claim 2, wherein the administered anti-IL-6 receptor antibody is tocilizumab.

10. The method of claim 2, wherein the administered anti-IL-6 receptor antibody comprises a heavy-chain variable region comprising the sequence of SEQ ID NO: 1 and a light-chain variable region comprising the sequence of SEQ ID NO: 2.

11. The method of claim 2, wherein the administered anti-IL-6 receptor antibody comprises a heavy-chain region comprising the sequence of SEQ ID NO: 3 and a light-chain region comprising the sequence of SEQ ID NO: 4.

* * * * *